[54] PHENYLALANINE DERIVATIVE AND PROTEINASE INHIBITOR

[75] Inventors: Shosuke Okamoto, Kobe; Yoshio Okada, Akashi; Akiko Okunomiya, Kobe; Taketoshi Naito, Tokyo; Yoshio Kimura, Tokyo; Morihiko Yamada, Tokyo; Norio Ohno, Tokyo; Yasuhiro Katsuura, Tokyo; Yumi Seki, Tokyo, all of Japan

[73] Assignees: Shosuke Okamoto, Hyogo; Showa Denko Kabushiki Kaisha, Tokyo, both of Japan

[21] Appl. No.: 912,480

[22] Filed: Sep. 29, 1986

[30] Foreign Application Priority Data

Sep. 27, 1985 [JP] Japan ................................ 60-212240
Mar. 4, 1986 [JP] Japan ................................ 61-45348

[51] Int. Cl.$^4$ ................... A61K 31/165; C07C 103/28
[52] U.S. Cl. .................. 514/227.5; 514/237.5; 514/255; 514/269; 514/330; 514/349; 514/352; 514/512; 514/518; 514/530; 514/539; 514/542; 514/563; 514/603; 514/666; 514/554; 514/555; 544/58.4; 544/169; 544/329; 544/335; 544/386; 544/387; 546/224; 546/226; 546/265; 546/297; 546/309; 546/315; 546/333; 548/540; 558/50; 558/273; 560/37; 560/39; 560/41; 560/42; 562/442; 562/448; 562/450; 562/451; 562/579; 562/582; 562/584; 562/590; 562/597; 564/86; 564/153; 564/154; 564/157

[58] Field of Search ................. 564/157, 153, 154, 86; 544/58.4, 169, 386, 387, 329, 335; 546/224, 226, 265, 297, 309, 315, 333; 548/540; 558/50, 273; 560/37, 39, 41, 42; 260/501.18, 505 R, 513 R; 562/442, 448, 450, 451, 579, 582, 584, 590, 597; 514/222, 234, 255, 269, 330, 349, 352, 512, 518, 530, 539, 542, 563, 603, 616, 554, 555

[56] References Cited

U.S. PATENT DOCUMENTS 4,261,919  4/1981  Knowles et al. .................... 548/497

FOREIGN PATENT DOCUMENTS 0183271  1/1986  European Pat. Off. .

OTHER PUBLICATIONS

101:111406k English Chemical Abstract, Chemical Abstracts, vol. 101, (1984), p. 702.
Voight Pharmazie, 39, H.1, (1984), pp. 68 and 69, (cited by applicants).
CA 82-27789u, FEBS Lett., vol. 43, p. 281, (1974).
CA 103-209699z, Il Farmco. Ed. Sc., vol. 40, p. 717, (1985).
CA 49-12707g, Antibiotics & Chemotherapy, vol. 5, p. 152, (1955).
CA 101-7612p, Pharmazie, vol. 39H1, p. 68, (1984).
CA 53-9299g, J. Biochem., (Tokyo), vol. 46, p. 19, (1959).
CA 93-101418t, Biochem. Biophys. Res. Comm., vol. 94, pf. 284, (1980).
CA 84-160982j, Bioklimiya, vol. 41, p. 294, (1976).

Primary Examiner—Mary C. Lee
Assistant Examiner—Bernard I. Dentz
Attorney, Agent, or Firm—Sughrue, Mion, Zinn, Macpeak & Seas

[57] ABSTRACT

A phenylalanine derivative having the formula (I):

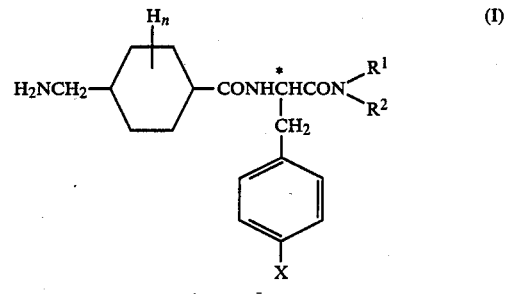

where
$R^1$ and $R^2$ are independently hydrogen provided that both $R^1$ and $R^2$ are not hydrogen at the same time;
$C_1$-$C_8$ alkyl which may be substituted with hydroxy, hydroxycarbonyl, $C_1$-$C_4$ alkoxycarbonyl, $C_1$-$C_4$ alkylmercapto, $C_1$-$C_4$ alkoxy, carbamoyl, sulfamoyl, pyridyl, or phenyl which may further be substituted with nitro, $C_1$-$C_4$ alkoxy, or halogen;
$C_6$-$C_8$ cycloalkyl which may be substituted with hydroxy, $C_1$-$C_4$ alkoxy, hydroxylcarbonyl, $C_1$-$C_4$ alkoxycarbonyl, or $C_1$-$C_4$ alkyl;
phenyl which may be substituted with halogen, nitro, trifluoromethyl, $C_1$-$C_4$ alkoxy $C_1C_4$ alkylmercapto, $C_1$-$C_4$ alkylcarbonyl, phenylcarbonyl, hydroxycarbonyl, $C_1$-$C_4$ alkoxycarbonyl, carbamoyl, sulfamoyl, amidino, pyridylcarbonyl, or $C_1$-$C_6$ alkyl which may further be substituted with $C_1$-$C_4$ alkylcarbonyl, hydroxycarbonyl, or $C_1$-$C_4$ alkoxycarbonyl;
pyridyl which may be substituted with halogen or $C_1$-$C_4$ alkoxy;
pyrimidyl;
N-benzylazacyclohexyl; and
$R^1$ and $R^2$ may form with the nitrogen atom attached thereto a ring structure as morpholino; thiomorpholino; piperazino which may be substituted with phenylcarbonyl, benzyl, or $C_1$-$C_4$ alkyl;
pyrrolidyl which may be substituted with hydroxycarbonyl or $C_1$-$C_4$ alkoxycarbonyl; and
piperidino substituted with $C_1$-$C_4$ alkyl, phenyl $C_1$-$C_4$ alkyl, phenylcarbonyl, or $C_1$-$C_4$ alkoxycarbonyl;
X is hydrogen; nitro; amino; or —OZ wherein Z is hydrogen; $C_1$-$C_4$ alkyl; $C_2$-$C_4$ alkenyl; benzyl which may be substituted with halogen, $C_1$-$C_4$ alkyl, nitro, trifluoromethyl, hydroxycarbonyl, $C_1$-$C_4$ alkoxycarbonyl, or cyano; phenylcarbonylmethyl; pyridylmethyl; phenyl which may be sub-
(Abstract continued on next page.)

stituted with nitro or halogen; pyridyl or pyrimidyl which may be substituted with nitro; phenylsulfonyl which may be substituted with $C_1$–$C_4$ alkyl; or benzyloxycarbonyl which may be substituted with halogen;

n is 4 to 10; and the mark * indicates that the configuration of the carbon may be either one of D-configuration, L-configuration and DL-configuration or a pharmaceutical acceptable salt thereof.

This phenylalanine derivative is effective as a proteinase inhibitor.

4 Claims, No Drawings

PHENYLALANINE DERIVATIVE AND PROTEINASE INHIBITOR

BACKGROUND OF THE INVENTION

1. Field of the Invention

The present invention relates to a novel phenylalanine derivative, more particularly to a phenylalanine derivative having a proteinase inhibition activity or a pharmaceutically acceptable salt thereof. The present invention also relates to a proteinase inhibitor containing the phenylalanine derivative as the effective ingredient.

2. Description of the Related Art

It is well known in the art that various proteinases are present in human organisms. Examples of such proteinases are plasmin, trypsin, kallikrein, urokinase, and the like. As is also known, when these proteinases are abnormally activated for some reason, various diseases are caused. For example, hemorrhagic diseases are caused when abnormally activated plasmin is present in a relatively large amount in the blood. Also, plasmin participates in inflammation and it is considered to cause inflammatory diseases. For this reason, a substance capable of exhibiting a proteinase inhibition activity is useful as a clinical remedy or medicine, and various investigations in the prior art have been made for the development of such substances. For example, antiplasmins are useful as hematostatic agents, antiinflammatory agents or antiallergic agents, antitrypsins are useful for the therapy of pancreatitis, antikallikreins are useful as therapeutical agents for inflammation, and antiurokinases are useful for the inhibition of hemorrhagic symptoms in the thrombolytic therapeutical method with urokinase. Accordingly, developments of proteinase inhibitors having such activities have progressed in the prior art, but their proteinase inhibition activities are low and not satisfactory for practical application as medicines. Further, compounds having satisfactory inhibition activities against various proteinases have not been developed.

SUMMARY OF THE INVENTION

Accordingly, the objects of the present invention are to eliminate the above-mentioned disadvantages of the prior art and to provide a compound having a satisfactory inhibition activity in practical application but still having satisfactory inhibition activities against various proteinases, and a proteinase inhibitor containing the compound as the effective ingredient.

Other objects and advantages of the present invention will be apparent from the following description.

In accordance with the present invention, there is provided a phenylalanine derivative having the formula (I):

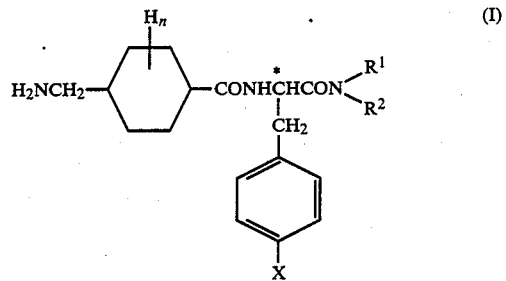

where
- $R^1$ and $R^2$ are independently hydrogen provided that both $R^1$ and $R^2$ are not hydrogen at the same time;
- $C_1$–$C_8$ alkyl which may be substituted with hydroxy, hydroxycarbonyl, $C_1$–$C_4$ alkoxycarbonyl, $C_1$–$C_4$ alkylmercapto, $C_1$–$C_4$ alkoxy, carbamoyl, sulfamoyl, pyridyl, or phenyl which may further be substituted with nitro, $C_1$–$C_4$ alkoxy, or halogen;
- $C_6$–$C_8$ cycloalkyl which may be substituted with hydroxy, $C_1$–$C_4$ alkoxy, hydroxylcarbonyl, $C_1$–$C_4$ alkoxycarbonyl, or $C_1$–$C_4$ alkyl;
- phenyl which may be substituted with halogen, nitro, trifluoromethyl, $C_1$–$C_4$ alkoxy, $C_1$–$C_4$ alkylmercapto, $C_1$–$C_4$ alkylcarbonyl, phenylcarbonyl, hydroxycarbonyl, $C_1$–$C_4$ alkoxycarbonyl, carbamoyl, sulfamoyl, amidino, pyridylcarbonyl, or $C_1$–$C_6$ alkyl which may further be substituted with $C_1$–$C_4$ alkylcarbonyl, hydroxycarbonyl, or $C_1$–$C_4$ alkoxycarbonyl;
- pyridyl which may be substituted with halogen or $C_1$–$C_4$ alkoxy;
- pyrimidyl;
- N-benzylazacyclohexyl; and
- $R^1$ and $R^2$ may form with the nitrogen atom attached thereto a ring structure as morpholino; thiomorpholino; or piperazino which may be substituted with phenylcarbonyl, benzyl, or $C_1$–$C_4$ alkyl;
- pyrrolidyl which may be substituted with hydroxycarbonyl or $C_1$–$C_4$ alkoxycarbonyl; and
- piperidino substituted with $C_1$–$C_4$ alkyl, phenyl $C_1$–$C_4$ alkyl, phenylcarbonyl, or $C_1$–$C_4$ alkoxycarbonyl;
- X is hydrogen; nitro; amino; or —OZ wherein Z is hydrogen; $C_1$–$C_4$ alkyl; $C_2$–$C_4$ alkenyl; benzyl which may be substituted with halogen, $C_1$–$C_4$ alkyl, nitro, trifluoromethyl, hydroxycarbonyl, $C_1$–$C_4$ alkoxycarbonyl, or cyano; phenylcarbonylmethyl; pyridylmethyl; phenyl which may be substituted with nitro or halogen; pyridyl or pyrimidyl which may be substituted with nitro; phenylsulfonyl which may be substituted with $C_1$–$C_4$ alkyl; or benzyloxycarbonyl which may be substituted with halogen;
- n is 4 to 10; and
- the mark * indicates that the configuration of the carbon may be either one of a D-configuration, L-configuration and DL-configuration, or a pharmaceutical acceptable salt thereof. Examples of such a salt may include inorganic acid salts such as hydrochloride, hydrobromide, hydroiodide, sulfate, nitrate, phosphate, etc.; organic salts such as oxalate, succinate, glycolate, malate, citrate, maleate, lactate, benzenesulfonate, toluenesulfonate, methanesulfonate, etc.

In accordance with the present invention, there is also provided a proteinase inhibitor comprising the phenylalanine derivative of the above formula (I) or a pharmaceutically acceptable salt thereof as the active ingredient.

DESCRIPTION OF THE PREFERRED EMBODIMENTS

Typical examples of the compound represented by the above formula are listed in Table 1.

The compounds listed in the Table are mumbered, respectively, and in the following description, the individual compounds are designated in terms of said compound Nos. for the purpose of convenience.

For the compounds indicated as (DL) in the chemical structure, this means that their carbons are mixtures of D- and L-forms; in the compounds indicated as (L), this means that their carbons are L-form; and, in the compounds indicated as (D), this means that its carbon is D-form. The asymmetric carbon atoms in the phenylalanine skeleton having no indications are all L-forms. In the physical properties shown in Table 1, NMR represents a nuclear magnetic resonance spectrum indicated by $\delta$ (i.e., delta) (ppm) representing the chemical shifts. The determination was carried out by using as a solvent $CDCl_3$ (i.e., heavy chloroform), $(CD_3)_2SO$ (i.e., $d_6$-dimethylsulfoxide), $D_2O$ (i.e., heavy water), or $CD_3OD$ (i.e., heavy methanol) alone or in any mixture thereof, and by using as an internal standard TMS (i.e., tetramethylsilane). In the parenthesis after the $\delta$ number, the number of the hydrogen atom and the symbols s, d, t, q, m, and broad, thereafter, denote singlet, doublet, triplet, quartet, multiplet, and broad absorbance, respectively. The absorbance based on the solvent is omitted from the Table.

IR represents an infrared absorption spectrum in which a potassium bromide tablet is used in the determination unless otherwise noted. When a solution is used in the determination, the kind of solvent is listed in parenthesis. The number listed in the Table represents a wave number in units of $cm^{-1}$, and only the main absorption peaks are listed in the Table.

MS represents a mass spectrum, and the results are shown as M/e (i.e., the mass of the cation fragment divided by the charge) of the main peaks.

TABLE 1

| No. | Compound | Physical Properties |
|---|---|---|
| 1 | [structure: phenyl-CH2-CH(CONH-cyclohexyl-CH2NH2)-CONH-C6H4-C(=O)-phenyl] | NMR: CDCl3, TMS δ 0.80–2.20(10H, m) 2.40–2.60(2H, d) 2.80–3.30(3H, m) 4.70–4.90(1H, t) 7.10–7.90(14H, m)<br>MS: M/e 483, 327, 287, 253 |
| 2 | [structure: phenyl-CH2-CH(CONH-cyclohexyl-CH2NH2)-CONH-C6H4-C(=O)CH3] | NMR: 20%CD3OD—CDCl3, TMS δ 0.80–2.20(10H, m) 2.52(2H, d) 2.60(3H, s) 2.90–3.24(2H, m) 4.76(1H, m) 7.12–7.96(9H, m)<br>IR: 3300, 2925, 2850, 1675, 1640, 1595, 1520, 1310, 1265, 1255, 1175, 815, 695 |
| 3 | [structure: 4-phenoxyphenyl-CH2-CH(CONH-cyclohexyl-CH2NH2)-CONH-C6H4-C(=O)CH3] | NMR: 5% CDCl3—CD3OD, TMS δ 0.76–2.28(10H, m) 2.49(2H, d) 2.56(3H, s) 2.84–3.20(2H, m) 4.68(1H, m) 5.02(2H, s) 6.80–7.93(13H, m)<br>IR: 3300, 2930, 2860, 1680, 1642, 1598, 1530, 1510, 1270, 1245, 1178, 1015, 840 |
| 4 | [structure: 4-hydroxyphenyl-CH2-CH(CONH-cyclohexyl-CH2NH2)-CONH-C6H4-C(=O)CH3] | NMR: CD3OD, TMS δ 0.76–2.28(10H, m) 2.45(2H, d) 2.55(3H, s) 2.80–3.10(2H, m) 4.65(1H, m) 6.85(4H, dd) 7.76(4H, dd)<br>IR: 3300, 2925, 2860, 1640, 1590, 1510, 1260, 1175, 835 |

TABLE 1-continued
| | | | |
|---|---|---|---|
| 5 | 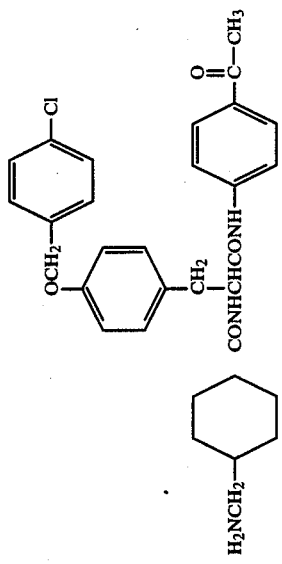 | IR:<br>3290, 2925, 2860, 1675,<br>1645, 1595, 1530, 1510,<br>1265, 1240, 1175, 1010,<br>810 | NMR:<br>50%CD₃OD—CDCl₃,TMS<br>δ 0.80–2.26(10H, m)<br>2.50–2.68(5H, broad)<br>(2.90–3.20(2H, m)<br>5.01(2H, s)<br>6.80–7.96(12H, m) |
| 6 | 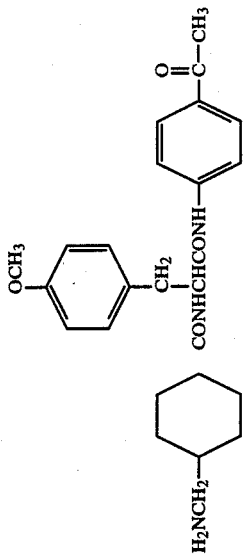 | IR:<br>3300, 2930, 2860, 1680,<br>1640, 1590, 1510, 1265,<br>1245, 1175, 1030, 830 | NMR:<br>50%CD₃OD—CDCl₃,TMS<br>δ 0.80–2.30(10H, m)<br>2.55(2H, d)<br>2.60(3H, s)<br>2.88–3.18(2H, m)<br>3.76(3H, s)<br>4.70(1H, m)<br>6.96(4H, dd)<br>7.78(4H, dd) |
| 7 | 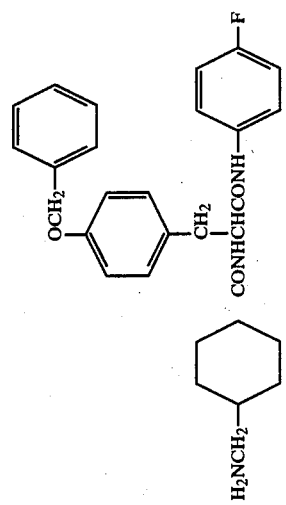 | IR:<br>3290, 2930, 2860, 1640,<br>1600, 1510, 1490, 1450,<br>1240, 1220, 1000 | NMR:<br>50%CD₃OD—CDCl₃,TMS<br>δ 0.80–2.25(10H, m)<br>2.55(2H, d)<br>3.04(2H, m)<br>4.70(1H, m)<br>5.04(2H, s)<br>6.84–7.50(13H, m) |

TABLE 1-continued
| | Structure | Data |
|---|---|---|
| 8 | 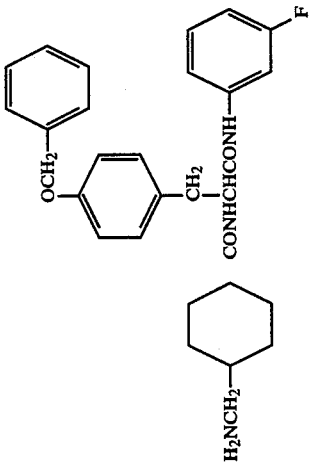 | IR: 3280, 2930, 2860, 1665, 1640, 1610, 1530, 1510, 1240, 1215, 1010, 830<br><br>NMR: 50%CD$_3$OD—CDCl$_3$,TMS<br>δ 0.8–2.25(10H, m)<br>2.55(2H, d)<br>2.90–3.20(2H, m)<br>5.06(2H, s)<br>6.88–7.48(13H, m) |
| 9 | 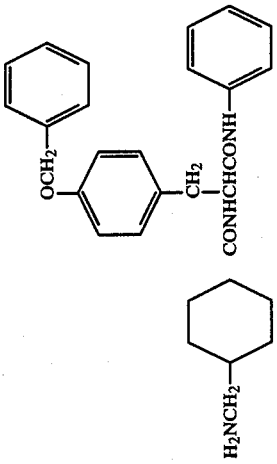 | MS: M/e 485, 467, 438, 393 365, 329, 282, 237, 197, 91<br><br>NMR: CDCl$_3$,TMS<br>δ 0.80–2.60(10H, m)<br>2.20–2.54(2H, m)<br>2.80–3.16(2H, m)<br>5.02(2H, s)<br>6.72–7.48(14H, m) |
| 10 |  | MS: M/e 493, 359, 343, 197, 134<br><br>NMR: CDCl$_3$—CD$_3$OD, TMS<br>δ 3.0–3.4(2H, m)<br>3.3(2H, s)<br>4.9–5.1(1H, m)<br>6.6–7.8(17H, m) |

TABLE 1-continued
| | | | |
|---|---|---|---|
| 11 | 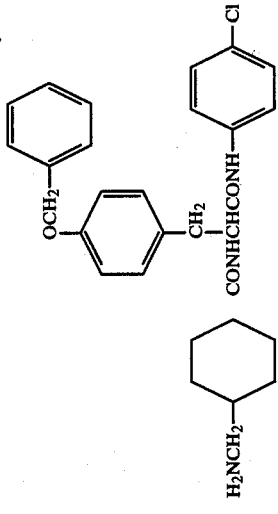 | MS:<br>M/e 519, 393, 363, 309,<br>281, 237, 226, 197, 127 | NMR:<br>(CD$_3$)$_2$SO,TMS<br>δ 0.70–2.68(10H, m)<br>3.52(1H, m)<br>5.04(2H, s)<br>6.76–7.72(13H, m) |
| 12 | 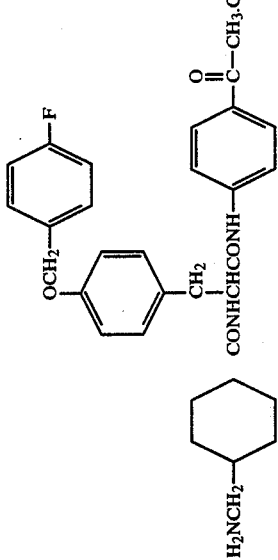 | IR:<br>3300, 2930, 2860, 1680,<br>1645, 1595, 1530,<br>1510, 1200, 1140 | |
| 13 | 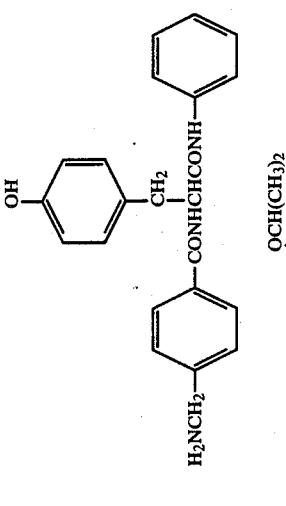 | MS:<br>M/e 389, 297, 239 | NMR:<br>CDCl$_3$—CD$_3$OD, TMS<br>δ 3.00–3.40(2H, m)<br>3.80(2H, s)<br>4.80–5.00(1H, m)<br>6.60–7.80(13H, m) |
| 14 | 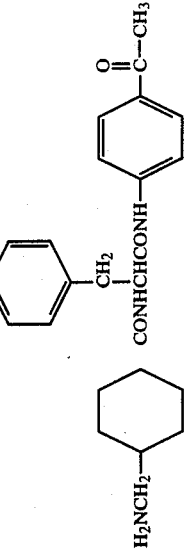 | IR:<br>3300, 2930, 2860, 1680,<br>1640, 1595, 1530, 1510,<br>1270, 1240, 1180, 1115,<br>950, 830 | NMR:<br>10%CD$_3$OD—CDCl$_3$,TMS<br>δ 0.8–2.20(10H, m)<br>1.30(6H, d)<br>2.52(2H, d)<br>2.58(3H, s)<br>2.85–3.16(2H, m)<br>4.46(1H, m)<br>4.70(1H, m)<br>6.93(4H, dd)<br>7.75(4H, dd) |

TABLE 1-continued
| | | |
|---|---|---|
| 15 | 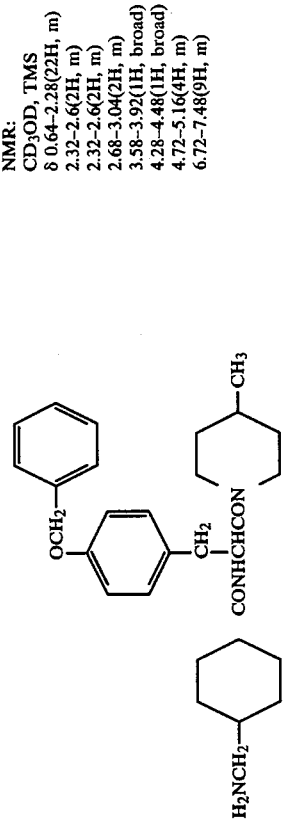 | NMR:<br>CD₃OD, TMS<br>δ 0.64–2.28(22H, m)<br>2.32–2.6(2H, m)<br>2.32–2.6(2H, m)<br>2.68–3.04(2H, m)<br>3.58–3.92(1H, broad)<br>4.28–4.48(1H, broad)<br>4.72–5.16(4H, m)<br>6.72–7.48(9H, m) |
| 16 | 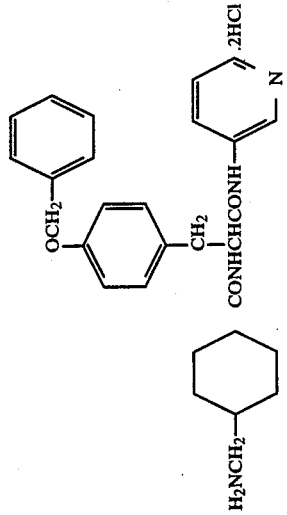 | IR:<br>3650–2250, 1700, 1640,<br>1610, 1545, 1510, 1450,<br>1380, 1240, 1010, 800<br><br>NMR:<br>CD₃OD, TMS<br>δ 0.90–2.00(9H, m)<br>2.20–2.40(1H, m)<br>2.78(2H, d)<br>2.90–8.20(2H, m)<br>4.68(1H, m)<br>5.02(2H, s)<br>6.84–7.40(9H, m)<br>8.00(1H, m)<br>8.44–8.60(2H, m)<br>9.32(1H, s) |
| 17 | 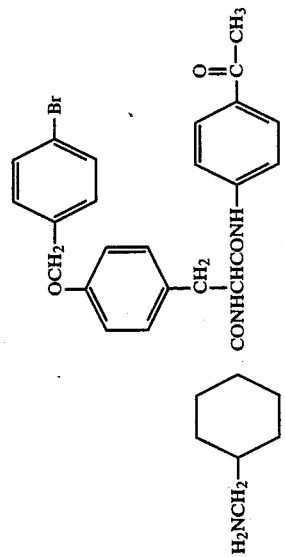 | IR:<br>3300, 2930, 2860, 1680,<br>1645, 1595, 1530, 1510,<br>1265, 1240, 1175, 820,<br>805<br><br>NMR:<br>(CD₃)₂SO, TMS<br>δ 0.70–2.20(10H, m)<br>2.38(2H, broad)<br>2.70–3.05(2H, m)<br>4.60(1H, broad)<br>5.02(2H, s)<br>6.85–7.92(12H, m) |

TABLE 1-continued
| | | IR: | NMR: |
|---|---|---|---|
| 18 | 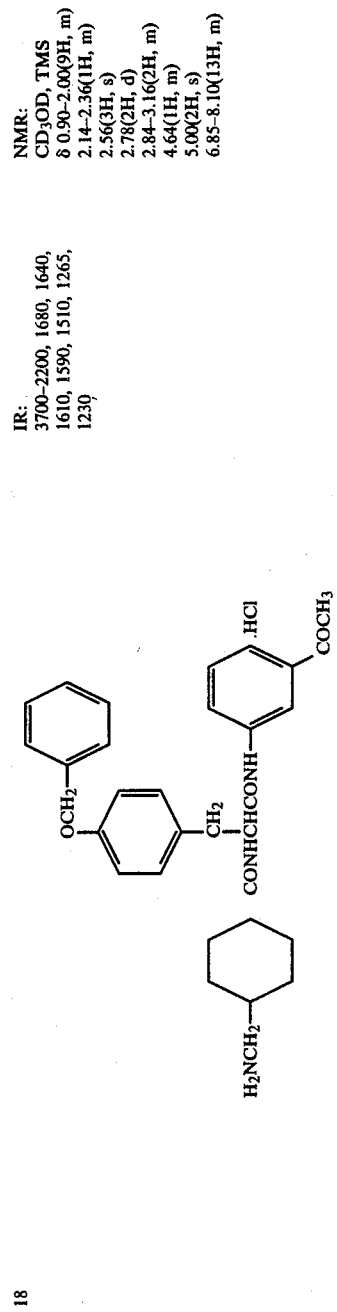 | 3700–2200, 1680, 1640, 1610, 1590, 1510, 1265, 1230 | CD₃OD, TMS δ 0.90–2.00(9H, m) 2.14–2.36(1H, m) 2.56(3H, s) 2.78(2H, d) 2.84–3.16(2H, m) 4.64(1H, m) 5.00(2H, s) 6.85–8.10(13H, m) |
| 19 | 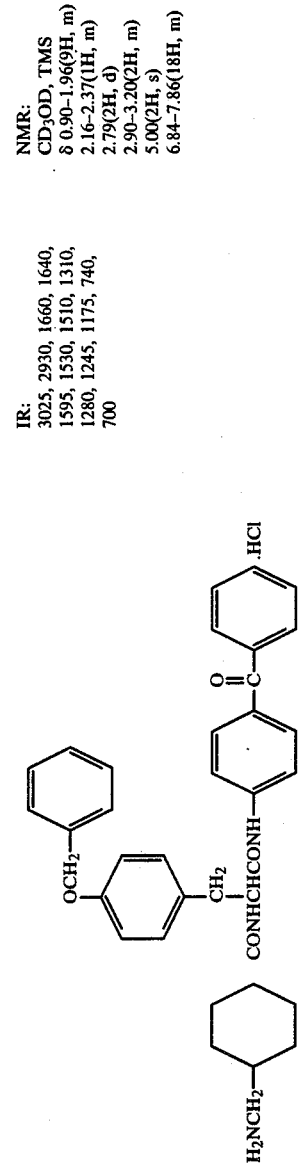 | 3025, 2930, 1660, 1640, 1595, 1530, 1510, 1310, 1280, 1245, 1175, 740, 700 | CD₃OD, TMS δ 0.90–1.96(9H, m) 2.16–2.37(1H, m) 2.79(2H, d) 2.90–3.20(2H, m) 5.00(2H, s) 6.84–7.86(18H, m) |
| 20 | 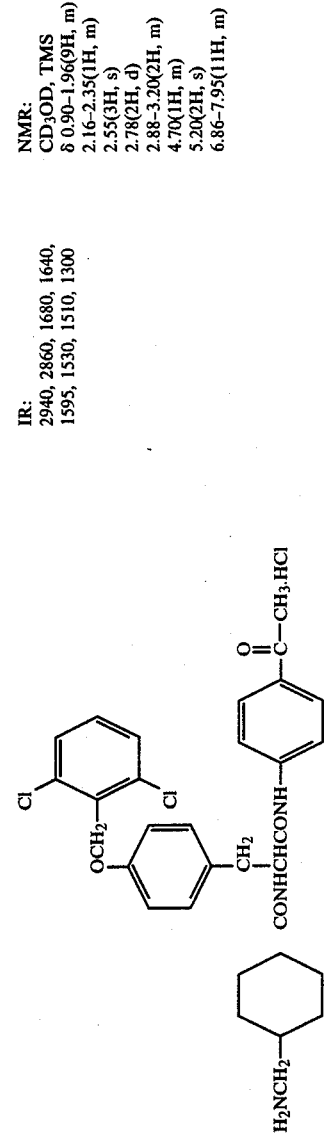 | 2940, 2860, 1680, 1640, 1595, 1530, 1510, 1300 | CD₃OD, TMS δ 0.90–1.96(9H, m) 2.16–2.35(1H, m) 2.55(3H, s) 2.78(2H, d) 2.88–3.20(2H, m) 4.70(1H, m) 5.20(2H, s) 6.86–7.95(11H, m) |

TABLE 1-continued
| No. | Structure | Data |
|---|---|---|
| 21 | 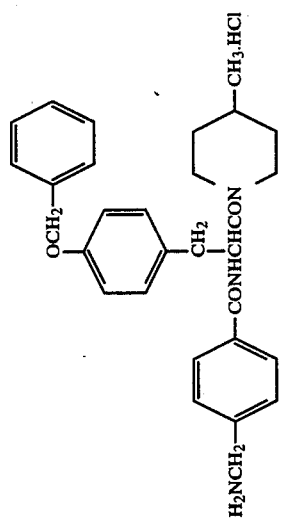 | MS: M/e 485, 467, 432, 359, 335, 288, 244, 197, 155, 134, 91<br>NMR: (CD$_3$)$_2$SO, TMS δ 0.76–2.68(11H, m) 3.50(1H, s) 4.08(2H, s) 5.04(2H, s) 6.88–7.92(13H, m) |
| 22 | 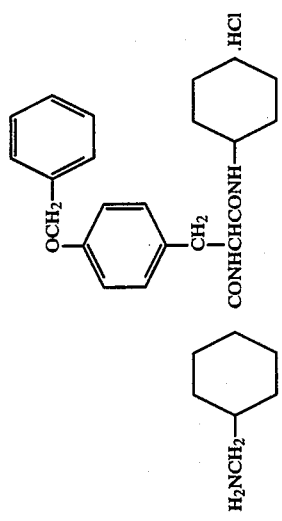 | IR: 3300, 2930, 2860, 1640, 1545, 1570, 1240, 1220<br>NMR: CD$_3$OD, TMS δ 0.80–1.90(19H, m) 2.08–2.26(1H, m) 2.77(2H, d) 2.80–3.10(3H, m) 4.45(1H, m) 5.02(2H, s) 6.84–7.40(9H, m) |
| 23 | 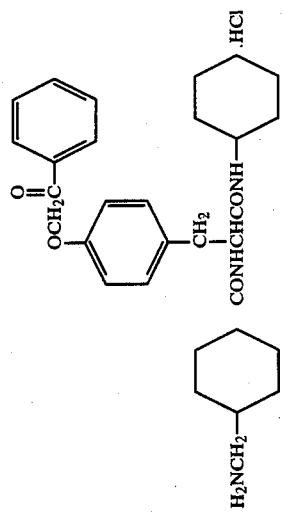 | IR: 3280, 2930, 2860, 1705, 1645, 1630, 1530, 1510, 1450, 1270, 1250, 1230, 1210, 1180, 980, 760<br>NMR: CD$_3$OD, TMS δ 0.9–1.95(19H, m) 2.1–2.30(1H, m) 2.78(2H, d) 2.80–3.20(3H, m) 4.50(1H, m) 5.40(2H, s) 6.85–8.04(9H, m) |

TABLE 1-continued

| | | |
|---|---|---|
| 24 | [structure: phenyl-OCH2-C6H4-CH2-CH(NHCOCH(CH2-cyclohexyl)NH2)-CONHCH2CH2OCH3·HCl] | NMR:<br>CD3OD, TMS<br>δ 0.82–2.33(10H, m)<br>2.72–3.50(6H, m)<br>3.30(3H, s)<br>4.50–4.62(1H, m)<br>5.02(2H, s)<br>6.90(2H, d)<br>7.14(2H, d)<br>7.30–7.48(5H, m) |
| 25 | [structure: phenyl-OCH2-C6H4-CH2-CH(NHCOCH(CH2-cyclohexyl)NH2)-CONH-C6H4-C(O)CH3·HCl] (D) | NMR:<br>CD3OD, TMS<br>δ 0.9–2.0(10H, m)<br>2.1–3.1(2H, m)<br>2.55(3H, s)<br>2.75(2H, d)<br>3.1–3.2(2H, m)<br>4.7(1H, broad)<br>5.0(2H, s)<br>6.9(2H, m)<br>7.1–8.0(13H, m) |
| 26 | [structure: phenyl-OCH2-C6H4-CH2-CH(NHCOCH(CH2-cyclohexyl)NH2)-CONH-C6H4-CH3·HCl] | MS:<br>M/e 499, 481, 393, 343,<br>237, 197, 107, 91<br><br>NMR:<br>CD3OD, TMS<br>δ 0.8–2.12(12H, m)<br>2.28(3H, s)<br>2.72–2.84(2H, m)<br>5.02(2H, s)<br>6.80–7.40(13H, m) |

TABLE 1-continued
| | | |
|---|---|---|
| 27 | 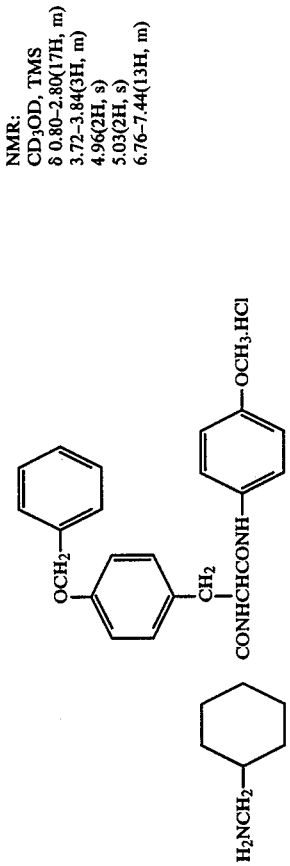 | NMR: CD₃OD, TMS δ 0.80–2.80(17H, m) 3.72–3.84(3H, m) 4.96(2H, s) 5.03(2H, s) 6.76–7.44(13H, m) |
| 28 | 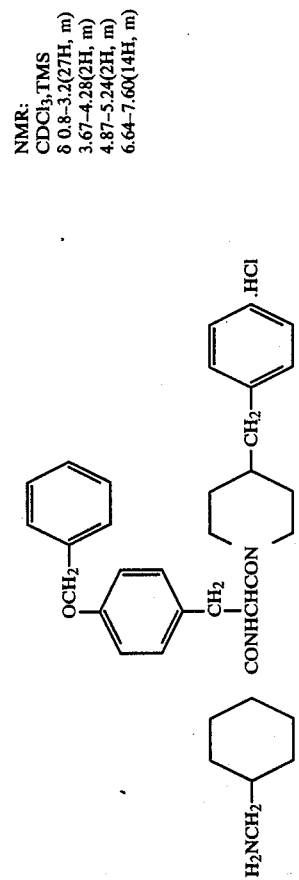 | NMR: CDCl₃, TMS δ 0.8–3.2(27H, m) 3.67–4.28(2H, m) 4.87–5.24(2H, m) 6.64–7.60(14H, m) |
| 29 | 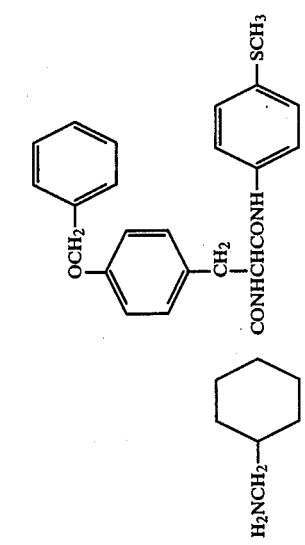 | IR: 3300, 2925, 2860, 1665, 1640, 1580, 1530, 1505, 1495, 1235<br><br>NMR: (CD₃)₂SO, TMS δ 0.70–1.84(9H, m) 2.00–2.20(1H, m) 2.44(3H, s) 2.70–3.00(2H, m) 4.66(1H, m) 5.04(2H, s) 6.84–7.56(13H, m) |

TABLE 1-continued

| # | Structure | Spectral data |
|---|---|---|
| 30 | Compound with OCH2CO-phenyl, 4-substituted benzyl with CH2 linker, CONHCHCONH, cyclohexyl, H2NCH2, and 4-acetyl (CH3-C=O) phenyl group | NMR: CD3OD, TMS δ 0.80–1.96(9H, m) 2.10–2.30(1H, m) 2.52(2H, d) 2.56(3H, s) 3.04(2H, m) 4.07(1H, m) 5.40(2H, s) 6.85–8.04(13H, m) |
| 31 | 4-NO2-benzyl, CH2, CONHCHCONH (DL), cyclohexyl, H2NCH2, benzoyl-phenyl·HCl | IR: 3400, 2940, 1640, 1600, 1520, 1345, 1280, 1180 |
| 32 | OCH2-phenyl, CH2, CONHCHCONH, cyclohexyl, H2NCH2, 4-(CH3CH2C=O)phenyl | IR: 3300, 2940, 1650, 1610, 1505, 1240, 1180 |
| 33 | 4-NH2-benzyl, CH2, CONHCHCONH (DL), cyclohexyl, H2NCH2, 4-benzoyl-phenyl | IR: 3350, 2940, 1650, 1600, 1520, 1280, 1180 NMR: CDCl3—CD3OD, TMS δ 0.90–2.20(10H, m) 2.75(2H, d) 3.60–3.70(2H, m) 4.85(1H, t) 7.30–7.90(11H, m) 8.15(2H, d) |

TABLE 1-continued
| | | |
|---|---|---|
| 34 | 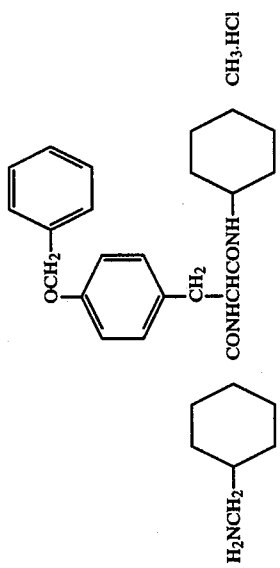 | NMR:<br>CD₃OD, TMS<br>δ 0.84–1.92(21H, broad)<br>2.08–2.28(1H, broad)<br>2.68–2.82(2H, m)<br>3.08–3.26(2H, m)<br>3.60–3.68(1H, broad)<br>4.32–4.62(2H, broad)<br>4.62–4.80(3H, m)<br>4.92(1H, s)<br>5.04(2H, s)<br>6.80–7.44(9H, m) |
| 35 | 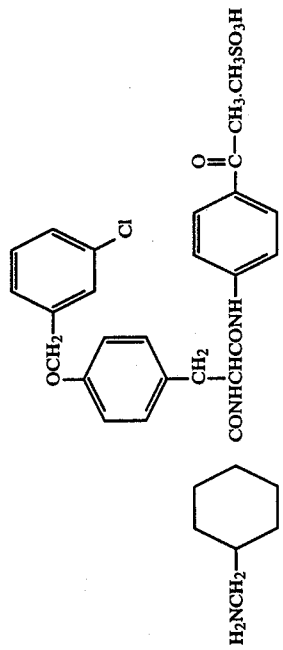 | NMR:<br>CD₃OD, TMS<br>δ 0.88–2.36(10H, m)<br>2.56(3H, s)<br>2.72(3H, s)<br>2.76–3.22(4H, m)<br>4.64–4.76(1H, m)<br>5.02(2H, s)<br>6.84–7.96(12H, m) |
| 36 | 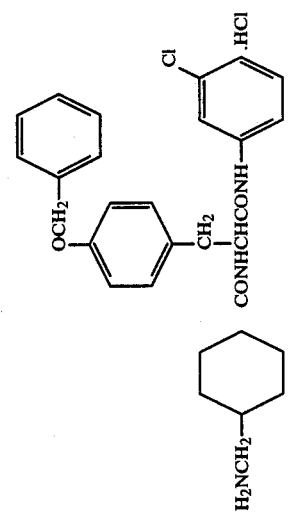 | NMR:<br>CD₃OD, TMS<br>δ 0.88–1.64(10H, m)<br>1.66–2.32(2H, broad)<br>2.60–2.82(2H, m)<br>5.03(2H, s)<br>6.80–7.72(13H, m) |

TABLE 1-continued
| 37 | 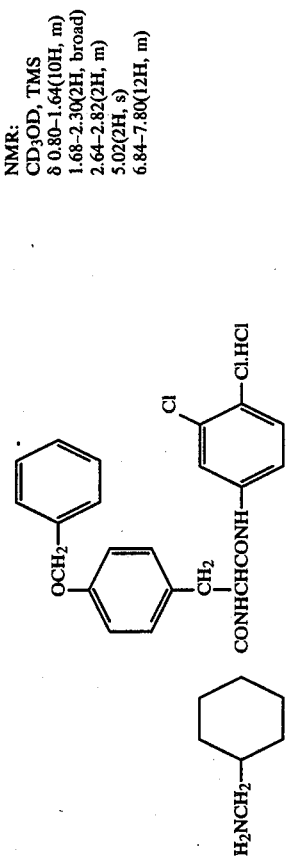 | NMR:<br>CD₃OD, TMS<br>δ 0.80–1.64(10H, m)<br>1.68–2.30(2H, broad)<br>2.64–2.82(2H, m)<br>5.02(2H, s)<br>6.84–7.80(12H, m) |
|---|---|---|
| 38 | 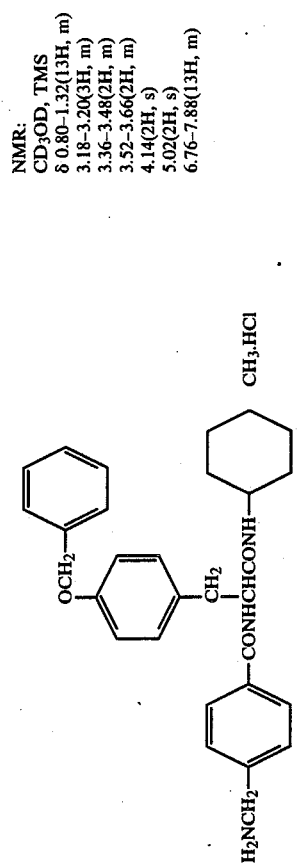 | NMR:<br>CD₃OD, TMS<br>δ 0.80–1.32(13H, m)<br>3.18–3.20(3H, m)<br>3.36–3.48(2H, m)<br>3.52–3.66(2H, m)<br>4.14(2H, s)<br>5.02(2H, s)<br>6.76–7.88(13H, m) |
| 39 | 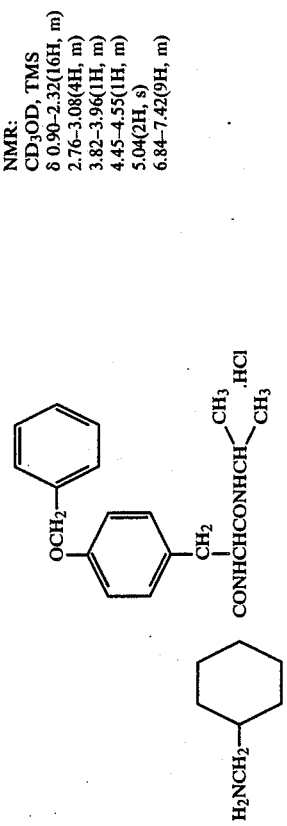 | NMR:<br>CD₃OD, TMS<br>δ 0.90–2.32(16H, m)<br>2.76–3.08(4H, m)<br>3.82–3.96(1H, m)<br>4.45–4.55(1H, m)<br>5.04(2H, s)<br>6.84–7.42(9H, m) |

| | | |
|---|---|---|
| 40 | 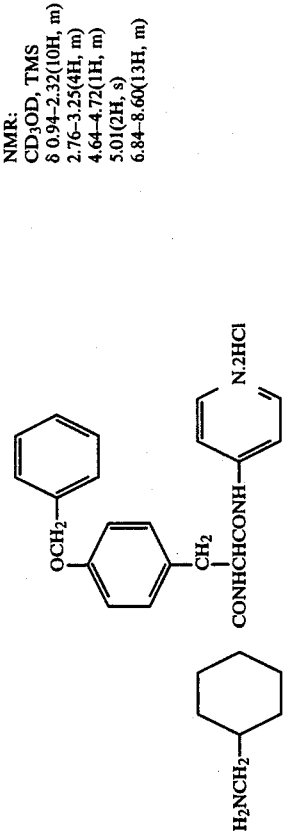 | NMR:<br>CD$_3$OD, TMS<br>δ 0.94-2.32(10H, m)<br>2.76-3.25(4H, m)<br>4.64-4.72(1H, m)<br>5.01(2H, s)<br>6.84-8.60(13H, m) |
| 41 | 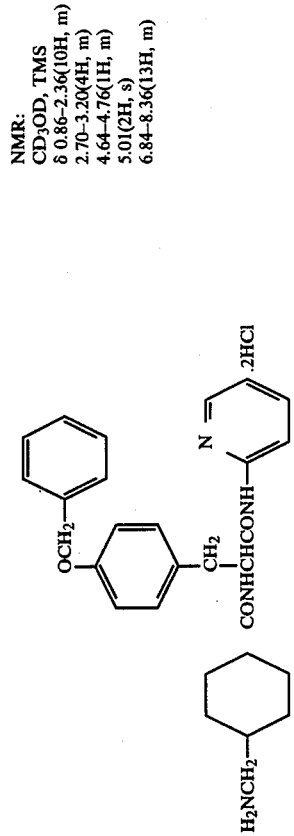 | NMR:<br>CD$_3$OD, TMS<br>δ 0.86-2.36(10H, m)<br>2.70-3.20(4H, m)<br>4.64-4.76(1H, m)<br>5.01(2H, s)<br>6.84-8.36(13H, m) |
| 42 | 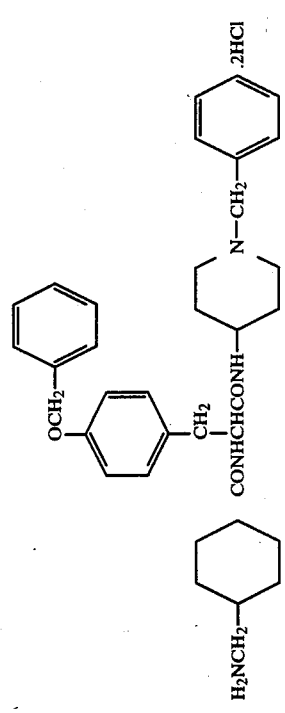 | NMR:<br>CD$_3$OD, TMS<br>δ 0.86-2.28(14H, m)<br>2.70-3.50(9H, m)<br>4.30(2H, s)<br>4.50(1H, m)<br>5.01(2H, s)<br>6.84-7.60(14H, m) |

TABLE 1-continued
| | | |
|---|---|---|
| 43 | 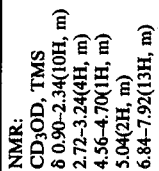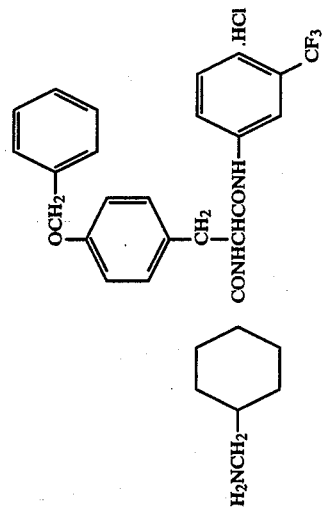 | NMR:<br>CD$_3$OD, TMS<br>δ 0.90–2.34(10H, m)<br>2.72–3.24(4H, m)<br>4.56–4.70(1H, m)<br>5.04(2H, m)<br>6.84–7.92(13H, m) |
| 44 | 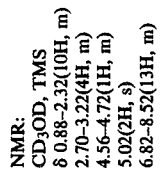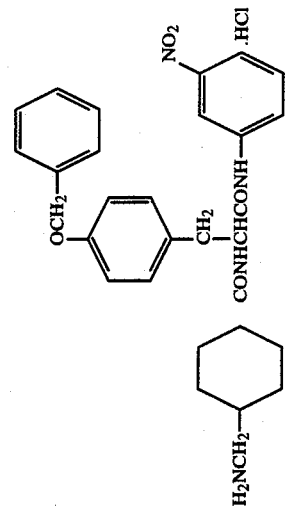 | NMR:<br>CD$_3$OD, TMS<br>δ 0.88–2.32(10H, m)<br>2.70–3.22(4H, m)<br>4.56–4.72(1H, m)<br>5.02(2H, s)<br>6.82–8.52(13H, m) |
| 45 | 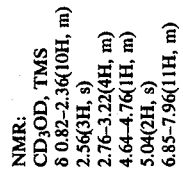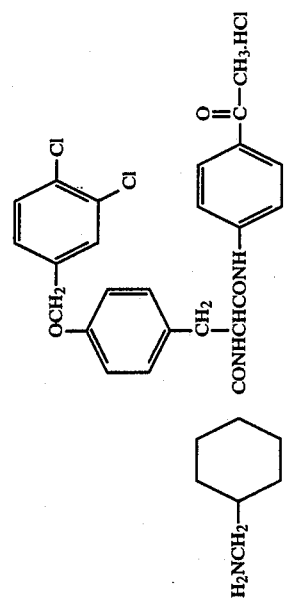 | NMR:<br>CD$_3$OD, TMS<br>δ 0.82–2.36(10H, m)<br>2.56(3H, s)<br>2.76–3.22(4H, m)<br>4.64–4.76(1H, m)<br>5.04(2H, s)<br>6.85–7.96(11H, m) |
| 46 | 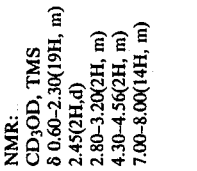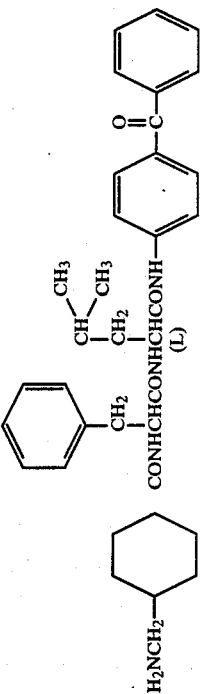 | NMR:<br>CD$_3$OD, TMS<br>δ 0.60–2.30(19H, m)<br>2.45(2H, d)<br>2.80–3.20(2H, m)<br>4.30–4.56(2H, m)<br>7.00–8.00(14H, m) |

| 47 | 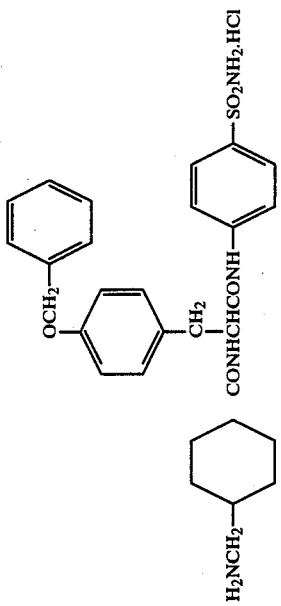 | NMR:<br>CD₃OD, TMS<br>δ 0.68–2.40(17H,broad)<br>2.06–2.40(1H,broad)<br>2.44–2.96(2H,broad)<br>3.66(1H,s)<br>5.02(2H,s)<br>6.62–8.24(13H,m) |
| --- | --- | --- |
| 48 | 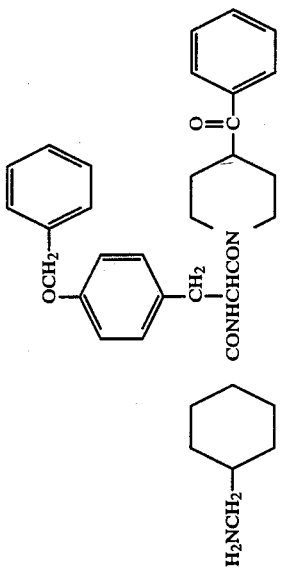 | MS:<br>M/e 581,553,425,393,<br>365,337,334,309,<br>282,197,91 |
| 49 | 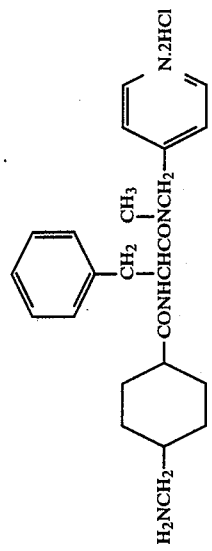 | IR:<br>3430,3050,2930,1640,<br>1510,1450,1250,700 |
(additional NMR for 48):
NMR:
CDCl₃, TMS
δ 0.80–2.20(14H,m)
2.55(2H,d)
2.68–3.48(7H,m)
3.78(1H,t)
4.50(1H,t)
4.88–5.26(2H,m)
6.28–8.02(14H,m)

-continued
| | | |
|---|---|---|
| 50 | 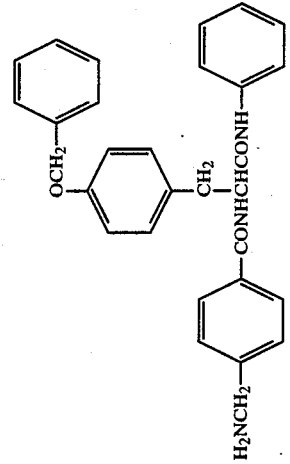 | IR:<br>3300,1640,1510,1240 |
| 51 | 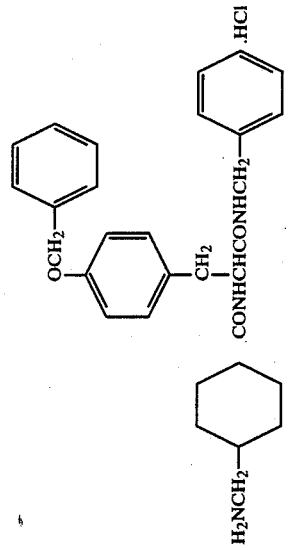 | NMR:<br>CD$_3$OD, TMS<br>δ 0.80–2.32(10H,m)<br>2.62–2.92(2H,m)<br>3.64(2H,s)<br>4.20–4.36(1H,m)<br>4.44–4.64(1H,broad)<br>5.04(2H,s)<br>6.80–7.48(14H,m) |
| 52 | 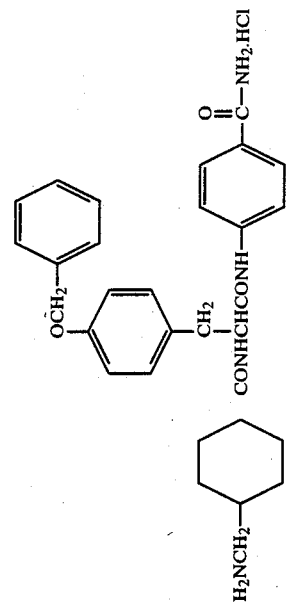 | NMR:<br>CD$_3$OD, TMS<br>δ 0.91–2.36(10H,m)<br>2.72–3.28(4H,m)<br>4.56–4.75(1H,broad)<br>5.02(2H,s)<br>6.70–8.08(13H,m) |

| | | |
|---|---|---|
| 53 | 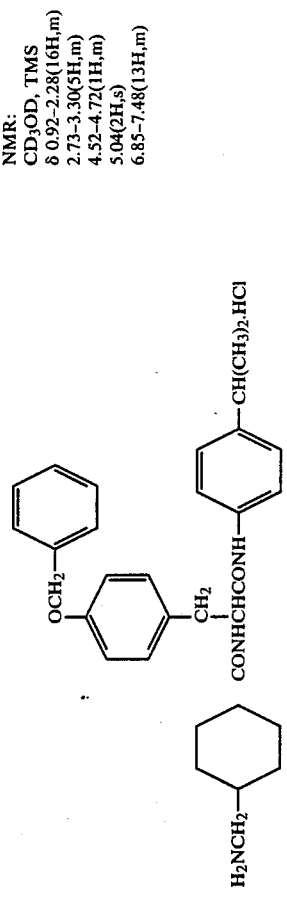 | NMR:<br>CD₃OD, TMS<br>δ 0.92–2.28(16H,m)<br>2.73–3.30(5H,m)<br>4.52–4.72(1H,m)<br>5.04(2H,s)<br>6.85–7.48(13H,m) |
| 54 | 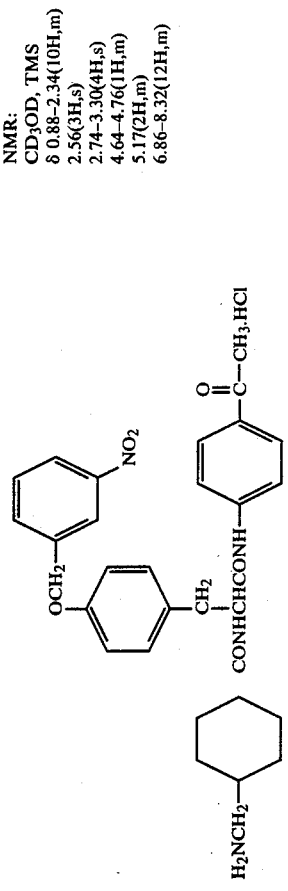 | NMR:<br>CD₃OD, TMS<br>δ 0.88–2.34(10H,m)<br>2.56(3H,s)<br>2.74–3.30(4H,s)<br>4.64–4.76(1H,m)<br>5.17(2H,s)<br>6.86–8.32(12H,m) |
| 55 | 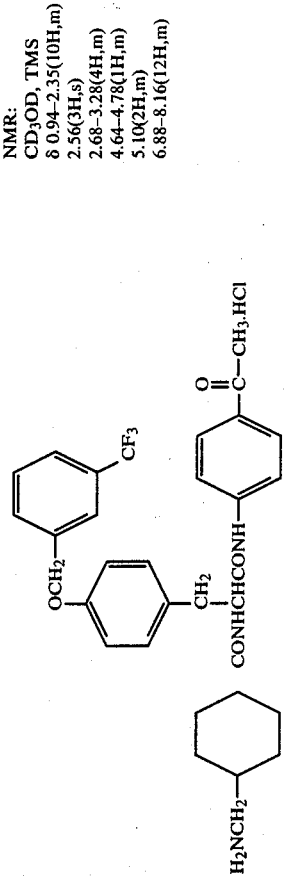 | NMR:<br>CD₃OD, TMS<br>δ 0.94–2.35(10H,m)<br>2.56(3H,s)<br>2.68–3.28(4H,m)<br>4.64–4.78(1H,m)<br>5.10(2H,s)<br>6.88–8.16(12H,m) |

-continued
| 56 | 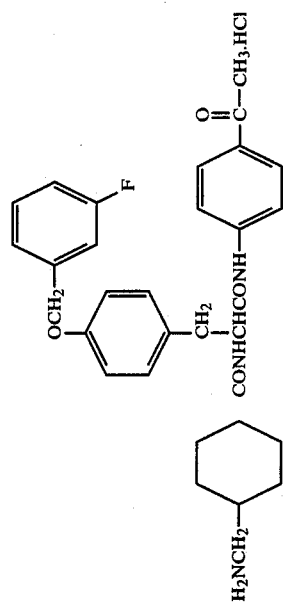 | NMR: CD₃OD, TMS δ 0.92–2.36(10H,m) 2.55(3H,s) 2.72–3.24(4H,m) 4.56–4.78(1H,m) 5.05(2H,s) 6.85–8.18(12H,m) |
| 57 | 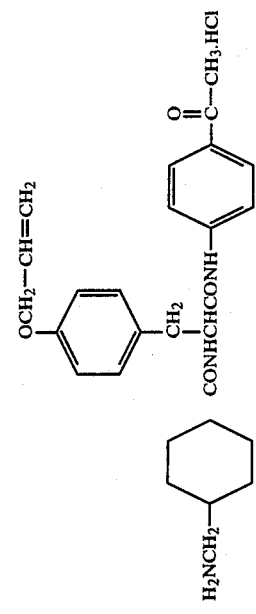 | NMR: CD₃OD, TMS δ 0.92–2.36(10H,m) 2.56(3H,s) 2.76–3.25(4H,m) 4.44–4.52(2H,m) 4.64–4.77(1H,m) 5.16–5.41(2H,m) 5.90–6.10(1H,m) 6.78–7.96(8H,m) |
| 58 | 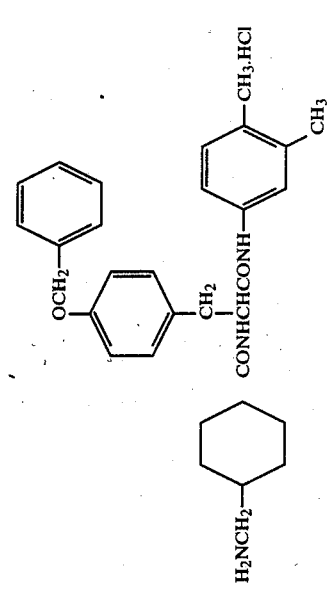 | NMR: CD₃OD, TMS δ 0.80–2.32(16H,m) 2.68–3.20(4H,m) 5.03(2H,s) 6.70–7.48(12H,m) |

-continued
| | | |
|---|---|---|
| 59 | 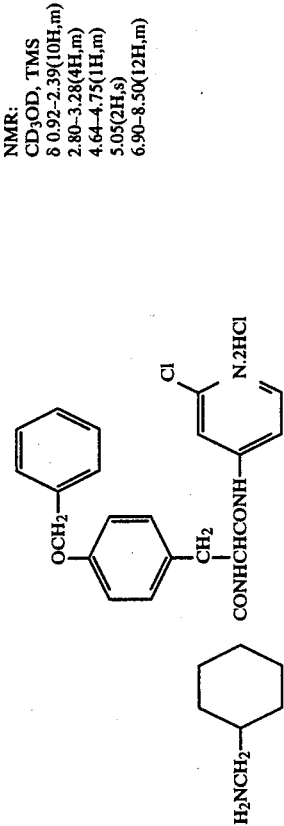 | NMR:<br>CD₃OD, TMS<br>δ 0.92–2.39(10H,m)<br>2.80–3.28(4H,m)<br>4.64–4.75(1H,m)<br>5.05(2H,s)<br>6.90–8.50(12H,m) |
| 60 | 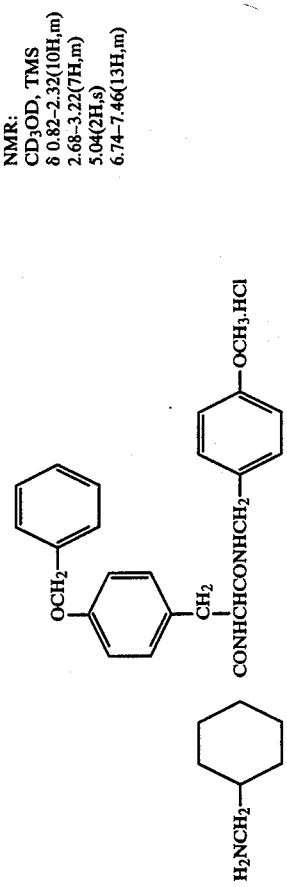 | NMR:<br>CD₃OD, TMS<br>δ 0.82–2.32(10H,m)<br>2.68–3.22(7H,m)<br>5.04(2H,s)<br>6.74–7.46(13H,m) |
| 61 | 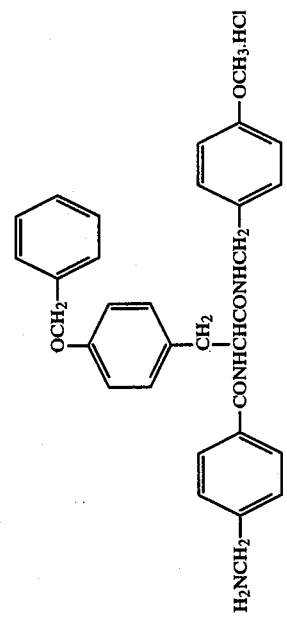 | MS:<br>M/e 523,373,282,236,<br>197,137<br><br>IR:<br>3320,1635,1510,1245 |

| | | |
|---|---|---|
| 62 | 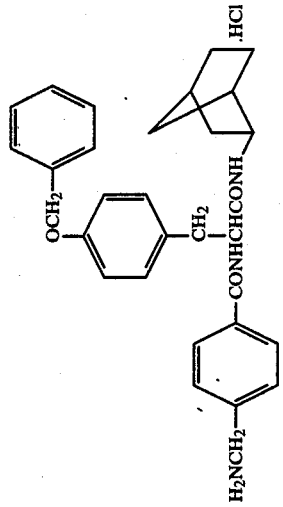 | MS:<br>M/e 497,432,387,359,<br>347,282,256,237,<br>226,210,197,134,<br>110,91 |
| 63 | 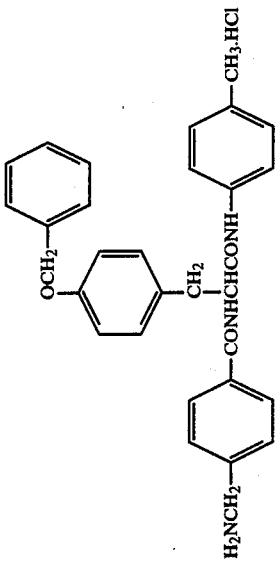 | MS:<br>M/e 493,343,236,197,<br>134<br>IR:<br>1640,1510,1240,815<br><br>NMR:<br>CD$_3$OD, TMS<br>δ 2.29(3H,s)<br>3.0–3.20(2H,m)<br>4.16(2H,s)<br>3.90–4.10(3H,m)<br>6.80–7.90(17H,m) |
| 64 | 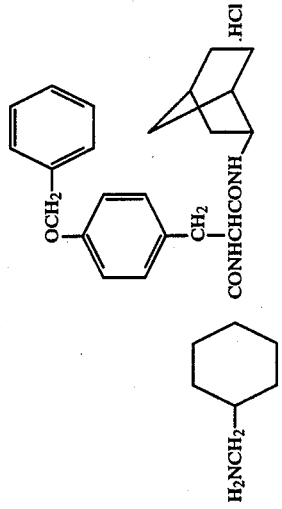 | MS:<br>M/e 503,438,393,365,<br>347,256,237,226,<br>210,197,140,112,<br>110,91 |

-continued
| | | |
|---|---|---|
| 65 | 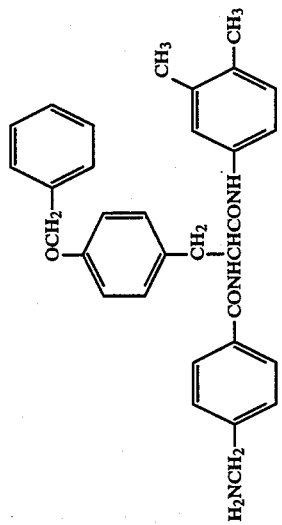 | MS:<br>M/e 507,357,310,237,<br>197,134<br>IR:<br>3300,1635,1510,1240 | NMR:<br>CD₃OD—CDCl₃, TMS<br>δ 2.2(6H,s)<br>3.0–3.20(2H,m)<br>3.83(2H,s)<br>4.80–5.10(3H,m)<br>6.80–7.80(16H,m) |
| 66 | 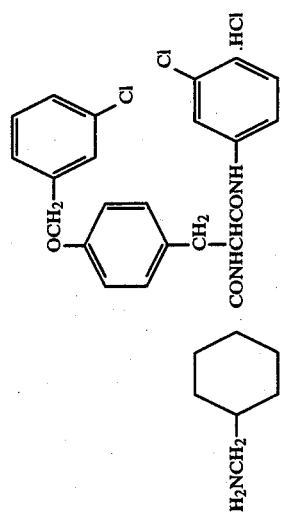 | | NMR:<br>CD₃OD, TMS<br>δ 0.95–2.36(10H,m)<br>2.70–3.25(4H,m)<br>4.65–4.75(1H,m)<br>5.00(2H,s)<br>6.88–7.72(12H,m) |
| 67 | 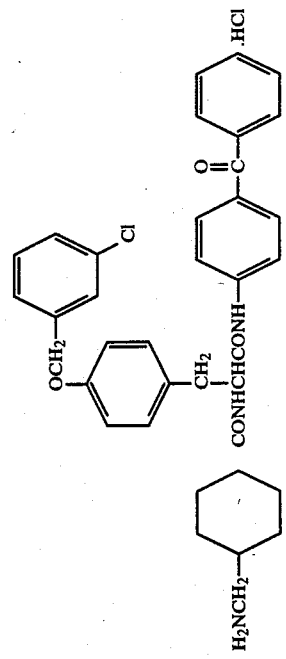 | | NMR:<br>CD₃OD, TMS<br>δ 0.94–2.28(10H,m)<br>2.76–3.24(4H,m)<br>4.70–4.80(1H,m)<br>5.00(2H,s)<br>6.84–7.80(17H,s) |

-continued
| | | |
|---|---|---|
| 68 | 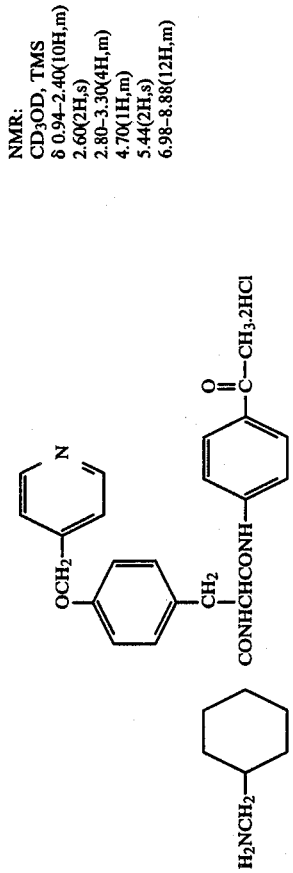 | NMR:<br>CD₃OD, TMS<br>δ 0.94–2.40(10H,m)<br>2.60(2H,s)<br>2.80–3.30(4H,m)<br>4.70(1H,m)<br>5.44(2H,s)<br>6.98–8.88(12H,m) |
| 69 | 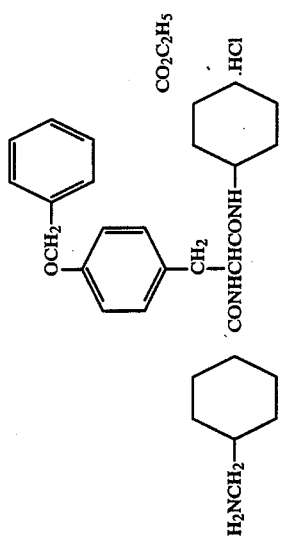 | NMR:<br>CD₃OD, TMS<br>δ 0.90–2.50(22H,m)<br>2.72–3.10(5H,m)<br>4.04–4.16(2H,m)<br>4.42–4.50(1H,m)<br>5.04(2H,m)<br>6.85–7.44(9H,m) |
| 70 | 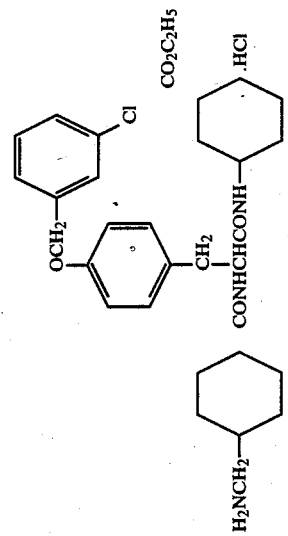 | NMR:<br>CD₃OD, TMS<br>δ 0.92–2.45(22H,m)<br>2.76–3.10(5H,m)<br>4.03–4.16(2H,m)<br>4.41–4.52(1H,m)<br>5.04(2H,m)<br>6.85–7.44(8H,m) |

-continued
| | | |
|---|---|---|
| 71 | 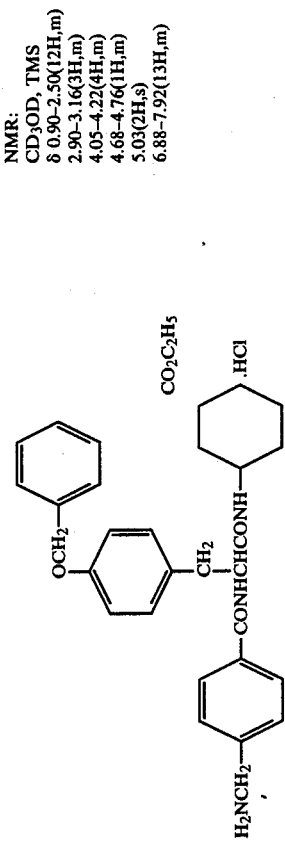 | NMR:<br>CD$_3$OD, TMS<br>δ 0.90–2.50(12H,m)<br>2.90–3.16(3H,m)<br>4.05–4.22(4H,m)<br>4.68–4.76(1H,m)<br>5.03(2H,s)<br>6.88–7.92(13H,m) | |
| 72 | 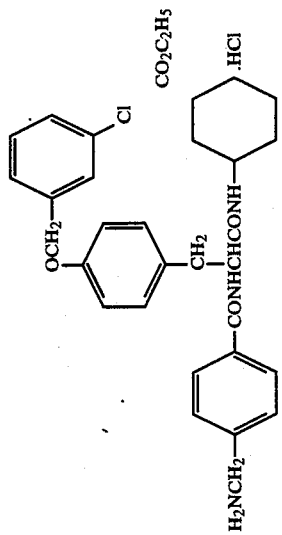 | NMR:<br>CD$_3$OD, TMS<br>δ 0.92–2.50(12H,m)<br>2.91–3.15(3H,m)<br>4.02–4.20(4H,m)<br>4.65–4.75(1H,m)<br>5.04(2H,s)<br>6.85–7.88(12H,m) | |
| 73 | 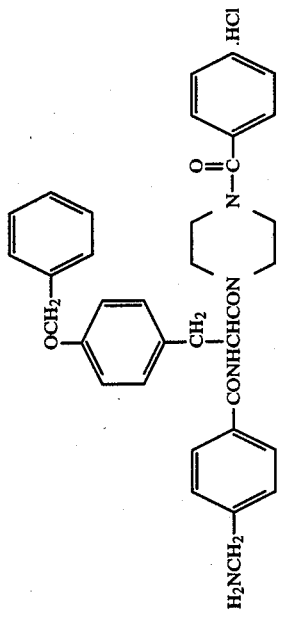 | MS:<br>M/e 426,254,197,134 | IR:<br>1640,1515,1250,710 |

| | | |
|---|---|---|
| 74 | 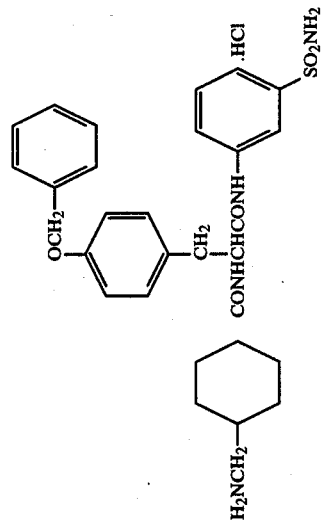 | NMR:<br>CD₃OD, TMS<br>$\delta$ 0.84–2.34(10H,m)<br>2.60–3.22(4H,m)<br>4.60–4.73(1H,m)<br>5.01(2H,s)<br>6.80–8.16(13H,m) |
| 75 | 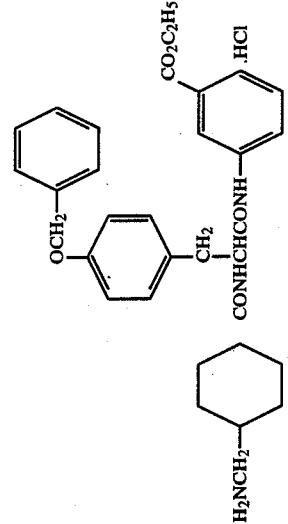 | NMR:<br>CD₃OD, TMS<br>$\delta$ 0.94–2.36(13H,m)<br>2.74–3.24(4H,m)<br>4.32–4.40(2H,m)<br>4.68–4.76(1H,m)<br>5.00(2H,s)<br>6.84–8.20(13H,m) |
| 76 | 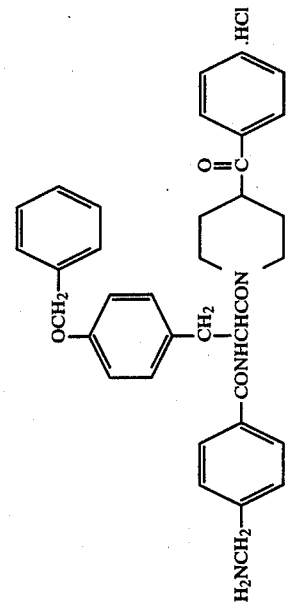 | MS:<br>M/e 575,442,425,410,<br>326,291<br><br>IR:<br>1620,1510,1240,695 |

-continued
| | | |
|---|---|---|
| 77 | 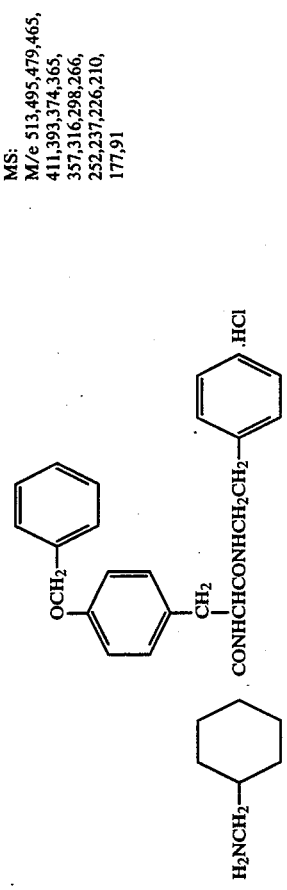 MS: M/e 513,495,479,465, 411,393,374,365, 357,316,298,266, 252,237,226,210, 177,91 | |
| 78 | 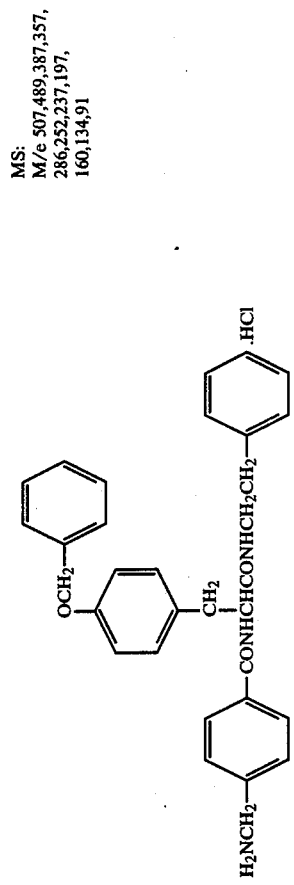 MS: M/e 507,489,387,357, 286,252,237,197, 160,134,91 | |
| 79 | 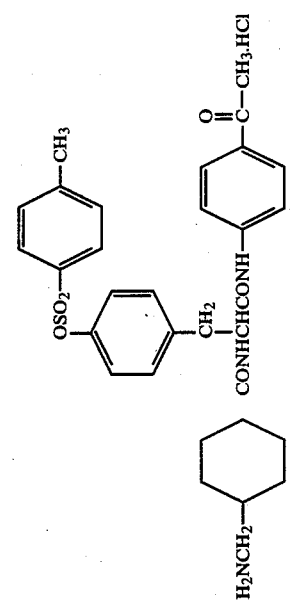 IR: 3400,2940,1650,1600, 1500,1365,1270,1180, 870 | |

-continued
80 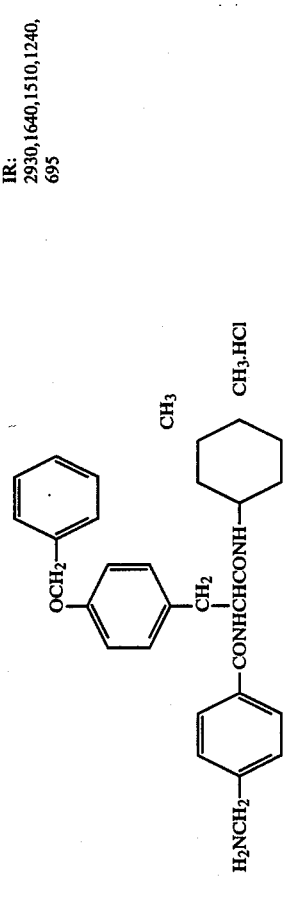
IR:
2930,1640,1510,1240,
695
81 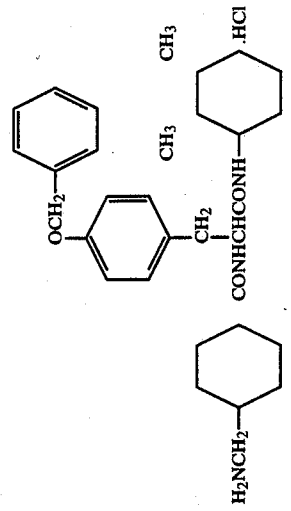
MS:
M/e 519,501,393,379,
363,282,272,253,
237,226,210,183,
91
82 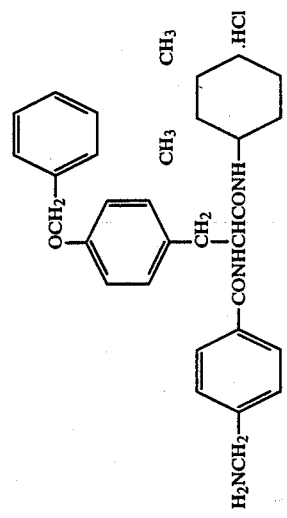
MS:
M/e 424,387,359,343,
297,226,197,134,
93

-continued
| | | |
|---|---|---|
| 83 | 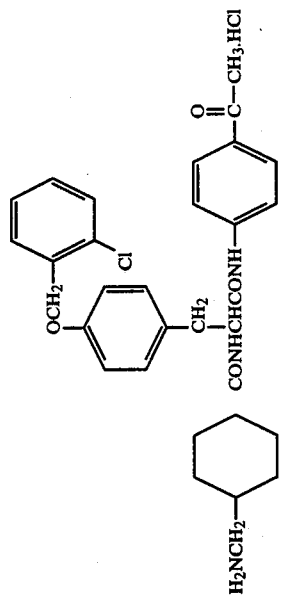 | NMR:<br>CD₃OD, TMS<br>$\delta$ 0.90–2.34(10H,m)<br>2.56(3H,s)<br>2.70–3.20(4H,m)<br>4.68–4.76(1H,m)<br>5.08(2H,s)<br>6.84–7.97(12H,m) |
| 84 | 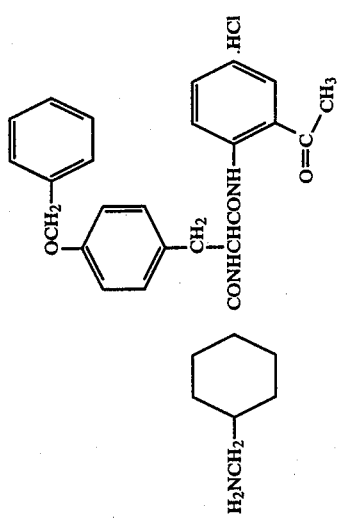 | NMR:<br>CD₃OD, TMS<br>$\delta$ 0.91–3.20(17H,m)<br>4.52–4.64(1H,m)<br>5.00(2H,s)<br>6.82–7.70(13H,m) |
| 85 | 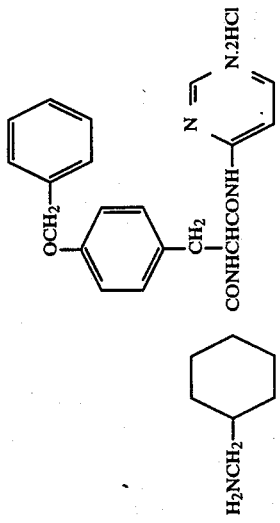 | NMR:<br>CD₃OD, TMS<br>$\delta$ 0.92–2.36(10H,m)<br>2.76–3.22(4H,m)<br>4.72–4.86(1H,m)<br>5.03(2H,s)<br>6.77–9.16(12H,m) |

| | | |
|---|---|---|
| 86 | 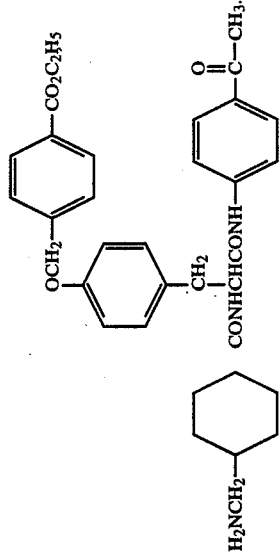 | NMR:<br>CD$_3$OD, TMS<br>δ 0.90–2.35(13H,m)<br>2.58(3H,s)<br>2.70–3.30(4H,m)<br>4.32–4.44(2H,m)<br>4.70(1H,m)<br>5.15(2H,s)<br>6.90–8.08(12H,m) |
| 87 | 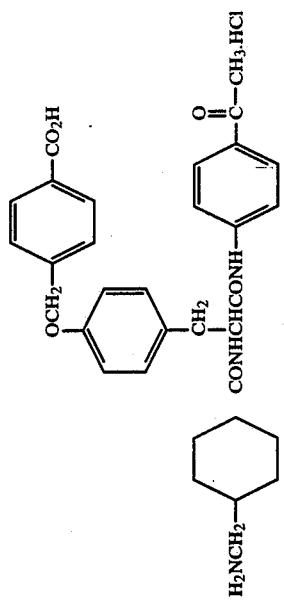 | NMR:<br>CD$_3$OD, TMS<br>δ 0.96–2.32(10H,m)<br>2.56(3H,s)<br>2.99–2.70(2H,m)<br>2.70–3.20(2H,m)<br>4.60–4.72(1H,m)<br>5.12(2H,s)<br>6.80–8.02(12H,m) |
| 88 | 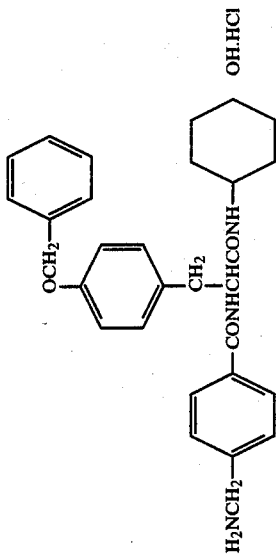 | MS:<br>M/e 387,351,134<br><br>IR:<br>3360,2950,1640,1515,<br>1240 |

-continued
| | | |
|---|---|---|
| 89 | 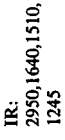 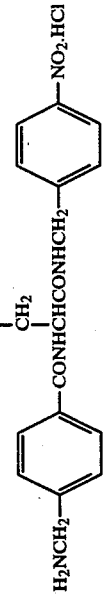 | IR: 2950,1640,1510,1345, 1245 |
| 90 | 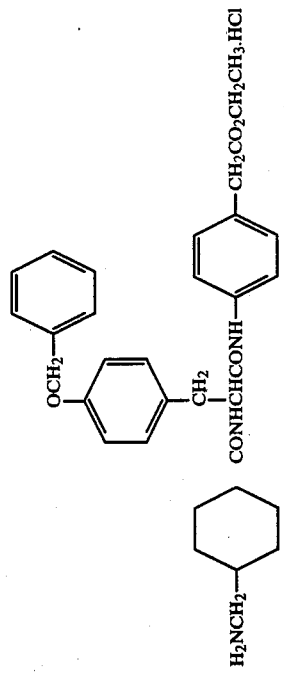 | MS: M/e 571,415,374,237, 226,218,197,179, 106,91 |
| 91 | 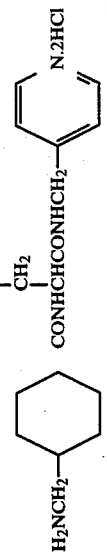 | IR: 3430,3300,3050,2840, 1735,1640,1610,1515, 1240,1180,1025<br><br>MS: M/e 500,393,362,344, 226,197,91 |

| 92 | 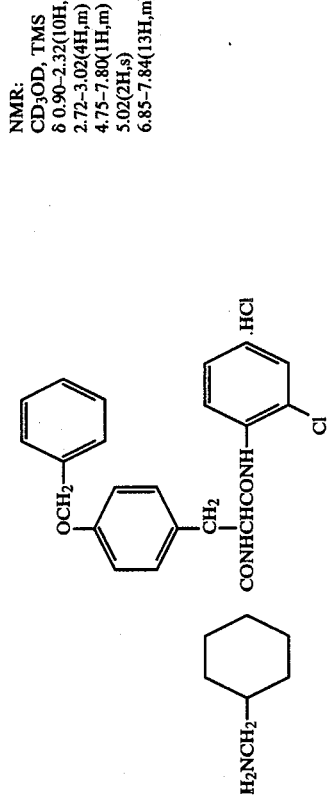 | NMR:<br>CD₃OD, TMS<br>δ 0.90–2.32(10H,m)<br>2.72–3.02(4H,m)<br>4.75–7.80(1H,m)<br>5.02(2H,s)<br>6.85–7.84(13H,m) |
|---|---|---|
| 93 | 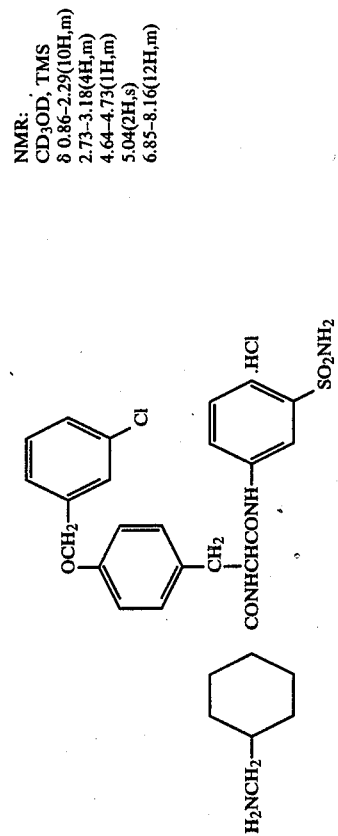 | NMR:<br>CD₃OD, TMS<br>δ 0.86–2.29(10H,m)<br>2.73–3.18(4H,m)<br>4.64–4.73(1H,m)<br>5.04(2H,s)<br>6.85–8.16(12H,m) |
| 94 | 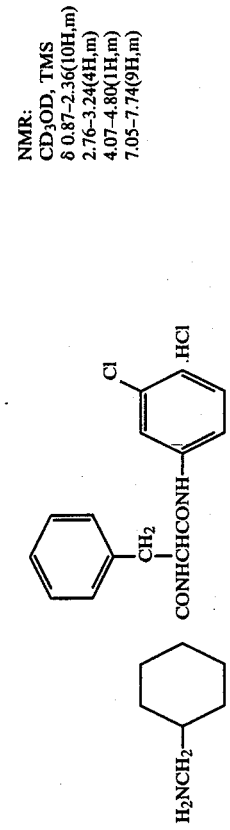 | NMR:<br>CD₃OD, TMS<br>δ 0.87–2.36(10H,m)<br>2.76–3.24(4H,m)<br>4.07–4.80(1H,m)<br>7.05–7.74(9H,m) |

-continued
| | | |
|---|---|---|
| 95 | 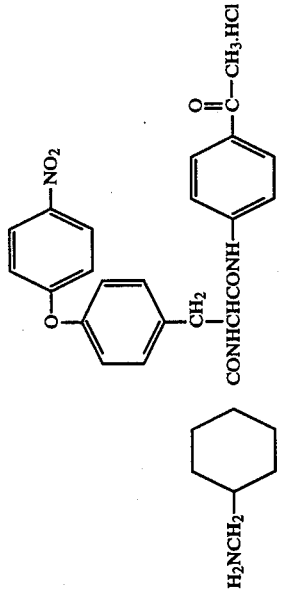 | NMR: CD₃OD, TMS δ 1.0–2.34(10H,m) 2.56(3H,s) 2.80(2H,m) 3.04–3.30(2H,m) 4.72(1H,m) 6.90–8.08(12H,m) |
| 96 | 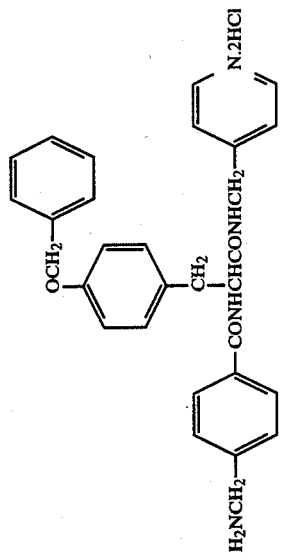 | MS: M/e 434,344,298,277, 254,226,197,185, 164,134,93 |
| 97 | 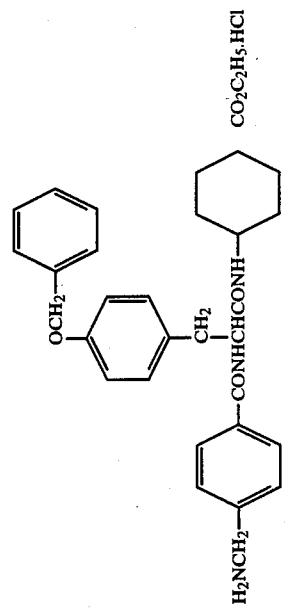 | MS: M/e 557,512,252,172, 134  IR: 2950,1735,1645,1515, 1240 |

| | | |
|---|---|---|
| 98 | 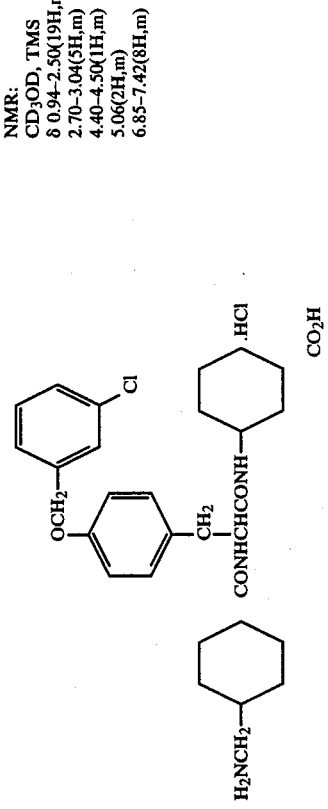 | NMR:<br>CD₃OD, TMS<br>$\delta$ 0.94–2.50(19H,m)<br>2.70–3.04(5H,m)<br>4.40–4.50(1H,m)<br>5.06(2H,m)<br>6.85–7.42(8H,m) |
| 99 | 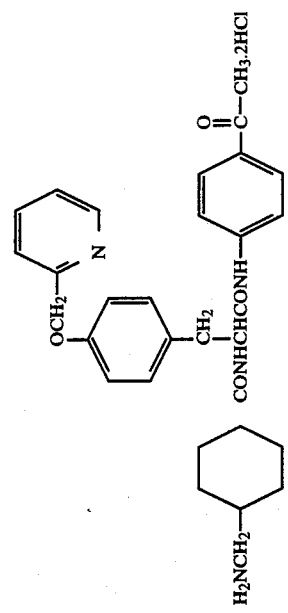 | NMR:<br>CD₃OD, TMS<br>$\delta$ 0.96–2.40(10H,m)<br>2.56(3H,s)<br>2.80–3.20(4H,m)<br>4.66–4.77(1H,m)<br>5.55(2H,s)<br>7.04–8.90(12H,m) |
| 100 | 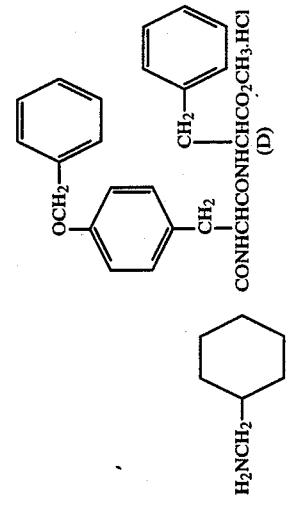 | NMR:<br>CD₃OD, TMS<br>$\delta$ 0.90–2.24(10H,m)<br>2.56–3.68(7H,m)<br>4.55–4.68(2H,m)<br>5.00(2H,s)<br>6.66–7.32(14H,m) |

-continued
| 101 | 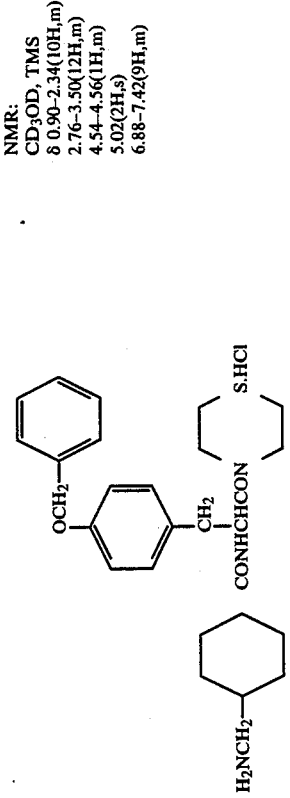 | NMR:<br>CD$_3$OD, TMS<br>δ 0.90–2.34(10H,m)<br>2.76–3.50(12H,m)<br>4.54–4.56(1H,m)<br>5.02(2H,s)<br>6.88–7.42(9H,m) |
|---|---|---|
| 102 | 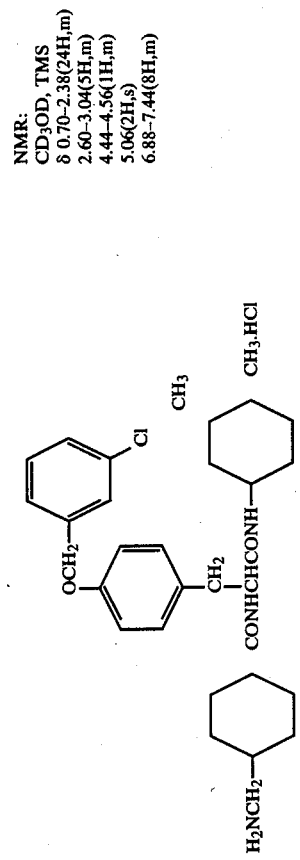 | NMR:<br>CD$_3$OD, TMS<br>δ 0.70–2.38(24H,m)<br>2.60–3.04(5H,m)<br>4.44–4.56(1H,m)<br>5.06(2H,s)<br>6.88–7.44(8H,m) |
| 103 | 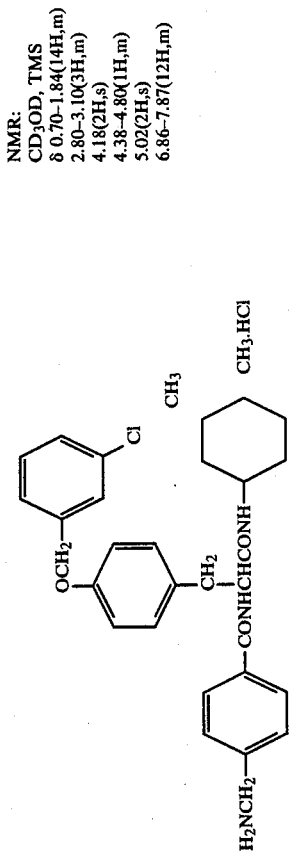 | NMR:<br>CD$_3$OD, TMS<br>δ 0.70–1.84(14H,m)<br>2.80–3.10(3H,m)<br>4.18(2H,s)<br>4.38–4.80(1H,m)<br>5.02(2H,s)<br>6.86–7.87(12H,m) |

-continued
| | | |
|---|---|---|
| 104 | 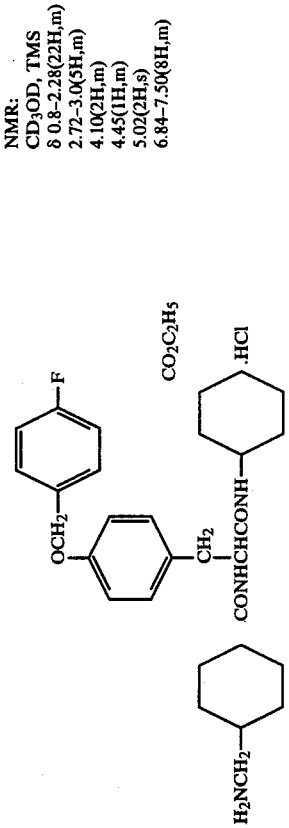 | NMR:<br>CD$_3$OD, TMS<br>δ 0.8–2.28(22H,m)<br>2.72–3.0(5H,m)<br>4.10(2H,m)<br>4.45(1H,m)<br>5.02(2H,s)<br>6.84–7.50(8H,m) |
| 105 | 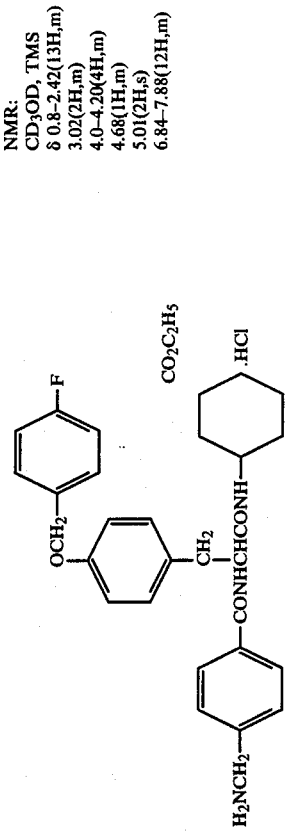 | NMR:<br>CD$_3$OD, TMS<br>δ 0.8–2.42(13H,m)<br>3.02(2H,m)<br>4.0–4.20(4H,m)<br>4.68(1H,m)<br>5.01(2H,s)<br>6.84–7.88(12H,m) |
| 106 | 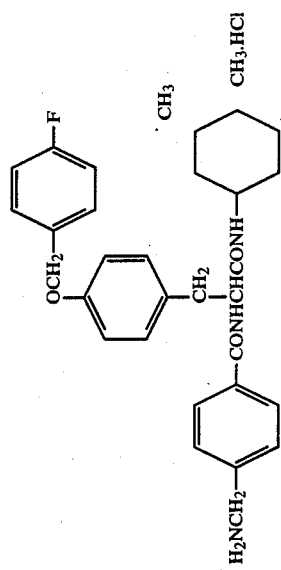 | IR:<br>3280,2960,2930,2875,<br>1700,1645,1615,1505,<br>1380,1225,825 |

-continued
| | | |
|---|---|---|
| 107 | 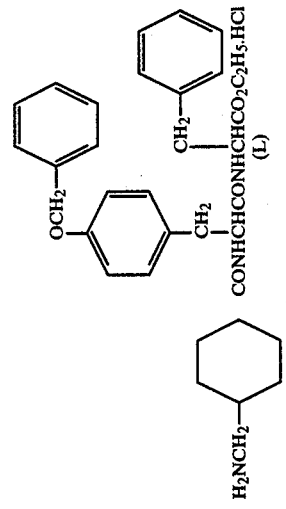 | IR:<br>3230,2930,1738,1645,<br>1535,1508,1242 |
| 108 | 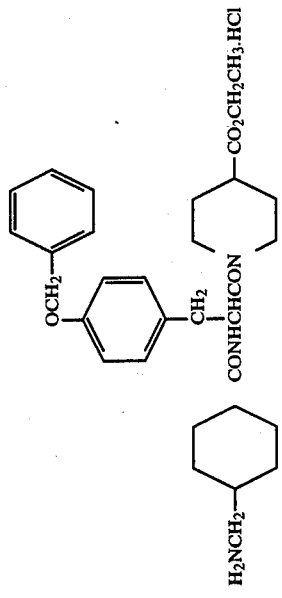 | MS:<br>M/e 549,504,393,302,<br>282,197 |
| 109 | 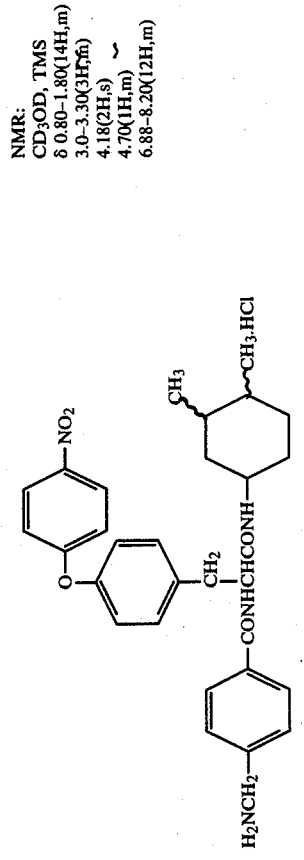 | NMR:<br>CD$_3$OD, TMS<br>δ 0.80–1.80(14H,m)<br>3.0–3.30(3H,m)<br>4.18(2H,s)<br>4.70(1H,m) ∼<br>6.88–8.20(12H,m) |

-continued
| | | |
|---|---|---|
| 110 | 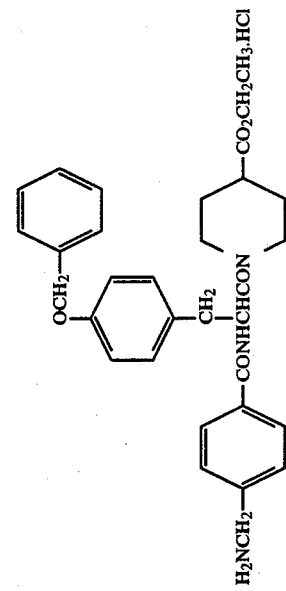 | MS:<br>M/e 543,498,393,387,<br>302,282,197,134 |
| 111 | 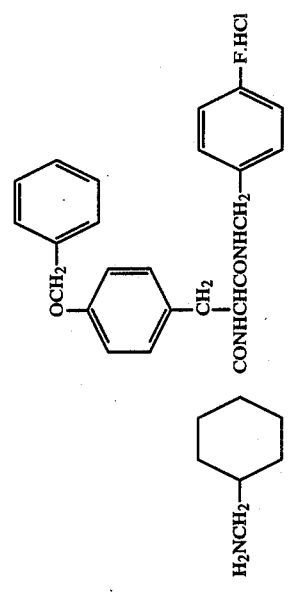 | IR:<br>3400,3300,3030,2930,<br>1640,1510,1240,1220<br><br>NMR:<br>CDCl$_3$—CD$_3$OD, TMS<br>δ 0.80–2.30(10H,m)<br>2.7(2H,d)<br>2.80–3.10(2H,m)<br>4.26(2H,d)<br>4.6(1H,t)<br>5.02(2H,s)<br>6.70–7.64(13H,m) |
| 112 | 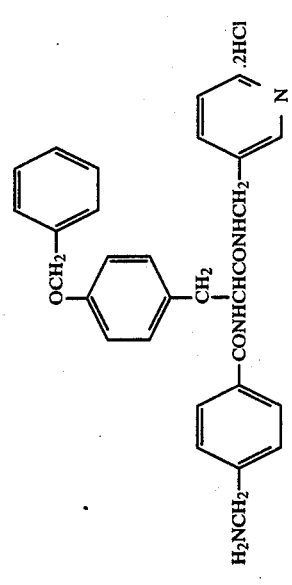 | MS:<br>M/e 494,476,459,433,<br>387,344,281,197,<br>150,106 |

| | -continued | | |
|---|---|---|---|
| 113 | 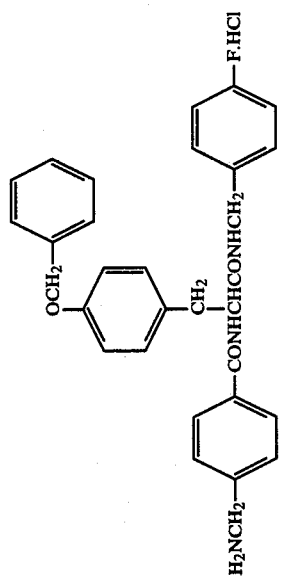 | IR:<br>3420,3280,2960,2930,<br>1630,1510,1240,1220 | NMR:<br>CDCl$_3$—CD$_3$OD, TMS<br>δ 3.0–3.16(2H,m)<br>4.12(2H,s)<br>4.46(2H,d)<br>4.78(1H,t)<br>5.02(2H,s)<br>6.80–7.90(17H,m) |
| 114 | 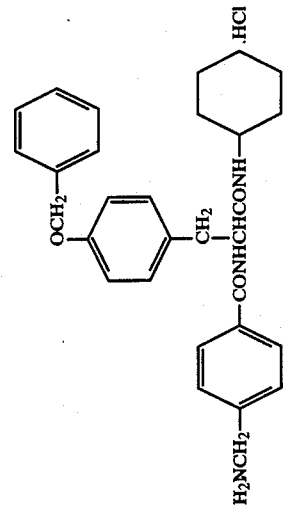 | IR:<br>3430,2940,2860,1640,<br>1515,1240 | NMR:<br>CDCl$_3$—CD$_3$OD, TMS<br>δ 0.80–1.90(10H,m)<br>2.95–3.10(2H,m)<br>3.50–3.70(1H,m)<br>4.12(2H,s)<br>4.70(1H,t)<br>5.04(2H,s)<br>6.80–7.90(13H,m) |
| 115 | 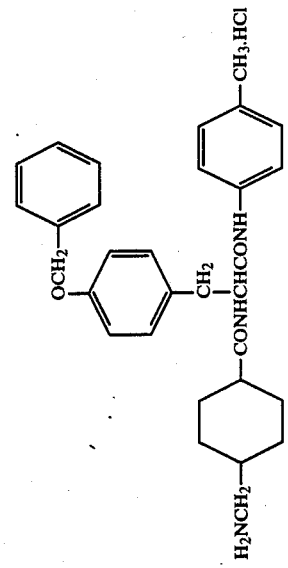 | IR:<br>3430,3030,2940,1695,<br>1640,1610,1510,1455,<br>1240,1230,1140,990,<br>910,810,740 | |

| | | |
|---|---|---|
| 116 | 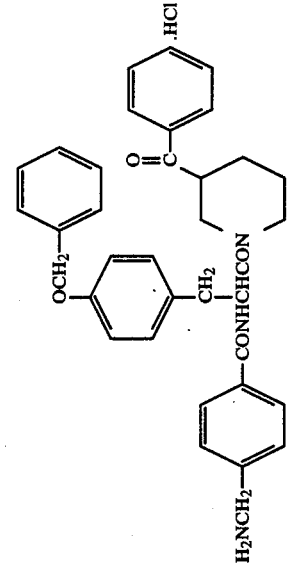 | IR: 3440,1745,1640,1515, 1245,1225 |
| 117 | 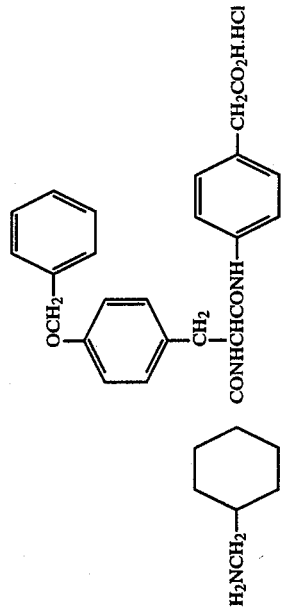 | IR: 3600-2400,1690,1610<br>MS: M/e 387,197,151,91 |
| 118 | 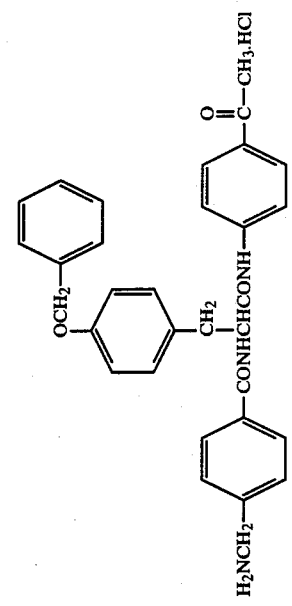 | IR: 3420,3030,1670,1640, 1600,1530,1510,1270<br>NMR: CD$_3$OD, TMS<br>δ 2.56(3H,s)<br>3.10-3.30(2H,m)<br>3.98(2H,s)<br>4.60-4.80(1H,m)<br>5.00(2H,s)<br>6.80-8.00(17H,m) |

-continued
| 119 | 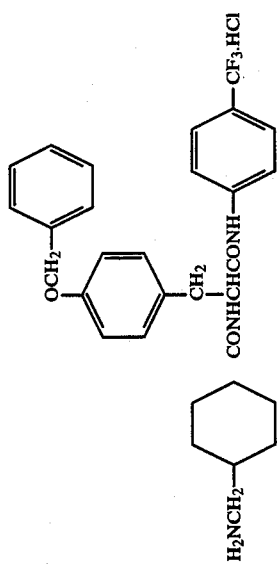 | IR:<br>3420,3300,3030,2930,<br>1740,1645,1610,1515,<br>1320,1240 | NMR:<br>CD₃OD, TMS<br>δ 0.80–2.30(10H,m)<br>2.76(2H,d)<br>2.80–3.20(2H,m)<br>4.50–4.80(1H,m)<br>5.02(2H,s)<br>6.80–7.70(13H,m) |
|---|---|---|---|
| 120 | 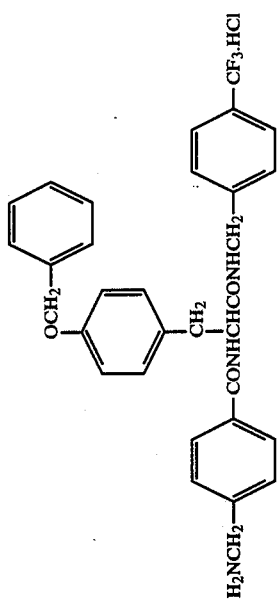 | IR:<br>3430,3030,2950,1730,<br>1640,1610,1510,1310,<br>1240 | |
| 121 | 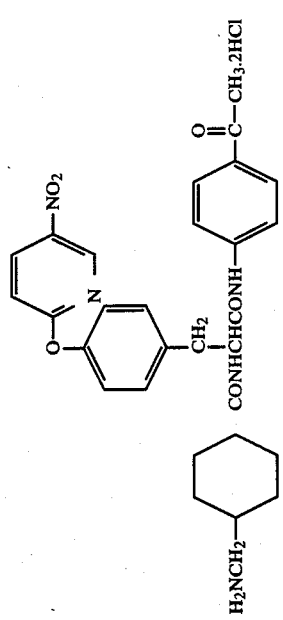 | | NMR:<br>CD₃OD, TMS<br>δ 0.90–2.40(10H,m)<br>2.58(3H,s)<br>2.80(2H,d)<br>3.10(2H,m)<br>7.0–8.90(11H,m) |

-continued
| | | |
|---|---|---|
| 122 | 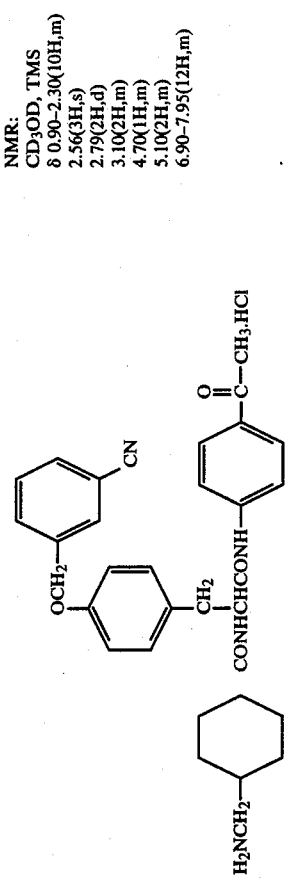 | NMR:<br>CD₃OD, TMS<br>δ 0.90–2.30(10H,m)<br>2.56(3H,s)<br>2.79(2H,d)<br>3.10(2H,m)<br>4.70(1H,m)<br>5.10(2H,m)<br>6.90–7.95(12H,m) |
| 123 | 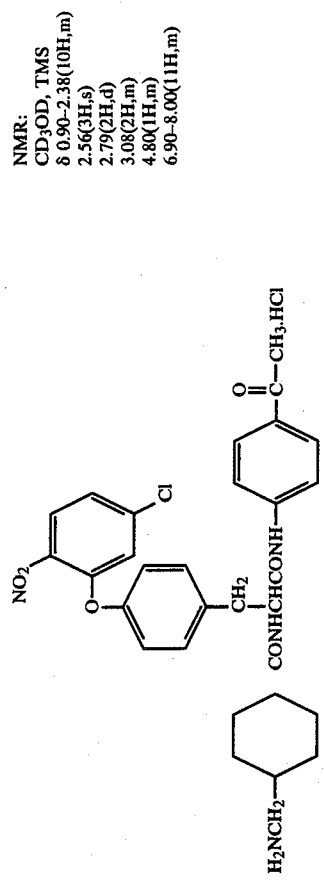 | NMR:<br>CD₃OD, TMS<br>δ 0.90–2.38(10H,m)<br>2.56(3H,s)<br>2.79(2H,d)<br>3.08(2H,m)<br>4.80(1H,m)<br>6.90–8.00(11H,m) |
| 124 | 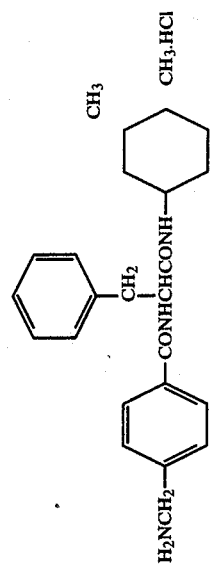 | IR:<br>3430,3060,2960,2940,<br>1640,1550,1510,1380,<br>1310 |

-continued
| | | NMR: |
|---|---|---|
| 125 | 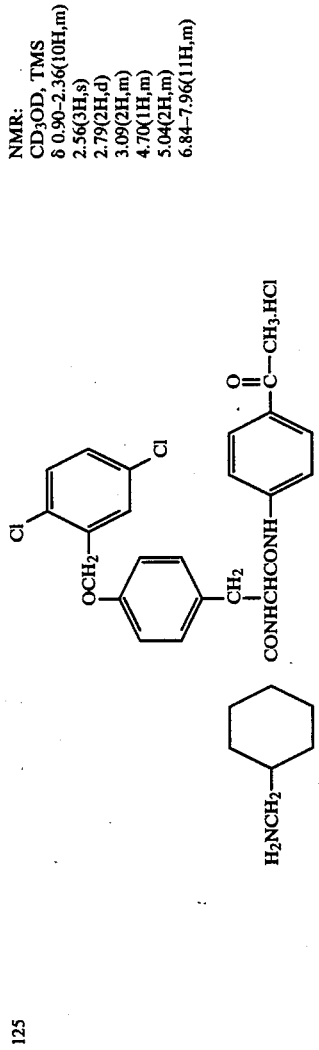 | CD₃OD, TMS<br>δ 0.90–2.36(10H,m)<br>2.56(3H,s)<br>2.79(2H,d)<br>3.09(2H,m)<br>4.70(1H,m)<br>5.04(2H,m)<br>6.84–7.96(11H,m) |
| 126 | 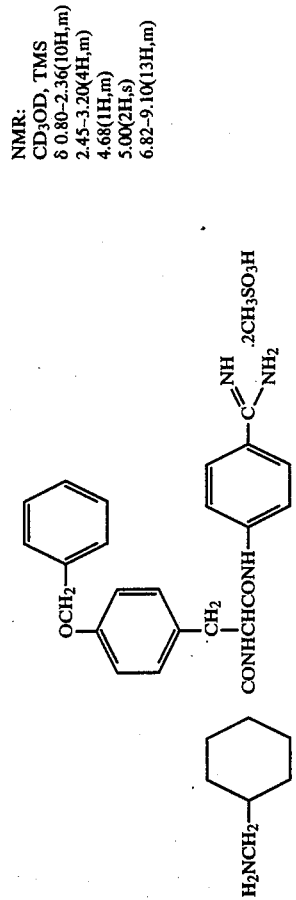 | NMR:<br>CD₃OD, TMS<br>δ 0.80–2.36(10H,m)<br>2.45–3.20(4H,m)<br>4.68(1H,m)<br>5.00(2H,s)<br>6.82–9.10(13H,m) |
| 127 | 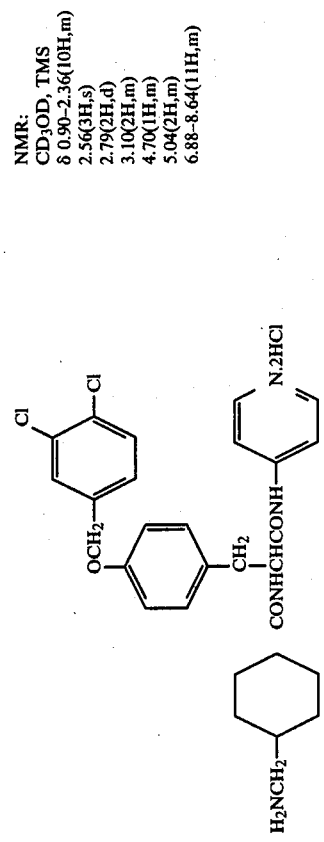 | NMR:<br>CD₃OD, TMS<br>δ 0.90–2.36(10H,m)<br>2.56(3H,s)<br>2.79(2H,d)<br>3.10(2H,m)<br>4.70(1H,m)<br>5.04(2H,m)<br>6.88–8.64(11H,m) |

-continued

| No. | Structure | Spectral Data |
|---|---|---|
| 128 | 3-chlorobenzyloxy-phenyl / 2-chloropyridin-4-yl·2HCl / cyclohexylmethyl / CONHCHCONH / H₂NCH₂ | NMR: CD₃OD, TMS δ 0.90–2.35(10H,m) 2.56(3H,s) 2.79(2H,d) 3.04(2H,m) 4.70(1H,m) 5.04(2H,s) 6.84–8.50(11H,m) |
| 129 | pyridin-3-ylmethoxyphenyl / cyclohexylmethyl / CONHCHCONH / H₂NCH₂ | NMR: CD₃OD, TMS δ 0.90–2.36(10H,m) 2.58(2H,s) 2.82(2H,d) 3.10(2H,m) 4.72(1H,m) 5.50(2H,s) 7.04–8.86(12H,m) |
| 130 | 4-nitrobenzyl / 4-acetylphenyl·2HCl / cyclohexylmethyl / CONHCHCONH / H₂NCH₂ | IR: 3280,2940,1680,1600, 1520,1345,1270,1180, 840 |
| 131 | benzyl / 3-trifluoromethylphenyl·HCl / 4-acetylphenyl / CONHCHCONH / H₂NCH₂ | IR: 3400,3350,3160,1670, 1650,1600,1510,1380, 1330,1155,1125  NMR: CD₃OD, TMS δ 3.0–3.40(2H,m) 4.18(2H,s) 4.60–4.90(1H,m) 7.10–8.0(13H,m) |

-continued
| | | IR: | NMR: |
|---|---|---|---|
| 132 | 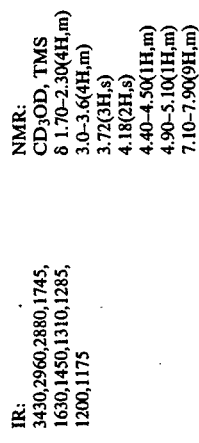 | 3430,2960,2880,1745, 1630,1450,1310,1285, 1200,1175 | CD$_3$OD, TMS δ 1.70-2.30(4H,m) 3.0-3.6(4H,m) 3.72(3H,s) 4.18(2H,s) 4.40-4.50(1H,m) 4.90-5.10(1H,m) 7.10-7.90(9H,m) |
| 133 | 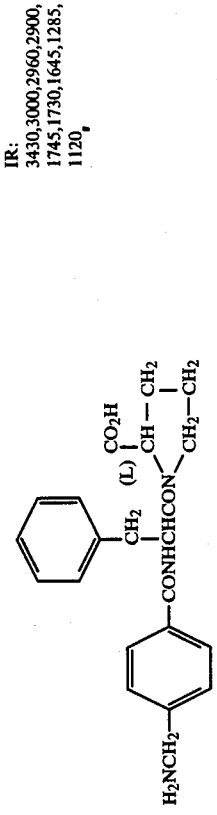 | 3430,3000,2960,2900, 1745,1730,1645,1285, 1120 | |
| 134 | 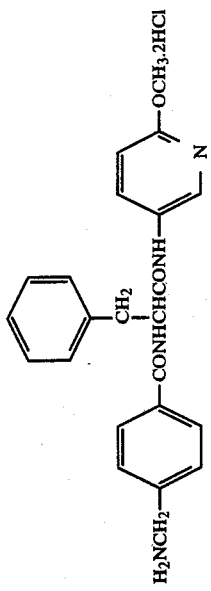 | 3430,3030,2960,1640, 1615,1550,1500,1295,1010 | CD$_3$OD, TMS δ 3.10-3.40(2H,m) 4.14(3H,s) 4.16(2H,s) 4.80-5.0(1H,m) 7.10-8.80(12H,m) |
| 135 | 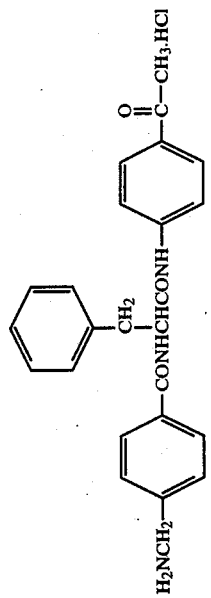 | 3430,3030,2930,1670, 1640,1630,1600,1500, 1410,1360,1310,1270, 1180 | CD$_3$OD, TMS δ 2.56(3H,s) 3.10-3.30(2H,m) 4.16(2H,s) 4.90-5.0(1H,m) 7.10-8.0(13H,m) |

-continued
| | | |
|---|---|---|
| 136 | 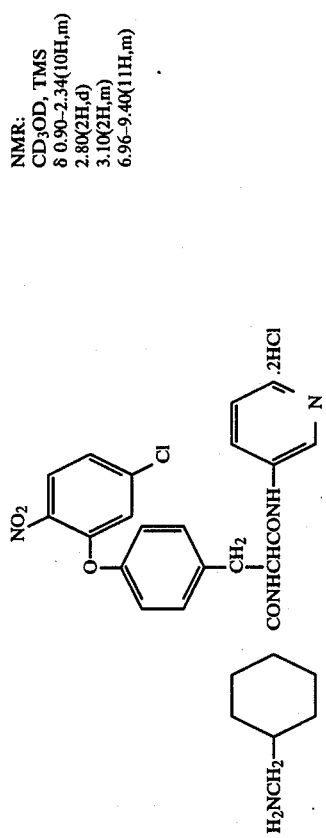 | NMR: CD₃OD, TMS δ 0.90-2.34(10H,m) 2.80(2H,d) 3.10(2H,m) 6.96-9.40(11H,m) |
| 137 | 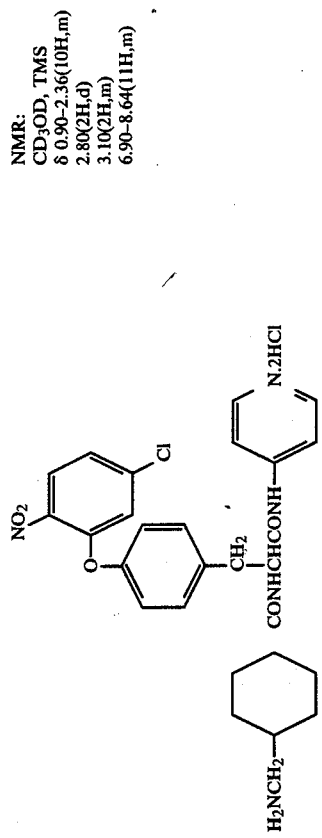 | NMR: CD₃OD, TMS δ 0.90-2.36(10H,m) 2.80(2H,d) 3.10(2H,m) 6.90-8.64(11H,m) |
| 138 | 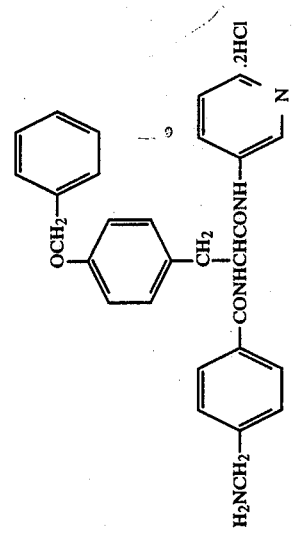 | MS: M/e 480,432,359,282, 255,205,197,178, 150,133,106 |

-continued
| 139 | 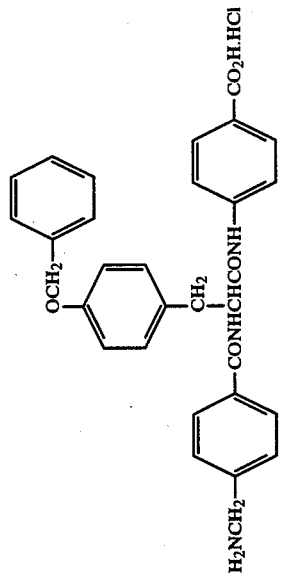 | IR: 3420,1700,1640,1540, 1300 |

| 140 | 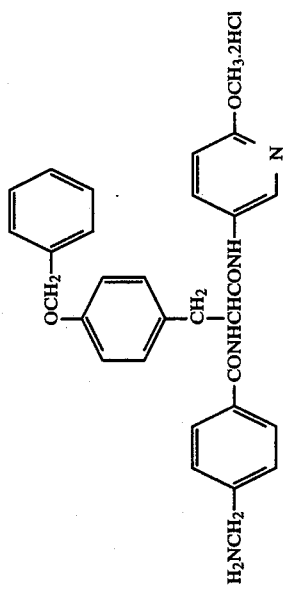 | IR:<br>3430,3030,2950,2620,<br>1645,1615,1550,1510,<br>1440,1300,1235 | NMR:<br>CD$_3$OD, TMS<br>δ 3.10–3.30(2H,m)<br>4.14(3H,s)<br>4.18(2H,s)<br>4.70–4.90(1H,m)<br>5.0(2H,s)<br>6.80–8.80(16H,m) |
|---|---|---|---|
| 141 | 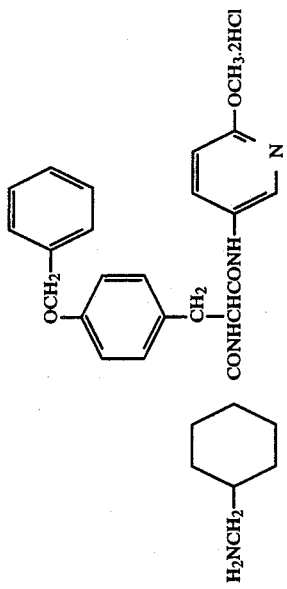 | IR:<br>3430,3030,2930,1650,<br>1620,1550,1510,1460,<br>1440,1300,1220 | NMR:<br>CD$_3$OD, TMS<br>δ 0.90–2.40(10H,m)<br>2.78(2H,d)<br>2.80–3.20(2H,s)<br>4.18(3H,s)<br>4.50–4.70(1H,m)<br>5.02(2H,s)<br>6.80–8.80(12H,m) |
| 142 | 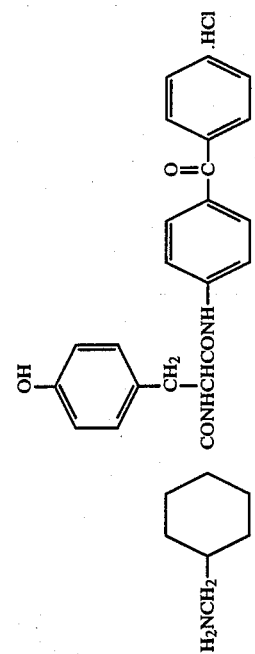 | | NMR:<br>CD$_3$OD, TMS<br>δ 0.90–2.32(10H,m)<br>2.78(2H,d)<br>3.08(2H,m)<br>4.68(1H,m)<br>6.64–7.80(13H,m) |

-continued
| | | |
|---|---|---|
| 143 | 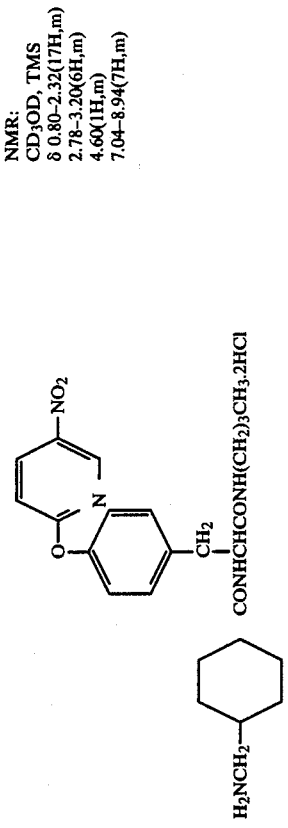 | NMR:<br>CD₃OD, TMS<br>δ 0.80–2.32(17H,m)<br>2.78–3.20(6H,m)<br>4.60(1H,m)<br>7.04–8.94(7H,m) |
| 144 | 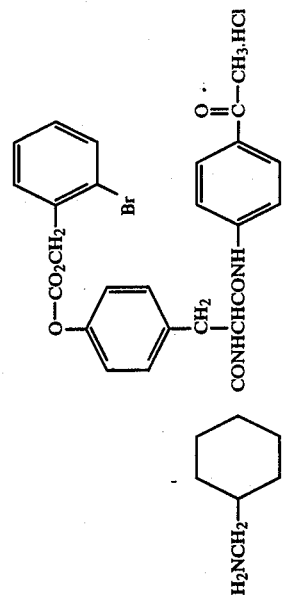 | IR:<br>1760,1690,1680,1590,<br>1510,1440 |
| 145 | 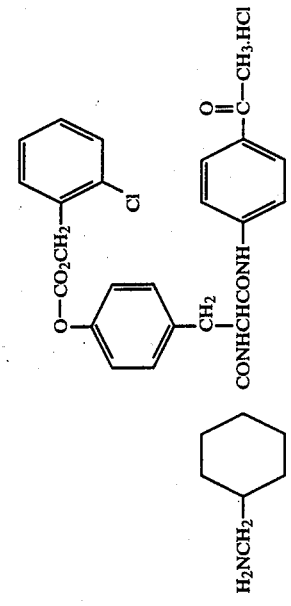 | IR:<br>1760,1690,1680,1590,<br>1510,1440 |

-continued
| | | |
|---|---|---|
| 146 | 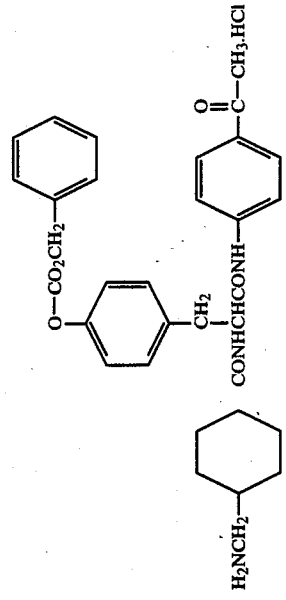 | IR:<br>1760,1690,1680,1590,<br>1510,1440 |
| 147 | 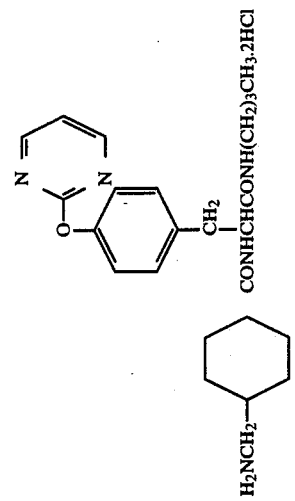 | NMR:<br>CD₃OD, TMS<br>δ 0.81–2.32(17H,m)<br>2.70–3.28(6H,m)<br>4.40–4.66(1H,m)<br>6.64–8.80(7H,m) |
| 148 | 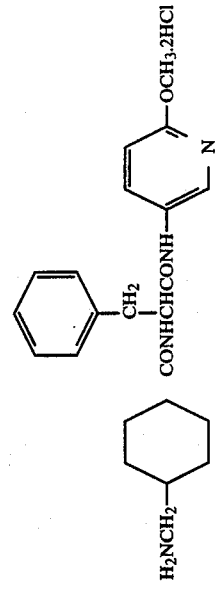 | IR:<br>3430,3300,3030,2930,<br>1700,1650,1560,1460<br>1440,1340,1300,1010,<br>850,700 |

-continued
| | | |
|---|---|---|
| 149 | 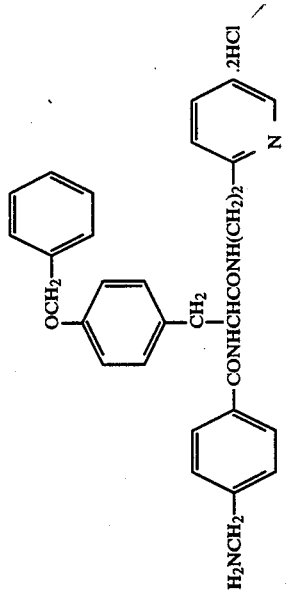 | NMR:<br>CD₃OD, TMS<br>δ 2.88–3.12(2H,broad)<br>3.66(2H,s)<br>4.12–4.28(5H,m)<br>5.02(2H,s)<br>6.84–8.76(17H,m) |
| 150 | 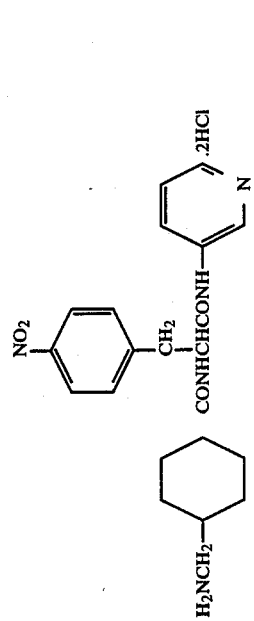 | NMR:<br>CD₃OD, TMS<br>δ 0.90–2.00(10H,m)<br>2.10–2.30(2H,m)<br>2.80(4H,m)<br>4.90(1H,t)<br>7.40–7.70(4H,m)<br>7.95–8.70(4H,m) |
| 151 | 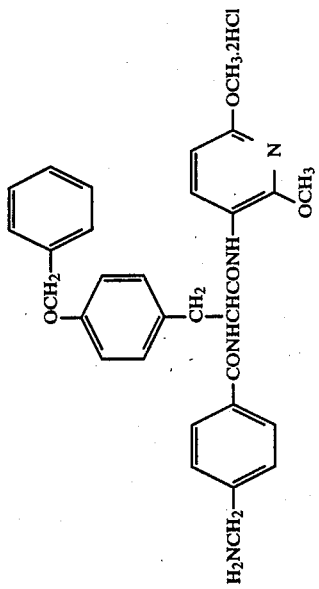 | MS:<br>M/e 540,390,237,197,<br>154,134<br><br>IR:<br>3430,3030,2950,1640,<br>1620,1510,1480,1420,<br>1390,1300,1245,1175,<br>1020,810,700 |

| | | |
|---|---|---|
| 152 | 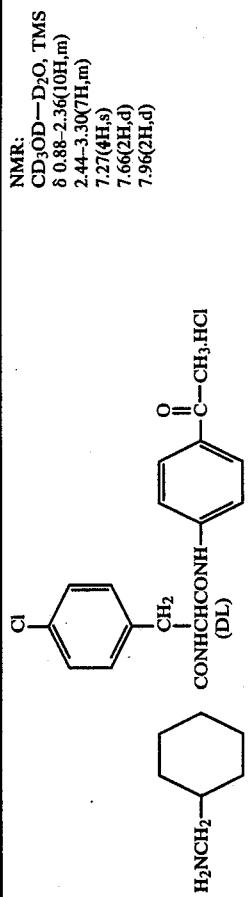 | NMR:<br>CD$_3$OD—D$_2$O, TMS<br>δ 0.88–2.36(10H,m)<br>2.44–3.30(7H,m)<br>7.27(4H,s)<br>7.66(2H,d)<br>7.96(2H,d) |
| 153 | 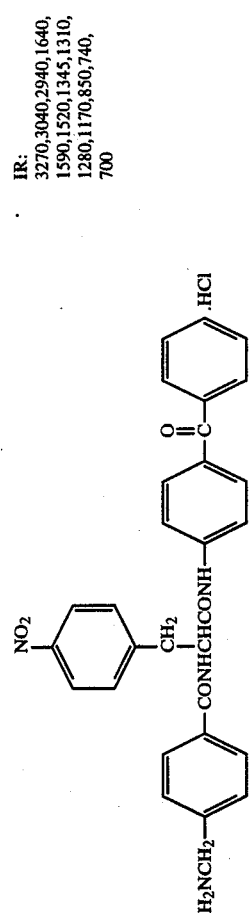 | IR:<br>3270,3040,2940,1640,<br>1590,1520,1345,1310,<br>1280,1170,850,740,<br>700 |
| 154 | 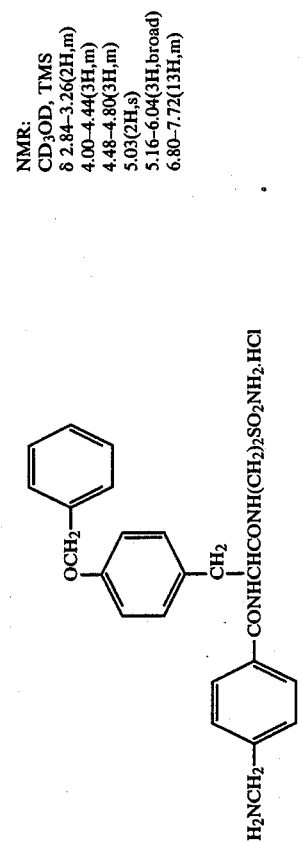 | NMR:<br>CD$_3$OD, TMS<br>δ 2.84–3.26(2H,m)<br>4.00–4.44(3H,m)<br>4.48–4.80(3H,m)<br>5.03(2H,s)<br>5.16–6.04(3H,broad)<br>6.80–7.72(13H,m) |
| 155 | 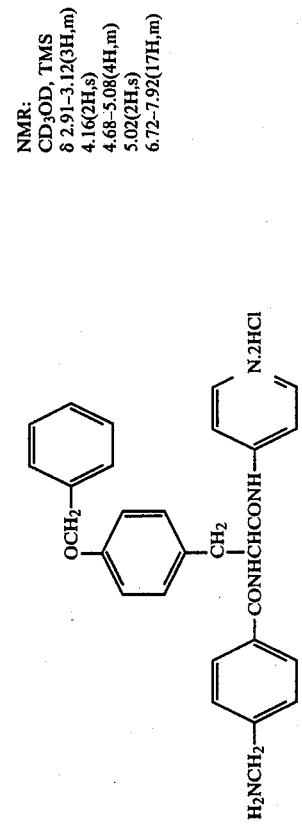 | NMR:<br>CD$_3$OD, TMS<br>δ 2.91–3.12(3H,m)<br>4.16(2H,s)<br>4.68–5.08(4H,m)<br>5.02(2H,s)<br>6.72–7.92(17H,m) |

| | | |
|---|---|---|
| 156 | 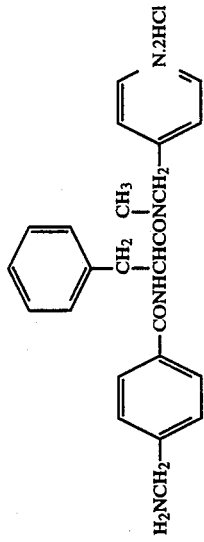 | MS: M/e 402,311,253,134 IR: 3430,3020,1720,1640, 1570,1540,1500,1280, 1115,1070,760,700 |
| 157 | 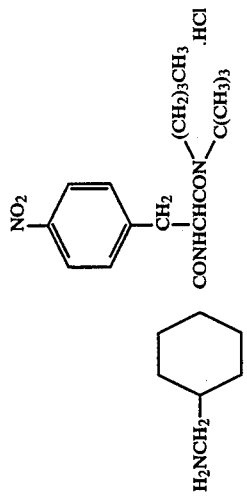 | IR: 3300,2940,1650,1520, 1350,1210,1110,1020, 860 |
| 158 | 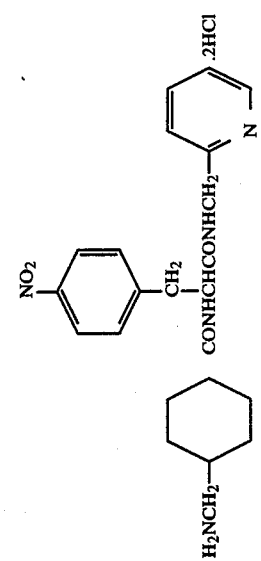 | IR: 3420,3290,2940,1680, 1650,1520,1350,1220, 1105,1040,860,760 |
| 159 | 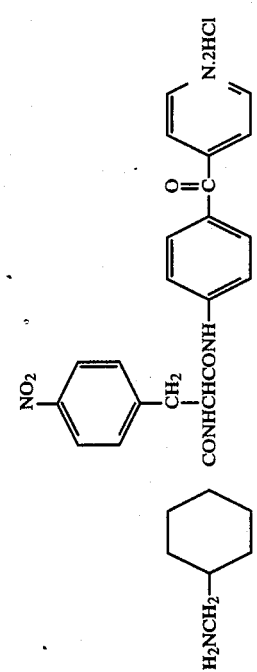 | IR: 3450,3200,3000,2850, 2670,2000,1745,1605, 1505,1495,1350,1230, 1105,1005,840,750, 700 |

| | | |
|---|---|---|
| 160 | 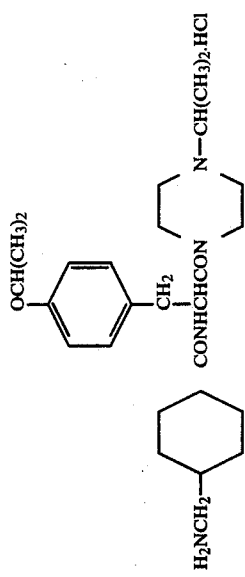 | MS:<br>M/e 473,430,415,345,<br>317,205,128,113,<br>86 |
| 161 | 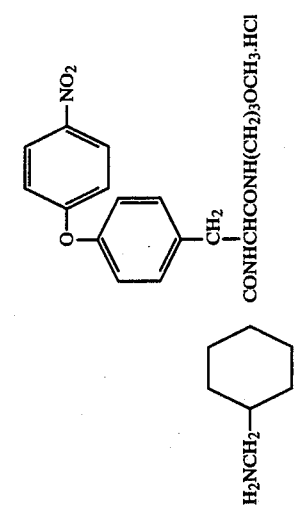 | NMR:<br>CD₃OD, TMS<br>δ 0.84–2.35(12H,m)<br>2.70–3.40(8H,m)<br>3.31(3H,s)<br>4.52–4.64(1H,m)<br>6.96–7.08(4H,m)<br>7.34(2H,d)<br>8.11(2H,d) |
| 162 | 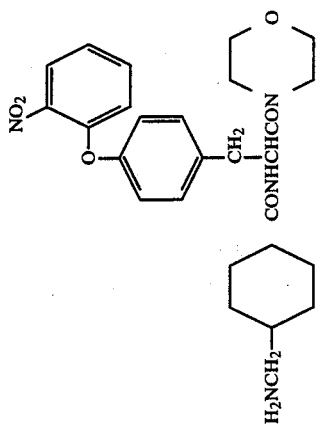 | NMR:<br>CDCl₃, TMS<br>δ 0.78–3.24(22H,m)<br>4.80–4.92(1H,m)<br>5.92–6.04(1H,m)<br>6.90–7.96(8H,m) |

-continued
| 163 | 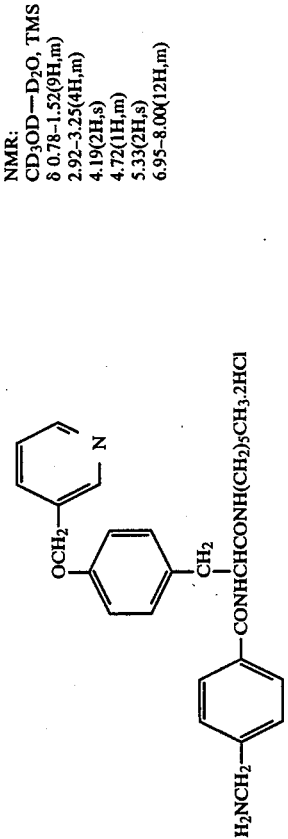 | NMR:<br>CD₃OD—D₂O, TMS<br>δ 0.78–1.52(9H,m)<br>2.92–3.25(4H,m)<br>4.19(2H,s)<br>4.72(1H,m)<br>5.33(2H,s)<br>6.95–8.00(12H,m) |
|---|---|---|
| 164 | 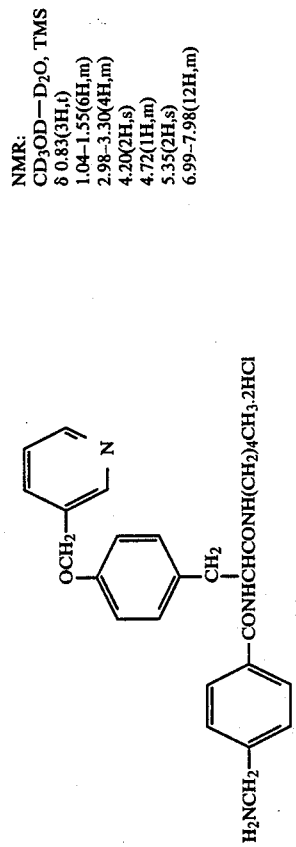 | NMR:<br>CD₃OD—D₂O, TMS<br>δ 0.83(3H,t)<br>1.04–1.55(6H,m)<br>2.98–3.30(4H,m)<br>4.20(2H,s)<br>4.72(1H,m)<br>5.35(2H,s)<br>6.99–7.98(12H,m) |
| 165 | 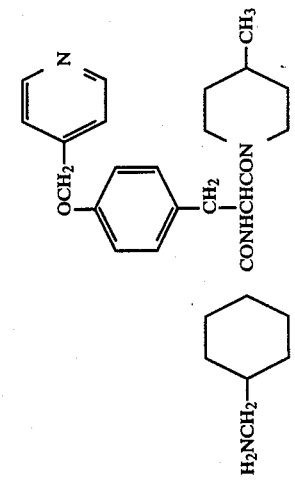 | NMR:<br>CDCl₃, TMS<br>δ 0.70–3.02(26H,m)<br>4.98–5.20(3H,m)<br>6.92–7.12(4H,m)<br>7.34(2H,d)<br>8.58(2H,d) |

-continued
| | | |
|---|---|---|
| 166 | 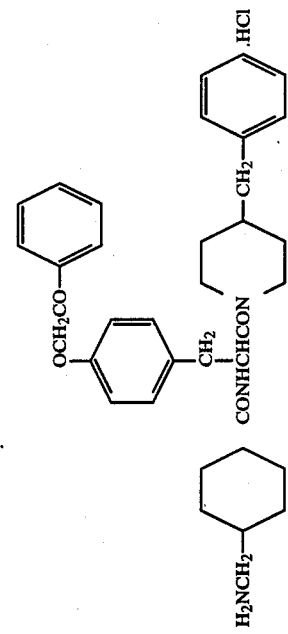 | MS:<br>M/e 321,293,231,175 |
| 167 | 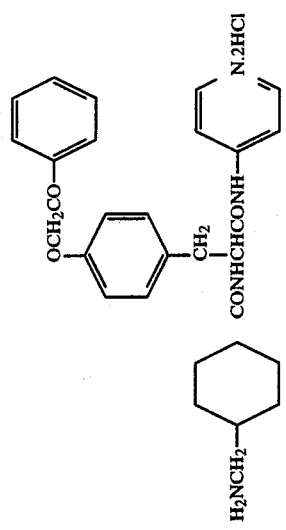 | MS:<br>M/e 177,107,94,67<br><br>IR:<br>3430,3020,2940,1730,<br>1700,1640,1610,1510,<br>1320,1220,820 |
| 168 | 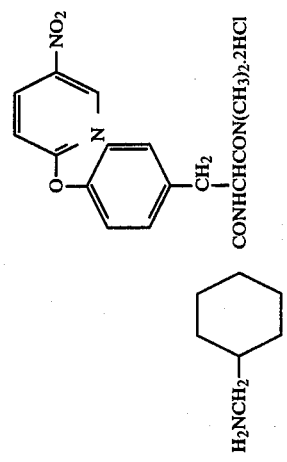 | NMR:<br>CD$_3$OD, TMS<br>δ 0.90–2.36(10H,m)<br>2.40–3.16(11H,m)<br>6.92–8.96(7H,m) |

-continued
| 169 | 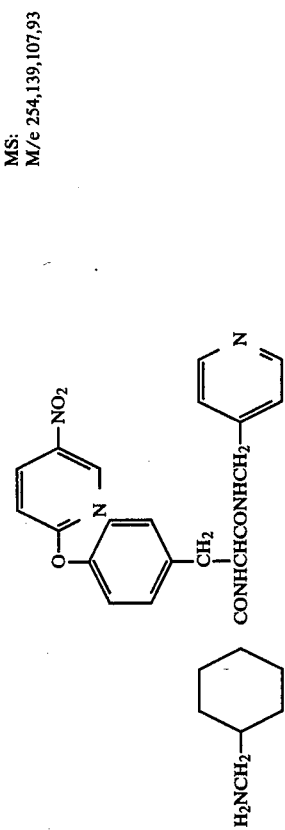 | MS: M/e 254,139,107,93 |
| --- | --- | --- |
| 170 | 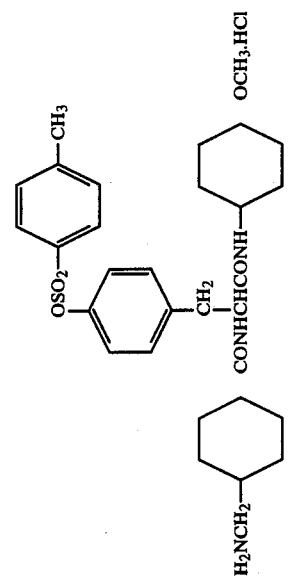 | IR: 3400,2940,1740,1650, 1500,1450,1370,1200, 1180,1150,1090,860 |
| 171 | 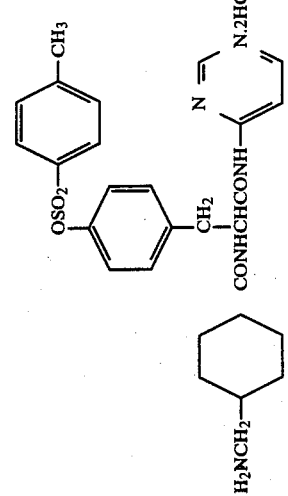 | IR: 3400,2940,1740,1640, 1500,1370,1200,1180, 1150,1090,860 |

-continued
| | | |
|---|---|---|
| 172 | 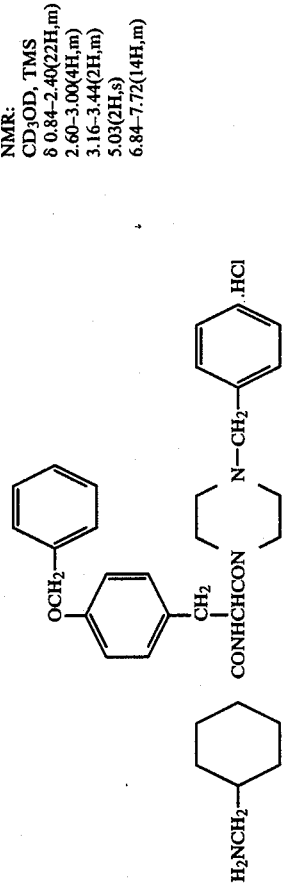 | NMR:<br>CD₃OD, TMS<br>δ 0.84-2.40(22H,m)<br>2.60-3.00(4H,m)<br>3.16-3.44(2H,m)<br>5.03(2H,s)<br>6.84-7.72(14H,m) |
| 173 | 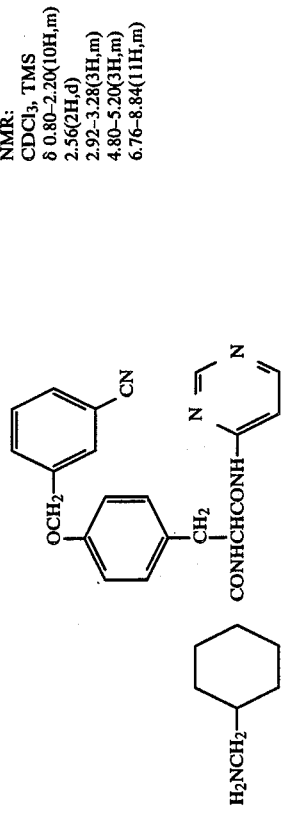 | NMR:<br>CDCl₃, TMS<br>δ 0.80-2.20(10H,m)<br>2.56(2H,d)<br>2.92-3.28(3H,m)<br>4.80-5.20(3H,m)<br>6.76-8.84(11H,m) |
| 174 | 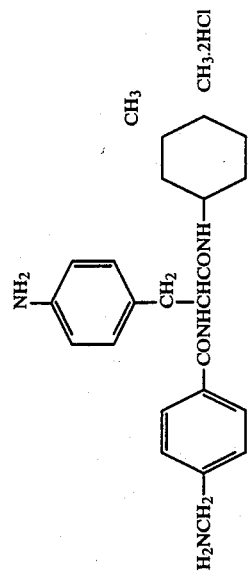 | IR:<br>3270,2940,1640,1530,<br>1510,1380,1090 |

-continued
| | | NMR: | |
|---|---|---|---|
| 175 | 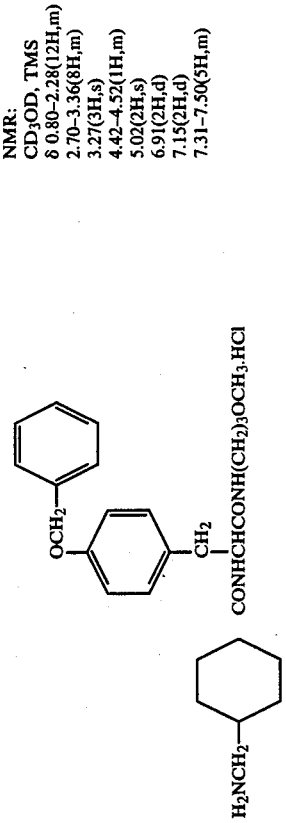 | CD₃OD, TMS<br>δ 0.80–2.28(12H,m)<br>2.70–3.36(8H,m)<br>3.27(3H,s)<br>4.42–4.52(1H,m)<br>5.02(2H,s)<br>6.91(2H,d)<br>7.15(2H,d)<br>7.31–7.50(5H,m) | |
| 176 | 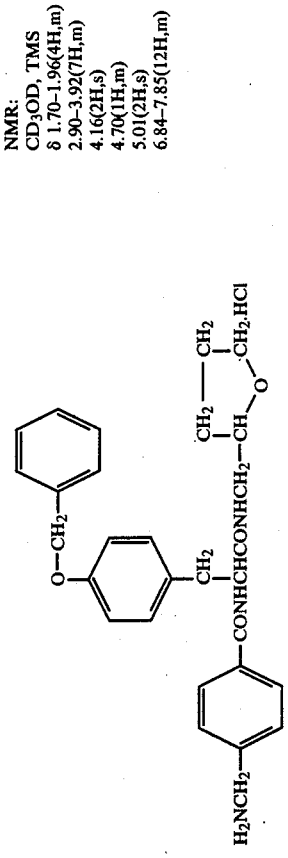 | NMR:<br>CD₃OD, TMS<br>δ 1.70–1.96(4H,m)<br>2.90–3.92(7H,m)<br>4.16(2H,s)<br>4.70(1H,m)<br>5.01(2H,s)<br>6.84–7.85(12H,m) | |
| 177 | 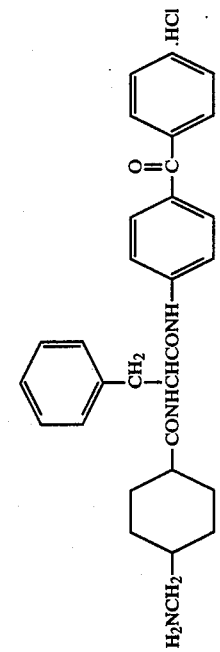 | MS:<br>M/e 483,328,197 | IR:<br>3430,3060,2930,1710,<br>1640,1600,1530,1410,<br>1310,1280,700 |

-continued
| | | |
|---|---|---|
| 178 | 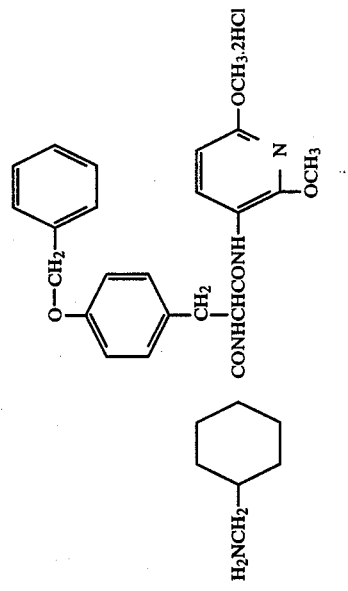 | MS:<br>M/e 546,390,197,154 |
| 179 | 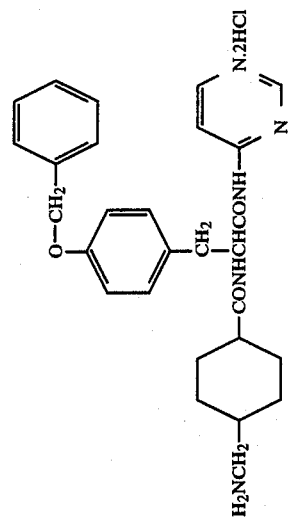 | IR:<br>3430,3030,2930,1730<br>1635,1610,1510,1480,<br>1310,1240,1200,830<br>700 |
| 180 | 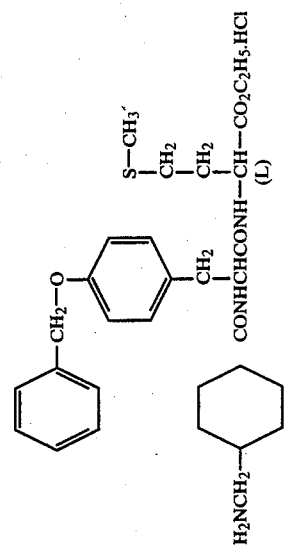 | NMR:<br>CD$_3$OD—D$_2$O, TMS<br>δ 0.80–2.30(12H,m)<br>1.24(3H,t)<br>2.06(3H,s)<br>2.32–2.60(2H,m)<br>2.66–3.38(4H,m)<br>4.16(2H,q)<br>4.44–4.66(2H,m)<br>5.04(2H,s)<br>6.86(2H,d)<br>7.16(2H,d)<br>7.22–7.44(5H,m) |

-continued
| | | |
|---|---|---|
| 181 | [structure with pyridine-OCH2-phenyl-CH2-CONHCHCON-morpholine and cyclohexyl-CH2NH2] | NMR:<br>CDCl3,TMS<br>δ 0.78–3.70(22H,m)<br>5.00–5.12(3H,broad)<br>6.86(2H,d)<br>7.10(2H,d)<br>7.34(2H,d)<br>8.59(2H,d) |
| 182 | [structure with CH3-phenyl-OSO2-phenyl-CH2-CONHCHCONH-pyridine·2HCl and cyclohexyl-CH2NH2] | IR:<br>3400,2940,1730,1640,<br>1500,1370,1200,1180,<br>1150,870 |
| 183 | [structure with NO2-phenyl-CH2-CONHCHCONHCH2-pyridine·2HCl and cyclohexyl-CH2NH2] | IR:<br>3400,3050,2940,1640,<br>1510,1350,860,760 |
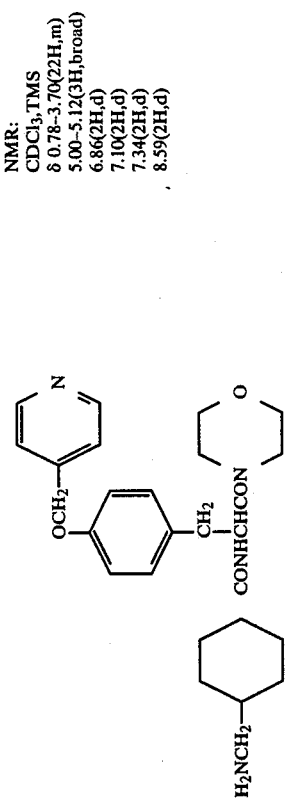

The compounds of the present invention can be synthesized by various combinations of the so-called peptide synthesis methods.

(1) Mixed acid anhydride method [Ann, Chem., 572,] 190 (1951)
(2) Acid chloride method [Biochemistry., 4, 2219 (1960)]
(3) Phosphazo method [Chem. Ber., 93, 2387 (1960)]
(4) Dicyclohexylcarbodiimide method [J. Am. Chem. Soc., 77, 1067 (1955)]
(5) Active ester method using, for example, N-hydroxysuccinimide [J. Am. Chem. Soc., 85, 3039 (1963)].

It should be noted, however, that not all of the compounds can be synthesized according to the methods as mentioned here, but that it is necessary to combine the above-mentioned methods appropriately for the respective compounds. Among these methods, typical examples of the reaction routes are shown below.

Route A

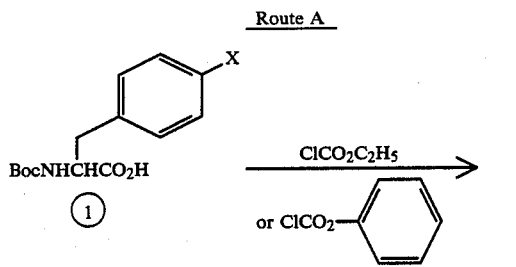

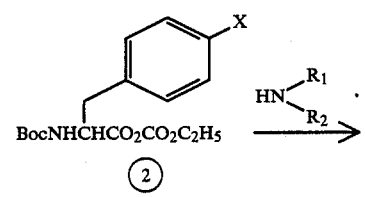

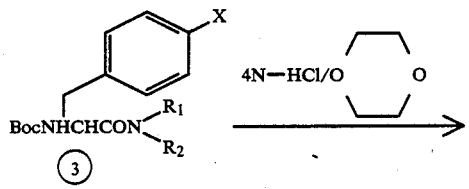

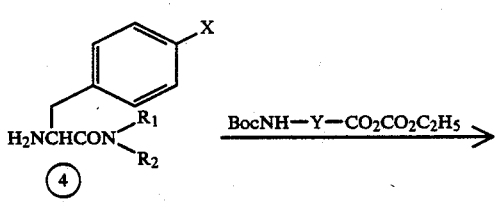

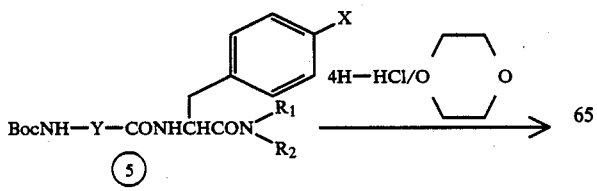

-continued
Route A

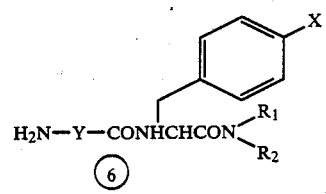

For carrying out synthesis from ①  to ③, ① is dissolved in an appropriate solvent such as THF, dimethylsulfoxide diethyl ether, dioxane, and the like, and an appropriate base such as triethylamine, pyridine, and the like, is added in an amount of 1 equivalent to 5 equivalents, preferably 2 to 3 equivalents relative to ①. To this reaction mixture is added ethyl chlorocarbonate as such or as a solution dissolved in the solvent used as the reaction solvent, at one time or in several divided portions. The temperature of the reaction mixture is maintained at −10° C. to 30° C., preferably 5° to 10° C. The reaction time is from 1 hour to 50 hours, preferably from 5 to 20 hours. After a conventional post-treatment, 0.5 to 2 equivalents of

are added and the reaction is carried out at −10° C. to 30° C., preferably 5° to 20° C., for 1 to 50 hours, preferably 5 to 20 hours. Then, after a conventional post-treatment, ③ is obtained.

The reaction from ③ to ④ may be carried out by allowing ③ to react with 1 to 10 equivalents, preferably 3 to 7 equivalents relative to ③ of 4N-HCl dioxane solution at room temperature. Then, after a conventional post-treatment, ④ is obtained. The reactions from ④ to ⑥ can be carried out in the same way as from ① to ④, whereby ⑥ can be obtained.

Route B

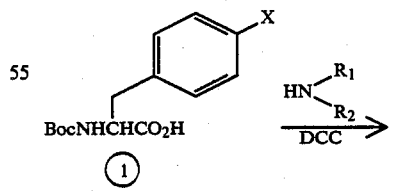

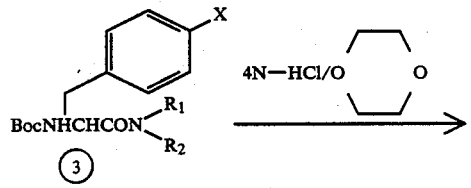

-continued
Route B

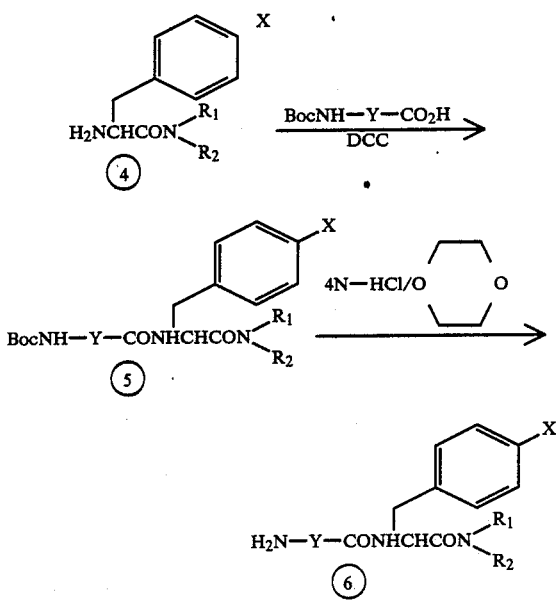

For the syntheses from ①  to ③ and from ④ to ⑤, there may be employed, for example, the methods as described in J. Am. Chem. Soc., 77 1067 (1955). For the reactions from ③ to ④ and from ⑤ to ⑥, the methods as described in route A may be used.

Route C

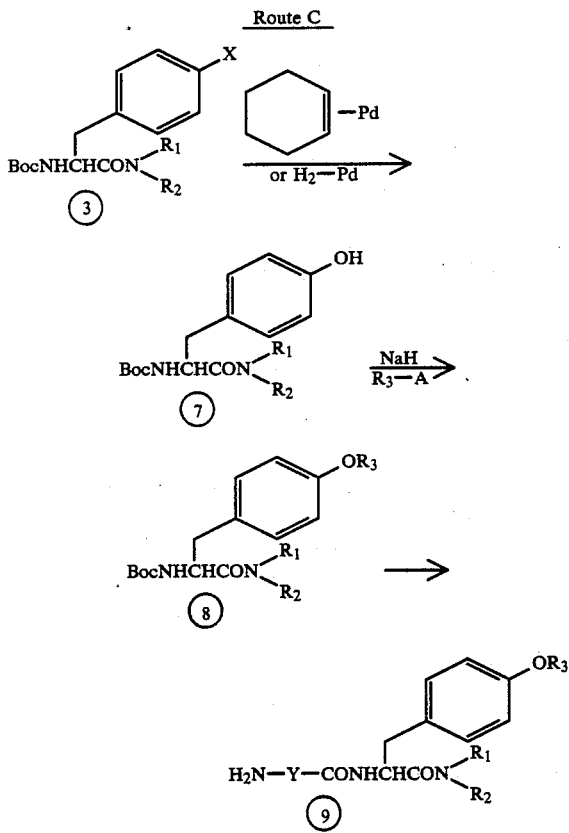

For syntheses from 3 to 7, there may be employed, for example, the methods as described in synthesis 685 (1976), J. Chem. Soc. Perkin Trans 1 490 (1977).

For synthesis from ⑦ to ⑧, ⑦ is dissolved in an appropriate solvent such as DMF, DMSO, toluene, and the like, and NaH is added in an amount of 1 equivalent to 5 equivalents, preferably 1 equivalent to 2 equivalents relative to ⑦. To this reaction mixture is added a solution of $R_3$-A dissolved in the solvent used as the reaction solvent, and the reaction is carried out at room temperature from 2 hours to 50 hours, preferably from 4 to 6 hours. Then, after a conventional post-treatment, ⑧ is obtained. For synthesis ⑧ to ⑨, the methods from ③ to ⑥ in route A may be used.

EXAMPLES

The present invention will now be further illustrated by, but is by no means limited to, the following Examples. In the following, preparation of typical compounds is described by referring to specific examples.

EXAMPLE 1

Synthesis of N-(trans-4-aminomethylcyclohexylcarbonyl)-L-phenylalanine 4-acetylanilide (Compound No. 2)

N-(t-butyloxycarbonyl)-L-phenylalanine (I) (5.30 g) was dissolved in dry tetrahydrofuran (80 ml), triethylamine (3 ml) was added to the resultant solution and ethyl chlorocarbonate (2.40 g) was added to the mixture under ice-cooling, followed by stirring for 30 minutes. To this solution was added 4-acetylaniline (2.70 g) and the mixture was stirred at room temperature for 10 hours. To the reaction mixture was added ice-water (300 ml) and the precipitated crystalline substance was collected by filtration, thoroughly washed and dried to give 7.07 g of N-(t-butyloxycarbonyl)-L-phenylalanine 4-acetylanilide (II).

To the above compound (II) (2.29 g) was added under ice-cooling 4N-hydrogen chloride/dioxane solution (30 ml) and ice-cooling was removed, followed by stirring at room temperature for 30 minutes. To this solution was added ether (300 ml) and the precipitated crystalline substance was collected by filtration, washed with ether and dried under a reduced pressure to quantitatively obtain L-phenylalanine 4-acetylanilide hydrochloride (III).

On the other hand, trans-4-(t-butyloxycarbonyl) aminomethylcyclohexylcarboxylic acid (1.62 g) was dissolved in dry tetrahydrofuran (50 ml), triethylamine (0.96 ml) was added to the resultant solution and ethyl chlorocarbonate (0.76 g) was added under ice-cooling to the mixture, followed by stirring for 30 minutes. To this solution was added the hydrochloride salt (III) previously obtained and triethylamine (2 ml) was added to the mixture, followed by stirring at room temperature for 3 hours. Ice-water (200 ml) was added to the reaction mixture and the precipitated crystalline substance was collected by filtration, thoroughly washed with water and dried to give 2.62 g of N-[trans-4-(t-butyloxycarbonyl)aminomethylcyclohexylcarbonyl]-L-phenylalanine 4-acetylanilide (IV).

To the above compound (IV) (2.60 g) was added under ice-cooling 4N-hydrogen chloride/dioxane solution (25 ml) and the mixture was stirred at room temperature for 30 minutes. The mixture was concentrated under a reduced pressure, and the residue was dissolved in water (100 ml) and sodium carbonate (1.05 g) was added to the resultant solution. The precipitated crystalline substance was collected by filtration, thoroughly washed with water and dried to obtain N-(trans-4-aminomethylcyclohexylcarbonyl)-L-phenylalanine 4-acetylanilide (V) (1.90 g).

EXAMPLE 2

Synthesis of N-(trans-4-aminomethylcyclohexylcarbonyl)-4-benzyloxy-L-phenylalanine 4-acetylanilide (Compound No. 3)

Trans-4-(t-butyloxycarbonyl)aminomethylcyclohexylcarboxylic acid (1.41 g) was made into a mixed acid anhydride following a conventional method, and 4-benzyloxy-L-phenylalanine-4-acetylanilide hydrochloride previously synthesized following a conventional method was added thereto and the mixture was stirred with addition of triethylamine (1.7 ml) at room temperature for 3 hours. Then, post-treatment was carried out following the procedure as described in Example 1 to give N-[trans-4-(t-butyloxycarbonyl)aminomethylcyclohexylcarbonyl]-4-benzyloxy-L-phenylalanine 4-acetylanilide (I) (2.46 g).

The above compound (I) (2.40 g) was treated with 4N-hydrogen chloride/dioxane and, following the procedure of Example 1, N-(trans-4-aminomethylcyclohexylcarbonyl)-4-benzyloxy-L-phenylalanine 4-acetylanilide (II) (1.50 g) was obtained.

EXAMPLE 3

Synthesis of N-(trans-4-aminomethylcyclohexylcarbonyl)-4-hydroxy-L-phenylalanine 4-acetylanilide (Compound No. 4)

Ethanol was added to the N-(trans-4-aminomethylcyclohexyl-carbonyl)-4-benzyloxy-L-phenylalanine 4-acetylanilide prepared in Example 2 (100 mg), palladium black (20 mg) and cyclohexene (2.5 ml) and the mixture was stirred under reflux of ethanol for 30 minutes. The solid was collected by filtration, and concentrated to obtain N-(trans-4-aminomethylcyclohexylcarbonyl)-4-hydroxy-L-phenylalanine 4-acetylanilide (79 mg).

EXAMPLE 4

Synthesis of N-(trans-4-aminomethylcyclohexylcarbonyl)-4-(4-chlorobenzyloxy)-L-phenylalanine 4-acetylanilide (Compound No. 5)

A mixture of N-(t-butyloxycarbonyl)-4-benzyloxy-L-phenylalanine 4-acetylanilide (I) (4.88 g), palladium black (0.60 g), cyclohexene (15 ml) and ethanol (100 ml) was subjected to the reaction under reflux of ethanol for 1 hour. After cooling, the solid was filtered off and the filtrate was concentrated to obtain N-(t-butyloxycarbonyl)-4-hydroxy-L-phenylalanine 4-acetylanilide (II) (3.90 g). The compound (II) without purification was dissolved in N,N-dimethylformamide (100 ml) and the solution was stirred with addition of sodium hydride (60% content) (0.44 g) at room temperature for 30 minutes. To this solution was added 4-chlorobenzyl chloride (1.61 g) and the reaction was carried out at room temperature for 10 hours. Ice-water (500 ml) was added to the reaction mixture, and the precipitated crystalline substance was collected by filtration, thoroughly washed with water and dried to obtain N-(t-butyloxycarbonyl)-4-(4-chlorobenzyloxy)-L-phenylalanine 4-acetylanilide (III) (3.65 g). The compound (III) was treated in a conventional manner to synthesize N-(trans-4-aminomethylcyclohexylcarbonyl)-4-(4-chlorobenzyloxy)-L-phenylalanine 4-acetylanilide (IV).

EXAMPLE 5

Synthesis of N-(trans-4-aminomethylcyclohexylcarbonyl)-4-methoxy-L-phenylalanine 4-acetylanilide (Compound No. 6)

N-(t-butoxycarbonyl)-4-benzyloxy-L-phenylalanine 4-acetylanilide (0.49 g), palladium black (0.10 g) and cyclohexene (4 ml) were reacted with ethanol (20 ml) under reflux for 1 hour. After cooling, the solid was filtered off and the filtrate was concentrated under reduced pressure to obtain N-(t-butyloxycarbonyl)-4-hydroxy-L-phenylalanine 4-acetylanilide (I) (0.39 g).

The compound (I) was dissolved in dimethylformamide (6 ml) and oily sodium hydride (0.04 g) was added to the resultant solution. The mixture was stirred at room temperature for 30 minutes. To this mixture was added a dimethylformamide (2 ml) solution of methyl iodide (0.15 g) and the reaction was carried out at room temperature for 6 hours. Ice-water was added to the reaction mixture, and the resultant oily substance was extracted with ethyl acetate. After a conventional treatment, N-(t-butyloxycarbonyl)-4-methoxy-L-phenylalanine 4-acetylanilide (II) (0.21 g) was obtained. N-(trans-4-aminomethyl cyclohexylcarbonyl)-4-methoxy-L-phenylalanine 4-acetylanilide (0.08 g) was obtained from the compound (II) (0.19 g), following the procedure of Example 1.

EXAMPLE 6

Synthesis of N-(4-aminomethylbenzoyl)-4-hydroxy-L-phenylalanine 4-benzoylanilide (Compound No. 10)

N-(4-benzyloxycarbonylaminomethylbenzoyl)-4-benzyloxy-L-phenylalanine 4-benzoylanilide (I) (0.20 g) was dissolved in 30% hydrobromic acid/acetic acid solution (10 ml) and the solution was stirred at room temperature for 30 minutes. Excessive reagent was removed with ether by decantation, water was added to the residue and the mixture was made alkaline with sodium carbonate, followed by extraction with methylene chloride. According to a conventional method, N-(4-aminomethylbenzoyl)-4-hydroxy-L-phenylalanine 4-benzoylanilide (II) (0.11 g) was obtained.

EXAMPLE 7

Synthesis of N-(trans-4-aminomethylcyclohexylcarbonyl)-4-benzyloxy-L-phenylalanine 3-pyridylamide dihydrochloride (Compound No. 16)

N-(t-butyloxycarbonyl)-4-benzyloxy-L-phenylalanine (I) (3.71 g) was dissolved in dry tetrahydrofuran (100 ml) and, under ice cooling, triethylamine (1.5 ml) was added thereto. After stirring for 15 minutes, ethyl chlorocarbonate (1.10 g) was added, followed by stirring for 30 minutes. To this solution was added 3-aminopyridine (0.94 g) and the reaction was carried out at room temperature for 7 hours. The solid was filtered off and the filtrate was concentrated under reduced pressure. The residue was extracted with ethyl acetate. After a conventional post-treatment, N-(t-butyloxycarbonyl)-4-benzyloxy-L-phenylalanine 3-pyridylamide (II) (1.01 g) was obtained.

The compound (II) (0.90 g) was dissolved in dry 1,4-dioxane (10 ml) and, to this solution, 4N hydrogen chloride/dioxane solution (25 ml) was added and, at room temperature, the mixture was stirred for 1 hour. The precipitated substance was collected by filtration. This product was added to a mixed acid anhydride, which was previously synthesized from 4-(t-butyloxycarbonyl)aminomethyl cyclohexyl carboxylic acid (0.54 g), triethylamine (0.31 ml), and ethyl chlorocarbonate (0.23 g). Furthermore, to this mixture were added triethylamine (0.62 ml) and N,N-dimethylformamide (5 ml) followed by stirring at room temperature for 3 hours. To the reaction mixture was added ice-water (100 ml) and the precipitated substance was collected by filtration. After thoroughly washing with water and drying, N-(trans-4-(t-butyloxycarbonyl)aminomethylcyclohexylcarbonyl-4-benzyloxy-L-phenylalanine 3-pyridylamide (III) (0.98 g) was obtained.

The compound (III) (0.95 g) was dissolved in dry 1,4-dioxane (10 ml) and, to this solution, 4N-hydrogen chloride/dioxane solution (20 ml) was added, followed by stirring at room temperature for 2 hours. The precipitated substance was collected by filtration and dried to obtain N-(trans-4-aminomethylcyclohexylcarbonyl)-4-benzyloxy-L-phenylalanine 3-pyridylamide dihydrochloride (0.90 g).

EXAMPLE 8

Synthesis of N-(trans-4-aminomethylcyclohexylcarbonyl)-4-phenacyloxy-L-phenylalanine cyclohexylamide hydrochloride (Compound 23)

A mixture of N-(t-butyloxycarbonyl)-4-benzyloxy-L-phenylalanine cyclohexylamide (0.68 g) obtained in Example 4, palladium black (0.10 g), cyclohexene (4 ml), and ethanol (20 ml) was allowed to react under reflux of ethanol for one hour, while stirring. After cooling, the solid was filtered off and the filtrate was concentrated under reduced pressure to obtain N-(t-butyloxycarbonyl-4-hydroxy-L-phenylalanine cyclohexylamide (I) (0.54 g). The compound (I) (0.54 g) was dissolved, without purification, in N,N-dimethylformamide (10 ml), followed by adding sodium hydride (0.06 g) thereto. The mixture was stirred at room temperature for 30 minutes. To this solution was added a solution of phenacyl bromide (0.30 g) in N,N-dimethylformamide (5 ml). The reaction was carried out at room temperature for 4 hours, followed by adding ice-water thereto. The resultant oily product was extracted with ethyl acetate. After a conventional post-treatment, N-(t-butyloxycarbonyl)-4-phenacyloxy-L-phenylalanine cyclohexylamide (II) (0.61 g) was obtained. From the compound (II), N-(trans-4-aminomethylcyclohexylcarbonyl)-4-phenacyloxy-L-phenylalanine cyclohexylamide hydrochloride (0.38 g) was obtained, following the procedure of Example 7.

EXAMPLE 9

Synthesis of N-(trans-4-aminomethylcyclohexylcarbonyl)-4-nitro-D,L-phenylalanine 4-benzoylanilide hydrochloride (Compound No. 31)

N-(t-butyloxycarbonyl)-4-nitro-D,L-phenylalanine (0.95 g) and triethylamine (0.4 ml) were dissolved in dry tetrahydrofuran (15 ml), and ethylchorocarbonate (0.33 g) was added under ice-cooling to the resultant solution, followed by stirring for 20 minutes. 4-benzoylaniline (0.6 g) was added to the solution and the mixture was further stirred at room temperature for 12 hours. According to a conventional post-treatment, 0.98 g of N-(t-butyloxycarbonyl)-4-nitro-D,L-phenylalanine 4-benzoylanilide (I) was obtained. To the above compound (I) (0.37 g) was added 4N-hydrogen chloride/dioxane solution (1.5 ml) and the mixture was stirred at room temperature for 1 hour. The solid precipitated by addition of ethyl ether (10 ml) into this solution was collected by filtration to give 0.33 g of 4-nitro-D,L-phenylalanine 4-benzoylanilide hydrochloride (II). Trans-4-(t-butyloxycarbonyl)aminomethylcyclohexylcarboxylic acid (0.2 g) and triethylamine (0.2 ml) were dissolved in dry tetrahydrofuran (15 ml) and ethyl chlorocarbonate (0.09 g) was added to the solution under ice-cooling, followed by stirring for 20 minutes. To this solution was added the above compound (II) (0.33 g) and the mixture as stirred at room temperature for 12 hours. According to a conventional post-treatment, 0.29 g of N-[trans-4-(t-butyloxycarbonyl)aminomethylcyclohexylcarbonyl]-4-nitro-D,L-phenylalanine 4-benzoylanilide (III) was obtained. The above compound (III) (0.29 g) was dissolved in 4N-hydrogen chloride/dioxane solution (1 ml), the solution was stirred at room temperature for 1 hour and then ether (8 ml) was added. The crystalline substance precipitated was collected by filtration and subjected to a conventional post-treatment, whereby 0.24 g of N-(trans-4-aminomethylcyclohexylcarbonyl)-4-nitro-D,L-phenylalanine 4-benzoylanilide hydrochloride was obtained.

EXAMPLE 10

Synthesis of
N-(trans-4-aminomethylcyclohexylcarbonyl)-4-benzyloxy-L-phenylalanine
4-cis/trans-methylcyclohexylamide hydrochloride
(Compound No. 34)

Triethylamine (1.5 ml) was added to a solution of N-(t-butyloxycarbonyl)-4-benzyloxy-L-phenylalanine (I) (2.0 g) dissolved in dry tetrahydrofuran (30 ml) and ethyl chlorocarbonate (0.65 g) was added under ice-cooling, followed by stirring for 30 minutes.

To this solution was added 4-cis/trans-methylcyclohexylamine (0.43 g) and the mixture was stirred at room temperature for 10 hours. After evaporation of the solvent, the residue was extracted with ethyl acetate washed with water and dried to give 2.3 g of N-(t-butyloxycarbonyl)-4-benzyloxy-L-phenylalanine 4-cis/trans-methylcyclohexylamide (II).

To the above compound (II) (1.0 g) was added under ice-cooling 4N-hydrogen chloride/dioxane solution (4.5 ml) and the mixture was stirred at room temperature for 30 minutes. Hexane (30 ml) was added to this solution and the precipitated crystalline substance was collected by filtration, washed with ether and then dried under reduced pressure to give quantitatively 4-benzyloxy-L-phenylalanine 4-cis/trans-methylcyclohexylamide hydrochloride (III). On the other hand, triethylamine (0.6 ml) was added to a solution of trans-4-(t-butyloxycarbonyl)aminomethylcyclohexylcarboxylic acid (0.62 g) dissolved in dry tetrahydrofuran (30 ml) and ethyl chlorocarbonate (0.25 g) was added under ice-cooling, followed by stirring for 30 minutes. To this solution were added the above compound (III) (0.73 g) and triethylamine (1 ml), and the mixture was stirred at room temperature for 3 hours. After evaporation of the solvent, the residue was extracted with ethyl acetate, washed with water and dried to give 0.2 g of N-[trans-4-(t-butyloxycarbonyl)aminomethylcyclohexylcarbonyl]-4-benzyloxyl-L-phenylalanine 4-cis/trans-methylcyclohexylamide (IV). To the above compound (IV) (0.2 g) was added under ice-cooling 4N-hydrogen chloride/dioxane solution (0.5 ml) and the mixture was stirred at room temperature for 30 minutes. Hexane (20 ml) was added to this solution and the precipitated crystalline substance was collected by filtration, washed with ether and then dried under a reduced pressure to give 0.1 g of N-(trans-4-aminomethylcyclohexylcarbonyl)-4-benzyloxy-L-phenylalanine 4-cis/trans-methylcyclohexylamide hydrochloride.

EXAMPLE 11

N-(trans-4-aminomethylcyclohexylcarbonyl)-4-(3-chlorobenzyloxy)-L-phenylalanine 4-acetylanilide methane sulfonate (Compound No. 35)

N-(t-butyloxycarbonyl)-4-(benzyloxy)-L-phenylalanine 4-acetylanilide (1.2 g), palladium black (0.15 g) and cyclohexane (8 ml) were added into ethanol (40 ml) and the reaction was carried out under reflux of ethanol for 1 hour. After cooling, the mixture was filtered and a filtrate was concentrated under a reduced pressure to obtain N-(t-butyloxycarbonyl)-4-hydroxy-L-phenylalanine 4-acetylanilide (I) (0.99 g). The above compound (I) (0.99 g) was dissolved in dimethylformamide (30 ml), added with oily sodium hydride (0.1 g) and the mixture was stirred at room temperature for 30 minutes. A solution of 3-chlorobenzylchloride (0.4 g) in dimethylformamide (5 ml) was allowed to react at room temperature for 6 hours, and the reaction mixture was poured into ice-water (100 ml) and extracted with ethyl acetate. A conventional post-treatment was carried out to obtain N-(t-butyloxycarbonyl)-4-(3-chlorobenzyloxy(-L-phenylalanine 4-acetylanilide (II) (1.25 g). The above compound (II) (1.25 g) was allowed to react with 4N-hydrogen chloride/dioxane (12 ml) to obtain 4-(3-chlorobenzyloxy)-L-phenylalanine 4-acetylanilide (III). The above compound (III) was suspended in dimethylformamide (10 ml)-tetrahydrofuran (10 ml) dry solution, and triethylamine (0.4 ml) and trans-4-(t-butyloxycarbonyl)aminomethylcyclohexylcarboxylic acid mixed acid anhydride were added under ice-cooling, followed by stirring for 30 minutes. Further, the reaction was carried out at room temperature for 3 hours. After a conventional post-treatment, N-[trans-4-(t-butyloxycarbonyl)aminomethylcyclohexylcarbonyl]-4-(3-chlorobenzyloxy)-L-phenylalanine 4-acetylanilide (IV) (1.31 g) was obtained. The above compound (IV) (1.31 g) was allowed to react with 4N-hydrogen chloride/dioxane solution (10 ml) for 1 hour, and the crystalline substance precipitated by addition of hexane was collected by filtration. This was dissolved in water (100 ml) and the substance preipitated by addition of sodium carbonate was suspended in methanol (30 ml)-methylenechloride (30 ml) solution and methanesulfonic acid (0.13 g) was added to the suspension, followed by stirring at room temperature for 1 hour, to obtain a transparent solution. After evaporation of the solvent under reduced pressure, recrystallization from ethanol-ether solution gave N-(trans-4-aminomethylcyclohexylcarbonyl)-4-(3-chlorobenzyloxy)-L-phenylaline 4-acetylanilidemethanesulfonate (1.1 g).

EXAMPLE 12

Synthesis of
N-(trans-4-aminomethylcyclohexylcarbonyl)-4-benzyloxy-L-phenylalanine 4-sulfamoylanilide
hydrochloride (Compound No. 47)

Triethylamine (1.5 ml) was added to a solution of N-(t-butyloxycarbonyl)-4-benzyloxy-L-phenylalanine (I) (2 g) dissolved in dry tetrahydrofuran (30 ml) and ethyl chlorocarbonate (0.65 g) was added under ice-cooling, followed by stirring for 30 minutes. To this solution was added 4-sulfamoylaniline (0.65 g) and the mixture was stirred at room temperature for 10 hours. Post-treatment was carried out in the same manner as in Example 1 to give 1.3 g of N-(t-butyloxycarbonyl)-4-benzyloxy-L-phenylalanine 4-sulfamoylanilide (II). To the above compound (II) (0.5 g) was added under ice-cooling 4N-hydrogen chloride/dioxane solution (3 ml) and the mixture was stirred at room temperature for 30 minutes. Post-treatment conducted in the same manner as in Example 1 gave quantitatively 4-benzyloxy-L-phenylalanine 4-sulfamoylanilide hydrochloride (III). On the other hand, trans-4-(t-butyloxycarbonyl- )aminomethylcyclohexylcarboxylic acid (0.25 g) and triethylamine (0.2 ml) were added, and ethyl chlorocarbonate (0.1 g) was added under ice-cooling, followed by stirring for 30 minutes. To this solution were added the above compound (III) (0.42 g) and triethylamine (1 ml), and the mixture was stirred at room temperature for 3 hours. After extraction with chloroform, according to the same post-treatment as in Example 1, 0.28 g of N-[trans-4-(t-butyloxycarbonyl)aminomethylcyclohexylcarbonyl]-4-benzyloxy-L-phenylalanine 4-sulfamoylanilide (IV) was obtained. To the above compound (IV) (0.28 g) was added 4N-hydrogen chloride/dioxane solution (2 ml) and, after stirring at room temperature for 30 minutes, following the same procedure as in Example 1, 0.15 g of N-(trans-4-aminomethylcyclohexylcarbonyl)-4-benzyloxy-L-phenylalanine 4-sulfamoylanilide hydrochloride was obtained.

EXAMPLE 13

Synthesis of
N-(trans-4-aminomethylcyclohexylcarbonyl)-4-benzyloxy-L-phenylalanine 4-(2-chloro)pyridylamide hydrochloride (Compound No. 59)

N-(t-butyloxycarbonyl)-4-benzyloxy-L-phenylalanine (I) (4.46 g) was dissolved in dry tetrahydrofuran (110 ml) and triethylamine (1.80 ml) was added under ice-cooling, followed by stirring for 15 minutes. To this solution was added ethyl chlorocarbonate (1.44 g) and the mixture was stirred for 30 minutes. After adding 4-amino-2-chloropyridine (1.54 g), the reaction was carried out at room temperature for 10 hours. The solid was filtered off and the filtrate was concentrated under a reduced pressure. The residue was extracted with ethyl acetate. The extract was purified with a column chromatography to obtain N-(t-butyloxycarbonyl)-4-benzyloxy-L-phenylalanine 4-(2-chloro)pyridylamide (II) (0.60 g). Following the procedure of Example 7, the final compound N-(trans-4-aminomethylcyclohexylcarbonyl)-4-benzyloxy-L-phenylalanine 4-(2-chloro)-pyridylamide hydrochloride (III) (0.67 g) was obtained from the compound (II).

EXAMPLE 14

Synthesis of
N-(trans-4-aminomethylcyclohexylcarbonyl)-4-(4-toluenesulfonyloxy(-L-phenylalanine 4-acetylanilide hydrochloride (Compound No. 79)

N-(t-butyloxycarbonyl)-4-hydroxy-L-phenylalanine 4-acetylanilide (0.57 g) and triethylamine (0.5 ml) were dissolved in dichloromethane (10 ml)-tetrahydrofuran (10 ml) solution and 4-toluenesulfonyl chloride (0.38 g) was added at room temperature, followed by stirring for 3 hours. According to a conventional post-treatment, N-(t-butyloxycarbonyl)-4-(4-toluenesulfonyloxy(-L-phenylalanine 4-acetylanilide (I) (0.8 g) was obtained. The above compound (I) (0.8 g) was treated with 4N hydrogen chloride/dioxane solution (2.2 ml) to obtain 4-(4-toluenesulfonyloxy)-L-phenylalanine 4-acetylanilide hydrochloride (II) (0.7 g). On the other hand, trans-4-(t-butyloxycarbonyl)aminomethylcyclohexylcarboxylic acid (0.37 g) and triethylamine (0.4 ml) were dissolved in dry tetrahydrofuran (20 ml) and ethylchlorocarbonate (0.16 g) was added under ice-cooling, followed by stirring for 20 minutes. To this solution was added the above compound (II) (0.7 g) and the mixture was stirred at room temperature for 12 hours. According to a conventional post-treatment N-[trans-4-(t-butyloxycarbonyl)aminomethylcyclohexylcarbonyl]-4-(4-toluenesulfonyloxy)-L-phenylalanine 4-acetylanilide (III) (0.32 g) was obtained. The above compound (III) (0.32 g) was treated with 4N-hydrogen chloride/dioxane solution (1 ml) to obtain N-(trans-4-aminomethylcyclohexylcarbonyl)-4-(4-toluenesulfonyloxy)-L-phenylalanine 4-acetylanilide hydrochloride (0.2 g).

EXAMPLE 15

N-(4-aminomethylbenzoylcarbonyl)-4-benzyloxy-L-phenylalanine 3,4-dimethylcyclohexylamide hydrochloride (Compound No. 80)

N-(t-butyloxycarbonyl)-4-benzyloxy-L-phenylalanine (0.3 g) and 3,4-dimethylcyclohexylamine (0.1 g) were dissolved in dry methylene chloride (30 ml) and 1-ethyl-3-(3-dimethylaminopropyl)carbodiimide hydrochloride (0.2 g) was added to the solution, followed by stirring at room temperature for 12 hours. According to a conventional post-treatment, N-(t-butyloxycarbonyl)-4-benzyloxy-L-phenylalanine 3,4-dimethylcyclohexylamide (I) (0.32 g) was obtained. The above compound (I) (0.3 g) was allowed to react with 4N-hydrogen chloride/dioxane solution to obtain 4-benzyloxy-L-phenylalanine 3,4-dimethylcyclohexylamide hydrochloride (II) (0.26 g). The above compound (II) (0.26 g) and 4-(t-butyloxycarbonyl)aminomethylbenzoic acid (0.16 g) were dissolved in dry methylene chloride (20 ml)-pyridine solution, and 1-ethyl-3-(3-dimethylaminopropyl)-carbodiimide hydrochloride (0.15 g) was added to the solution. The reaction was carried out at room temperature for 12 hours. After a conventional post-treatment, N-[4-(t-butyloxycarbonyl)aminomethylbenzoyl]-4-benzyloxy-L-phenylalanine 3,4-dimethylcyclohexylamide (III) (0.23 g) was obtained. The above compound (III) was allowed to react with 4N-hydrogen chloride/dioxane solution to (2 ml) obtain N-(4-aminomethylbenzoyl)-4-benzyloxy-L-phenylalanine 3,4-dimethylcyclohexylamide hydrochloride (0.18 g).

EXAMPLE 16

Synthesis of
N-(trans-4-aminomethylcyclohexylcarbonyl)-4-(4-nitrophenyloxy)- L-phenylalanine 4-acetylanilide hydrochloride (Compound No. 95)

To a solution of N-(t-butyloxycarbonyl)-4-hydroxy-L-phenylalanine 4-acetylanilide (1.59 g) in dimethyl sulfoxide (10 ml) were added potassium hydroxide (0.25 g) and 4-nitrobromobenzene (0.81 g), and the mixture was heated at 80°–90° C. and stirred for 10 hours. After conventional post-treatment N-(t-butyloxycarbonyl)-4-(4-nitrophenyloxy)-L-phenylalanine 4-acetylanilide (I) (0.62 g) was obtained. The above compound (I) (0.6 g) was allowed to react with 4N-hydrogen chloride/dioxane solution to obtain 4-(4-nitrophenyloxy-L-phenylalanine 4-acetylanilide hydrochloride, which was further allowed to react with trans-4-(t-butyloxycarbonyl- )aminomethylcyclohexylcarboxylic acid mixed acid anhydride obtained in Example 5 to obtain N-[trans-4-(t-butyloxycarbonyl)aminomethylcyclohexylcarbonyl]-4-(4-nitrophenyloxy)-L-phenylalanine 4-acetylanilide (II) (0.54 g). The above compound (II) (0.54 g) was allowed to react with 4N-hydrogen chloride/dioxane solution to obtain N-(trans-4-aminomethylcyclohexylcarbonyl)-4-(4-nitrophenoxy)-L-phenylalanine 4-acetylanilide hydrochloride (0.39 g).

EXAMPLE 17

Synthesis of N-(4-aminomethylbenzoyl)-4-benzyloxy-L-phenylalanine 4-picolylamide dihydrochloride (Compound No. 96)

N-(t-butyloxycarbonyl)-4-benzyloxy-L-phenylalanine (I) (2.00 g) was dissolved in dry tetrahydrofuran (50 ml) and, under ice-cooling, triethylamine (0.81 ml) was added thereto. After stirring for 15 minutes, ethyl chlorocarbonate (0.64 g) was added thereto, followed by stirring for 30 minutes. To this solution was added 4-picolylamine (0.58 g) and the mixture was stirred at room temperature for 5 hours. The solid was filtered off and the filtrate was concentrated under reduced pressure. The residue was extracted with ethyl acetate. After a conventional post-treatment N-(t-butyloxycarbonyl)-4-benzyloxy-L-phenylalanine 4-picolylamide (II) (1.60 g) was obtained. To the compound (II) (1.60 g) 4N-hydrogen chloride/dioxane solution (15 ml) was added, followed by stirring at room temperature for 30 minutes. The precipitated substance was collected by filtration and dried to quantitatively obtain 4-benzyloxy-L-phenylalanine 4-picolylamide dihydrochloride (III).

On the other hand, N-4-(t-butyloxycarbonyl)aminomethyl benzoic acid (0.60 g) was dissolved in dry tetrahydrofuran (10 ml) and N,N-dimethylformamide (5 ml) and, under ice-cooling, triethylamine (1.20 ml) was added thereto. After stirring for 15 minutes, ethyl chlorocarbonate (0.29 g) was added thereto, followed by stirring for 30 minutes. To this solution was added the above-prepared compound (III), followed by stirring for 3 hours at room temperature. The solid was filtered off and the filtrate was concentrated under reduced pressure. The residue was extracted with ethyl acetate and, after a conventional post-treatment, N-4-(t-butyloxycarbonyl)aminomethylbenzoyl-4-benzyloxy-L- phenylalanine 4-picolylamide (IV) (0.45 g) was obtained. To this compound (IV) (0.45 g) was added 4N hydrogen chloride/dioxane solution (4.5 ml) and the precipitated substance was collected by filtration. After drying, N-(4-aminomethylbenzoyl)-4-benzyloxy-L-phenylalanine 4-picolylamide dihydrochloride (0.39 g) was obtained.

EXAMPLE 18

Synthesis of N-(4-aminomethylbenzoyl)-4-benzyloxy-L-phenylalanine cyclohexylamide hydrochloride (Compound No. 114)

N-(t-butyloxycarbonyl)-4-benzyloxy-L-phenylalanine (I) (2.0 g) dissolved in dry tetrahydrofuran (30 ml) and ethyl chlorocarbonate (0.65 g) was added under ice-cooling, followed by stirring for 30 minutes.

To this solution was added cychlohexylamine (0.43 g) and the mixture was stirred at room temperature for 10 hours. After evaporation of the solvent, the residue was extracted with ethyl acetate, washed with water, and dried to obtain 2.3 g of N-(t-butyloxycarbonyl)-4-benzyloxy-L-phenylalanine cyclohexylamide (II).

To the above compound (II) (1.0 g) was added under ice-cooling 4N-hydrogen chloride/dioxane solution (4.5 ml) and the mixture was stirred at room temperature for 30 minutes. Hexane (30 ml) was added to this solution and the precipitated crystalline substance was collected by filtration, washed with ether and then dried under reduced pressure to quantitatively obtain 4-benzyloxy-L-phenylalanine cyclohexylamide hydrochloride (III). On the other hand, triethylamine (0.6 ml) was added to 4-(t-butyloxycarbonyl)aminomethylbenzoic acid (0.62 g) dissolved in dry tetrahydrofuran (30 ml) and ethyl chlorocarbonate (0.25 g) was added under ice-cooling, followed by stirring for 30 minutes. To this solution were added the above compound (III) (0.73 g) and triethylamine (1 ml), and the mixture was stirred at room temperature for 3 hours. After evaporation of the solvent, the residue was extracted with ethyl acetate, washed with water and dried to obtain 0.2 g of N-[4-(t-butyloxycarbonyl)aminomethylbenzoyl]-4-benzyloxy-L-phenylalanine cyclohexylamide (IV). To the above compound (IV) (0.2 g) was added under ice-cooling 4N-hydrogenchloride/dioxane solution (0.5 ml) and the mixture was stirred at room temperature for 30 minutes. Hexane (20 ml) was added to this solution and the precipitated crystalline substance was collected by filtration, washed with ether and then dried under reduced pressure to obtain 0.1 g of N-(4-aminomethylbenzoyl)-4-benzyloxy-L-phenylalanine cyclohexylamide hydrochloride.

EXAMPLE 19

Synthesis of N-(trans-4-aminomethylcyclohexylcarbonyl)-4-benzyloxy-L-phenylalanine 4-trifluoromethylanilide hydrochloride (Compound No. 119)

Triethylamine (1.5 ml) was added to a solution of N-(t-butyloxycarbonyl)-4-benzyloxy-L-phenylalanine (I) (2 g) dissolved in dry tetrahydrofuran (30 ml) and ethyl chlorocarbonate (0.65 g) was added under ice-cooling, followed by stirring for 30 minutes. To this solution was added 4-trifluoromethylaniline (0.65 g) and the mixture was stirred at room temperature for 10 hours. Post-treatment was carried out in the same manner as in Example 1 to obtain 1.3 g of N-(t-butyloxycarbonyl)-4-benzyloxy-L-phenylalanine 4-trifluoromethylanilide (II). to the above compound (II) (0.5 g) was added under ice-cooling 4N-hydrogen chloride/dioxane solution (3 ml) and the mixture was stirred at room temperature for 30 minutes. Post-treatment conducted in the same manner as in Example 1 gave quantitatively 4-benzyloxy-L-phenylalanine 4-trifluoromethylanilide (III). On the other hand, trans-4-(t-butyloxycarbonyl)aminomethylcyclohexylcarboxylic acid (0.25 g) and triethylamine (0.2 ml) were added, and ethylchlorocarbonate (0.1 g) was added under ice-cooling, followed by stirring for 30 minutes. To this solution were added the above compound (III) (0.42 g) and triethylamine (1 ml), and the mixture was stirred at room temperature for 3 hours. After extraction with chloroform, according to the same post-treatment as in Example 1, 0.28 g of N-[trans-4-(t-butyloxycarbonyl)aminomethylcyclohexyl-carbonyl]-4-benzyloxy-L-phenylalanine 4-trifluoromethylanilide (IV) was obtained. To the above compound (IV) (0.28 g) was added 4N-hydrogen chloride/dioxane solution (2 ml) and, after stirring at room temperature for 30 minutes, following the same procedure as in Example 1, 0.15 g of N-(trans-4-aminomethylcyclohexyl-carbonyl)-4-benzyloxy-L-phenylalanine 4-trifluoromethylanilide hydrochloride was obtained.

EXAMPLE 20

Synthesis of N-(trans-4-aminomethylcyclohexylcarbonyl)-4-(5-nitro-2-pyridyloxy)-L-phenylalanine 4-acetylanilide hydrochloride (Compound No. 121)

To a solution of N-(t-butyloxycarbonyl)-4-hydroxy-L-phenylalanine 4-acetylanilide (0.57 g) in dry dimethylsulfoxide (10 ml) was added oily sodium hydride (0.07 g), followed by stirring at room temperature for 30 minutes. Then, 2-chloro-5-nitropyridine (0.28 g) was added and stirred at room temperature for 10 hours. After a conventional post-treatment, N-(t-butyloxycarbonyl)-4-(5-nitro-2-pyridyloxy-L-phenylalanine 4-acetylanilide (I) (0.70 g) was obtained. The above compound (I) (0.70 g) was treated with 4N hydrogen chloride/dioxane solution (15 ml) to obtain 4-(5-nitro-2-pyridyloxy)-L-phenylalanine 4-acetylanilide hydrochloride (II) (0.65 g).

On the other hand, trans-4-(t-butyloxycarbonyl) aminomethylcyclohexylcarboxylic acid (0.37 g) and triethylamine (0.4 ml) were dissolved in dry tetrahydrofuran (20 ml) and ethyl chlorocarbonate (0.16 g) was added under ice-cooling, followed by stirring for 20 minutes. To this solution was added the above comnpound (II) (0.65 g) and, after neutralizing with triethylamine, the mixture was stirred at room temperature for 12 hours. According to a conventional post-treatment N-[trans-4-(t-butyloxycarbonyl)aminomethylcyclohexylcarbonyl]-4-(5-nitro-2-pyridyloxy)-L-phenylalanine 4-acetylanilide (III) (0.32 g) was obtained. The above compound (III) (0.32 g) was treated with 4N-hydrogen chloride/dioxane solution (1 ml) to obtain N-(trans-4-aminomethylcyclohexylcarbonyl)-4-(5-nitro-2-pyridyloxy)-L-phenylalanine 4-acetylanilide hydrochloride (0.2 g).

EXAMPLE 21

N-(trans-4-aminomethylcyclohexylcarbonyl)-4-(3-cyanobenzyloxy)-L-phenylalanine 4-acetylanilide hydrochloride (Compound No. 122)

N-(t-butyloxycarbonyl)-4-benzyloxy-L-phenylalanine 4-acetylanilide (1.2 g), palladium black (0.15 g) and cyclohexene (8 ml) were added into ethanol (40 ml) and the reaction was carried out under reflux of ethanol for 1 hour. After cooling, the mixture was filtered and a filtrate was concentrated under a reduced pressure to obtain N-(t-butyloxycarbonyl)-4-hydroxy-L-phenylalanine 4-acetylanilide (I) (0.99 g). The above compound (I) (0.99 g) was dissolved in dimethylformamide (30 ml), added with oily sodium hydride (0.1 g) and the mixture was stirred at room temperature for 30 minutes. A solution of 3-cyanobenzylbromide (0.4 g) in dimethylformamide (5 ml) was added and allowed to react at room temperature for 6 hours, and the reaction mixture was poured into ice-water (100 ml) and extracted with ethyl acetate. A conventional post-treatment was carried out to obtain N-(t-butyloxycarbonyl)-4-(3-cyanobenzyloxy)-L-phenylalanine 4-acetylanilide (II) (1.25 g). The above compound (II) (1.25 g) was allowed to react with 4N-hydrogen chloride/dioxane (12 ml) to obtain 4-(3-cyanobenzyloxy)-L-phenylalanine 4-acetylanilide (III).

The above compound (III) was suspended in dimethylformamide (10 ml)—tetrahydrofuran (10 ml) solution, and triethylamine (0.4 ml) and trans-4-(t-butyloxycarbonyl)aminomethylcyclohexylcarboxylic acid mixed acid anhydride were added under ice-cooling, followed by stirring for 30 minutes. Further, the reaction was carried out at room temperature for 3 hours. After a conventional post-treatment, N-[trans-4-(t-butyloxycarbonyl)aminomethylcyclohexylcarbonyl]-4-(3-cyanobenzyloxy)-L-phenylalanine 4-acetylanilide (IV) (1.31 g) was obtained. The above compound (IV) (1.31 g) was allowed to react with 4N-hydrogen chloride/dioxane solution (10 ml) for 1 hour, and the crystalline substance precipitated by addition of hexane was collected by filtration. The product was recrystallized from an ethanol-ether solution to obtain N-(trans-4-aminomethylcyclohexylcarbonyl)-4-(3-cyanobenzyloxy)-L-phenylalanine 4-acetylanilide hydrochloride (1.1 g).

EXAMPLE 22

Synthesis of N-(trans-4-aminomethylcyclohexylcarbonyl)-4-nitro-L-phenylalanine 4-acetylanilide hydrochloride (Comnnpound No. 130)

N-(t-butyloxycarbonyl)-4-nitro-L-phenylalanine (0.95 g) and triethylamine (0.4 ml) were dissolved in dry tetrahydrofuran (15 ml), and ethylchlorocarbonate (0.33 g) was added under ice-cooling to the resultant solution, followed by stirring for 20 minutes. 4-acetyaniline (0.6 g) was added to the solution and the mixture was further stirred at room temperature for 12 hours. According to a conventional post-treatment, 0.98 g of N-(t-butyloxycarbonyl)-4-nitro-L-phenylalanine 4-acetylanilide (I) was obtained.

To the above compound (I) (0.37 g) was added 4N-hydrogen chloride-dioxane solution (1.5 ml) and the mixture was stirred at room temperature for 1 hour. The solid precipitated by addition of ethyl ether (10 ml) into this solution was collected by filtration to give 0.33 g of 4-nitro-L-phenylalanine 4-acetylanilide hydrochloride (II). Trans-4-(t-butyloxycarbonyl)aminomethylcyclohexylcarboxylic acid (0.2 g) and triethylamine (0.2 ml) were dissolved in dry tetrahydrofuran (15 ml) and ethylchlorocarbonate (0.09 g) was added to the solution under ice-cooling, followed by stirring for 20 minutes. To this solution was added the above compound (II)

(0.33 g) and the mixture was stirred at room temperature for 12 hours. According to a conventional post-treatment, 0.29 g of N-[trans-4-(t-butyloxycarbonyl)aminomethylcyclohexylcarbonyl]-4-nitro-L-phenylalanine 4-acetylanilide (III) was obtained. The above compound (III) (0.29 g) was dissolved in 4N-hydrogen chloride/dioxane solution (1 ml), the solution was stirred at room temperature for 1 hour and then ether (8 ml) was added. The crystalline substance precipitated was collected by filtration and subjected to a conventional post-treatment, whereby 0.24 g of N-(trans-4-aminomethylcyclohexylcarbonyl)-4-nitro-L-phenylalanine 4-acetylanilide hydrochloride was obtained.

EXAMPLE 23

Synthesis of
N-(trans-4-aminomethylcyclohexylcarbonyl)-4-(3-chloro-6-nitrophenoxy)-L-phenylalanine 4-pyridylamide dihydrochloride (Compound No. 137)

To a solution of N-(t-butyloxycarbonyl)-4-hydroxy-L-phenylalanine 4-pyridylamide (5.35 g) in dimethyl sulfoxide (100 ml) was added oily sodium hydride (0.62 g), followed by stirring at room temperature for 30 minutes. Thereafter, 2,4-dichloronitrobenzene (2.88 g) was added and stirred at room temperature for 10 hours. After a conventional post-treatment, N-(t-butyloxycarbonyl)-4-(3-chloro-6-nitrophenoxy)-L-phenylalanine 4-pyridylamide dihydrochloride (6.66 g) was obtained. The above compound (I) (6.50 g) was allowed to react with 4N-hydrogen chloride/dioxane solution (50 ml) to obtain 4-(3-chloro-6-nitrophenoxy-L-phenylalanine 4-pyridylamide dihydrochloride, which was further allowed to react with trans-4-(t-butyloxycarbonyl)aminomethylcyclohexylcarboxylic acid mixed acid anhydride obtained in Example 5 to obtain N-[trans-4-(t-butyloxycarbonyl)aminomethylcyclohexylcarbonyl]-4-(3-chloro-6-nitrophenoxy)-L-phenylalanine 4-pyridylamide (II) (7.16 g). The above compound (II) (7.00 g) was allowed to react with 4N-hydrogenn chloride/dioxane solution (150 ml) to obtain N-(trans-4-aminomethylcyclohexylcarbonyl)-4-(3-chloro-6-nitrophenoxy)-L-phenylalanine 4-pyridylamide (6.06 g).

EXAMPLE 24

Synthesis of
N-(trans-4-aminomethylcyclohexylcarbonyl)4-(4-picolyloxy)-L-phenylalanine 4-picpecolylamide (Compound No. 165)

N-(t-butyloxycarbonyl)-4-benzyloxy-L-phenylalanine (I) (1.86 g) was dissolved in dry tetrahydrofuran (30 ml) and, under ice-cooling, triethylamine (0.75 ml) was added thereto. After stirring for 10 minutes, ethyl chlorocarbonate (0.56 g) was added and stirred for 30 minutes. To this solution was added a solution of 4-pipecoline (0.55 g) in dry tetrahydrofuran (5 ml). The ice bath was removed and the reaction was carried out at room temperature for 2 hours. The precipitate was filtered off and the filtrate was concentrated under reduced pressure. To the residue was added water (50 ml), followed by extracting with ethyl acetate. After a conventional post-treatment N-(t-butyloxycarbonyl)-4-benzyloxy-L-phenylalanine 4-pipecolylamide (II) (1.83 g) was obtained.

A mixture of the above compound (II) (1.70 g), palladium black (0.20 g), cyclohexene (6 ml), and ethanol (50 ml) was reacted under reflux of ethanol. After cooling, the solid was filtered off and the filtrate was concentrated to obtain N-(t-butyloxycarbonyl)-4-hydroxy-L-phenylalanine 4-pipecolylamide (III) (1.36 g). The compound (III) was dissolved, without purification, in N,N-dimethylformamide (20 ml). To this solution was added oily sodium hydride (60% content) (0.16 g), followed by stirring at room temperature for 30 minutes. To this solution was added a solution of 4-picolyl chloride (0.50 g) in N,N-dimethylformamide (5 ml) and the reaction was carried out at room temperature for 7 hours. Ice water was added to the reaction mixture and the resultant oily proudct was extracted with ethyl acetate. After a conventional post-treatment, N-(t-butyloxycarbonyl)-4-(4-picolyloxy)-L-phenylalanine 4-pipecolylamide (IV) (1.20 g) was obtained. From the compound (IV), N-(trans-4-aminomethylcyclohexylcarbonyl)-4-(4-picolyloxy)-L-phenylalanine-4-pipecolylamide (0.85 g) following the procedure of Example 6.

The phenylalanine derivatives or the salts thereof according to the present invention, which are an effective component of the proteinase inhibitor of the present invention, have very potent inhibition activities against proteinases such as plasmin, kallikrein, trypsin, and urokinase as shown in the below-mentioned test results. The plasmin inhibition activity is different from the effect exhibited by the antiplasmins of the prior art, when contrasted with known drugs of the prior art such as tranexamic acid or ε-aminocaproic acid which selectively inhibits only plasmin among proteinases. For example, some effective ingredients of the proteinase inhibitor according to the present invention exhibit an inhibition activity against urokinase, which is a plasminogen activating enzyme as is well known. This means that the inhibition of this enzyme can provide preferable hemostatics. On the other hand, some of the proteinase inhibitors according to the present invention inhibit antikallikrein activity and antitrypsin activity. This means that these inhibition activities can provide, together with the antiplasmin activity, a strong antiinflammatory agent. For example, the Compound No. 3 in Table 3 is known as the phenylalamine derivative having the structure similar to that of the present invention (see Pharmazie 39, H, 1, 68,1984). Furthermore, the Compound Nos. 4 and 5 are known as phenylalanine derivatives (see Chem. Abst. 77, 102225j; 86, 39312d; and 80, 92633m).

In the following, antiplasmin activity, antikallikrein activity, antitrypsin activity, antiurokinase activity and antithrombin activity of the present compounds are described in detail by referring to typical test examples.

The measurement methods employed in the following test examples are as described below. The test results are shown in Table 2 by referring to the compound Nos. in the above Table 1 for the compounds of the present invention, and the test results are shown in Table 4 by showing the structures of the compounds in Table 3 for the commercially available antiplasmins as Comparative Examples.

(1) EVALUATION OF ANTIPLASMIN ACTIVITY (i) Determination of inhibition activity for fibrin decomposition An inhibitor sample is dissolved in a 0.18M borate-physiological salt buffer solution (pH=7.4) to make the total volume to 600 μl. To this buffer solution, 200 μl of a 0.2% bovine fibrinogen, 100 μl of a 0.3 casein unit/ml human plasmin solution, and 100 μl of a 50 unit/ml bovine thrombin solution, all dissolved in the above-mentioned buffer, are added at a temperature of 37° C. in a constant temperature bath. Then, the dissolution time of the fibrin mass formed above is determined. Thus, the concentration $I_{50}$ of the inhibitor sample (i.e., 50% inhibition concentration, μmol), at which the dissolution time obtained in the absence of the inhibitor (i.e., about 5 minutes) is extended twice, is determined.

(ii) Determination of inhibition activity for S-2251 decomposition

An inhibitor sample is dissolved in a 0.05M Tris-hydrochloric acid buffer solution (pH=7.4) to make the total volume of 400 μl. To this solution, 50 μl of a 3 mM S-2251 solution is added and the mixture is incubated at a temperature of 37° C. for 5 minutes in a constant temperature bath. Then, 50 μl of a 0.2 casein unit/ml human plasmin is added and the mixture is incubated at a temperature of 37° C. for 4 minutes. Thereafter, the reaction is stopped by adding 50 μl of 50% acetic acid.

The absorbance of p-nitroaniline formed in the reaction mixture is determined at 405 nm. Thus, the concentration $I_{50}$ (μmol) of the inhibitor sample, at which the absorbance is one half (i.e., ½) of that obtained in the absence of the inhibitor, is determined.

(iii) Determination of inhibition activity for fibrinogen

An inhibitor sample is dissolved in a 0.18M borate-physiological salt buffer solution (pH=7.4) to make the total volume to 400 μl. To this solution, 500 μl of a 0.4% bovine fibrinogen solution and 100 μl of a 1 casein unit/ml human plasmin solution, all dissolved in the above-mentioned buffer are added at a temperature of 37° C. in a constant temperature bath. After the mixture is allowed to stand at a temperature of 37° C. for 10 minutes, 3800 μl of the above-mentioned buffer containing 13.2 mM of tranexamic acid and 200 μl of a 50 unit/ml bovine thrombin solution are added to terminate the reaction. The mixture is incubated at a temperature of 37° C. for 15 minutes to form the fibrin. The fibrin clot thus formed is adhered to or wound around a glass rod and is then washed with water. The amount of the remaining fibrinogen is determined according to a tyrosine coloring method using a phenol reagent (see J. Biol. Chem., 73, 627 (1927)). From the amount of the remaining fibrinogen thus determined, the amount of decomposed fibrinogen is calculated. Thus, the concentration $I_{50}$ (μmol) of the inhibitor sample, at which the amount of decomposed fibrinogen is one half (i.e., ½) of that obtained in the absence of the inhibitor sample, is determined.

(2) EVALUATION OF ANTITHROMBIN ACTIVITY (i) Determination of inhibition activity against fibrin formation An inhibitor sample is dissolved in a 0.18M borate-physiological salt buffer solution (pH=7.4) to make the total volume to 500 μl. To this solution, 400 μl of a 0.2% bovine fibrinogen solution and 100 μl of a 4 unit/ml bovine thrombin solution are added at a temperature of 37° C. in a constant temperature bath. Thus, a coagulation time is determined. The inhibitor concentration $I_{50}$ (μmol), at which the coagulation time obtained in the absence of the inhibitor is extended twice, is determined.

(ii) Determination of inhibition activity for S-2238 decomposition

An inhibitor sample is dissolved in a 0.05M Tris-hydrochloric acid buffer solution (pH=8.3) to make a total volume of 400 μl. To this solution, 50 μl of a 0.2 mM S-2238 solution is added and the mixture is incubated at a temperature of 37° C. for 5 minutes in a constant temperature bath. Then, 50 μl of a 0.2 unit/ml bovine thrombin solution is added thereto and the absorbance, at 405 nm, of the p-nitroaniline formed per minute is determined at a temperature of 37° C. by using the so-called initial velocity method. Thus, the concentration $I_{50}$ (μmol) of the inhibitor sample at which the absorbance is one half (i.e., ½) of that obtained in the absence of the inhibitor sample, is determined.

(3) EVALUATION OF ANTITRYPSIN ACTIVITY

Determination of inhibition activity against S-2238 decomposition

An inhibitor sample is dissolved in a 0.05M Tris-imidazole buffer solution (pH=8.1) and 125 μl of a 1 mM S-2238 solution is added to make the total volume to 1.20 ml. The mixture is incubated at a temperature of 37° C. for 5 minutes in a constant temperature bath. To this mixture, 0.05 ml of bovine trypsin is added and the absorbance, at 405 nm, of the p-nitroaniline formed per minute is determined at a temperature of 37° C. by using the so-called initial velocity method. Thus, the concentration $I_{50}$ (μmol) of the inhibitor sample, at which the absorbance is one half (i.e., ½) of that obtained in the absence of the inhibitor sample, is determined.

(4) EVALUATION OF ANTI-PLASMA KALLIKREIN ACTIVITY

Determination of inhibition activity for S-2302 decomposition

An inhibitor sample is dissolved in a 0.05M Tris-hydrochloric acid buffer solution (pH=7.8) to make the total volume to 400 μl. To this solution, 50 μl of a 2 mM S-2302 solution is added and the mixture is incubated at a temperature of 37° C. for 5 minutes in a constant temperature bath. Then, 50 μl of a 0.12 unit/ml human plasma kallikrein is added and the mixture is incubated at a temperature of 37° C. for 5 minutes. Thereafter, 50

μl of 50% acetic acid is added to terminate the reaction. The absorbance of the p-nitroaniline formed in the reaction mixture is measured at 405 nm. Thus, the concentration $I_{50}$ (μmol) of the inhibitor sample, at which the absorbance is one half (i.e., ½) of that obtained in the absence of the inhibitor sample, is determined.

(5) EVALUATION OF ANTIUROKINASE ACTIVITY

Determination of inhibition activity for S-2444 decomposition

An inhibitor sample is dissolved in a 0.05M Tris-hydrochloric acid buffer solution (pH=8.8) to make the total volume to 400 μl. To this solution, 50 μl of a 1 mM S-2444 solution is added and the mixture is incubated at a temperature of 37° C. for 5 minutes in a constant temperature bath. Then, 50 μl of a 500 unit/ml human urokinase is added and the mixture is incubated at a temperature of 37° C. for 5 minutes. Thereafter, 50 μl of 50% acetic acid is added to terminate the reaction. The absorbance of the p-nitroaniline formed in the reaction mixture is measured at 405 nm. Thus, the concentration $I_{50}$ (μmol) of the inhibitor sample, at which the absorbance is one half (i.e., ½) of that obtained in the absence of the inhibitor sample, is determined.

When the compounds of the present invention are used as a medicine, there are no critical limitations to the administration methods. The present proteinase inhibitor can be formulated by any conventional method in pharmaceutics. For example, the present proteinase inhibitor may be applied in any conventional manner including intravenous injection, intramuscular injection, instillation, and oral administration. Although there are no critical limitations to the administration dosage, the suitable dosage is 100 to 1000 mg/day/person, which can be conveniently decreased or increased as desired, as a matter of course.

TABLE 2

| Compound No. | Plasmin | | Thrombin | | Trypsin | Plasma Kallikrein | Urokinase |
|---|---|---|---|---|---|---|---|
| | S-2251 | Fibrin | S-2238 | Fibrinogen | S-2238 | S-2302 | S-2444 |
| 1 | 27 | 40 | >100 | >50 | 0.30 | 1.9 | 11 |
| 2 | 36 | 21 | >1000 | >1000 | 1.3 | 0.85 | 58 |
| 3 | 1.8 | 0.40 | >200 | >100 | 0.77 | 0.63 | 31 |
| 5 | 0.90 | 0.39 | | | 0.84 | 0.46 | 25 |
| 6 | 1.3 | 4.6 | 230 | >500 | 1.1 | 2.0 | 42 |
| 12 | 0.79 | 0.41 | | | | 0.84 | 11 |
| 14 | 168 | 4.4 | >400 | >500 | | 2.1 | 80 |
| 16 | 6.1 | 2.9 | >400 | >500 | | 1.7 | 45 |
| 17 | 1.5 | 0.28 | | | | 0.56 | 23 |
| 19 | 1.3 | 0.28 | | | | 1.2 | 19 |
| 20 | 1.4 | 0.31 | >50 | >25 | | 0.16 | 120 |
| 26 | 6.9 | 1.1 | >100 | >100 | | 2.1 | 560 |
| 29 | 3.1 | 0.35 | >50 | >25 | 3.1 | 1.1 | 330 |
| 30 | 1.4 | 0.95 | 280 | >50 | 1.0 | 0.37 | 80 |
| 31 | 14 | 3.3 | >100 | >100 | | 6.0 | 3.3 |
| 33 | 13 | 12 | >200 | >200 | 0.52 | 8.5 | 11 |
| 35 | 0.80 | 0.095 | >100 | >50 | 1.0 | 0.38 | 40 |
| 36 | 1.7 | 0.41 | >125 | >50 | 0.82 | 1.2 | 100 |
| 38 | 2.3 | 0.41 | >50 | >50 | 2.5 | 60 | >400 |
| 40 | 3.4 | 0.68 | >1000 | >500 | 1.8 | 1.2 | 32 |
| 44 | 3.8 | 0.95 | >500 | >100 | 1.1 | 1.2 | 60 |
| 45 | 0.58 | 0.091 | | | 0.84 | 0.46 | 70 |
| 47 | 8.9 | 1.0 | >400 | >200 | 7.5 | 4.5 | 130 |
| 48 | 5.3 | 3.4 | >200 | >100 | 22 | >100 | >200 |
| 54 | 1.0 | 0.19 | >200 | >100 | 1.0 | 0.45 | 35 |
| 55 | 1.2 | 0.29 | >125 | >50 | 2.6 | 0.42 | 57 |
| 56 | 1.9 | 0.29 | 500 | >100 | 1.2 | 0.76 | 46 |
| 57 | 4.6 | 3.3 | 730 | >500 | 0.73 | 1.4 | 45 |
| 58 | 3.4 | 0.72 | >125 | >50 | 1.3 | 2.8 | >150 |
| 59 | 1.4 | 0.18 | >125 | >250 | 0.67 | 0.42 | 40 |
| 62 | 1.8 | 0.58 | >200 | >100 | 2.4 | 8.3 | >500 |
| 63 | 5.6 | 1.4 | | >50 | 10 | 24 | >100 |
| 64 | 2.5 | 0.49 | >400 | >250 | 1.1 | 2.3 | 65 |
| 65 | 2.9 | 1.0 | | >50 | 5.0 | 22 | >200 |
| 66 | 0.80 | 0.092 | >50 | >50 | 3.9 | 0.54 | 350 |
| 67 | 1.1 | 0.14 | | >20 | 0.44 | 1.2 | 40 |
| 68 | 1.2 | 0.65 | >400 | >500 | 1.0 | 1.2 | 25 |
| 70 | 1.7 | 0.63 | 170 | >50 | 1.3 | 6.2 | 82 |
| 72 | 2.1 | 0.62 | >50 | >25 | 0.95 | 25 | >200 |
| 73 | 220 | 210 | >400 | >400 | 450 | >200 | >200 |
| 75 | 5.6 | 0.88 | >125 | >100 | 1.1 | 2.4 | 65 |
| 76 | 5.8 | 2.4 | >50 | >25 | 38 | >200 | >250 |
| 78 | 3.8 | 0.75 | >50 | >50 | 9.2 | 100 | >200 |
| 80 | 1.1 | 0.33 | >100 | >50 | 0.45 | 17 | >400 |
| 82 | 8.5 | 2.9 | >50 | >25 | 7.0 | 40 | >400 |
| 83 | 0.89 | 0.21 | >200 | >50 | 1.5 | 0.51 | 58 |
| 86 | 0.95 | 0.35 | >100 | >50 | 0.97 | 0.42 | 23 |
| 88 | 33 | >20 | >200 | >20 | 52 | 120 | >200 |
| 93 | 1.6 | 0.32 | >200 | >100 | 2.5 | 1.2 | 78 |
| 95 | 0.63 | 0.27 | >400 | >100 | 1.5 | 0.14 | 8.0 |
| 96 | 29 | 18 | >100 | >250 | 22 | 350 | >500 |
| 102 | 0.69 | 0.16 | >400 | >50 | 1.3 | 3.5 | 320 |
| 103 | 0.78 | 0.12 | | | 1.2 | 18 | >100 |

TABLE 2-continued

| Compound No. | Plasmin S-2251 | Fibrin | Thrombin S-2238 | Fibrinogen | Trypsin S-2238 | Plasma Kallikrein S-2302 | Urokinase S-2444 |
|---|---|---|---|---|---|---|---|
| 105 | 4.2 | 2.6 | >50 | >50 | 2.5 | 40 | >200 |
| 106 | 1.4 | 0.54 | | >50 | 3.0 | 19 | >150 |
| 109 | 0.58 | 0.27 | >50 | >40 | 0.43 | 20 | >200 |
| 111 | 5.2 | 1.1 | >50 | | 5.8 | >50 | >300 |
| 113 | 8.3 | 1.7 | | >50 | 18 | >25 | >20 |
| 114 | 3.2 | 1.4 | | | 9.5 | 40 | >100 |
| 118 | 3.4 | 0.77 | >50 | >50 | 3.0 | 3.7 | >150 |
| 121 | 0.95 | 0.43 | 280 | >200 | 0.24 | 0.18 | 19 |
| 122 | 1.1 | 0.31 | >200 | >50 | 1.0 | 0.43 | 34 |
| 123 | 0.39 | 0.28 | 95 | >50 | 0.71 | 0.078 | 26 |
| 125 | 0.49 | 0.13 | | | 0.80 | 0.38 | 47 |
| 126 | 1.5 | 0.83 | | >200 | 0.45 | 3.5 | 6.3 |
| 127 | 1.5 | 0.29 | >200 | >50 | 1.8 | 0.41 | 20 |
| 128 | 1.4 | 0.30 | >1000 | >100 | 1.3 | 0.44 | 82 |
| 130 | 15 | 7.1 | >400 | >400 | 0.50 | 8.3 | 34 |
| 131 | 170 | 56 | >200 | >500 | 4.4 | 17 | >250 |
| 137 | 0.90 | 0.58 | >400 | >200 | 1.2 | 0.66 | 37 |
| 139 | >1000 | 190 | >1000 | >1000 | | >1000 | >1000 |
| 140 | 8.8 | 2.5 | >200 | >200 | | 18 | >100 |
| 144 | 0.23 | 0.051 | | >50 | 0.95 | 0.37 | 43 |
| 145 | 0.56 | 0.075 | 86 | >50 | | 0.75 | 31 |
| 146 | 0.64 | 0.29 | >100 | >100 | | 0.58 | 45 |

TABLE 3

| No | Compound |
|---|---|
| 1 | H₂NCH₂—⟨cyclohexane⟩—COOH (t-AMCHA) |
| 2 | H₂N(CH₂)₅COOH (EACA) |
| 3 | |

TABLE 3-continued

| No | Compound |
|---|---|
| 5 | 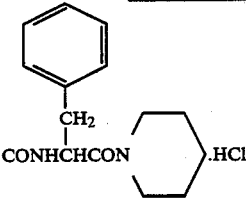 |

TABLE 4

| Compound No. | Plasmin S-2251 | Fibrin | Thrombin S-2238 | Fibrinogen | Trypsin S-2238 | Plasma Kallikrein S-2302 | Urokinase S-2444 |
|---|---|---|---|---|---|---|---|
| 1 | 75,000 | 60 | >1,000 | >1,000 | >1,000 | >1,000 | >1,000 |
| 2 | 180,000 | 200 | — | — | — | — | — |
| 3 | >1,000 | >1,000 | >1,000 | >1,000 | >300 | >1,000 | >1,000 |
| 4 | >100 | >100 | >100 | >100 | >150 | >100 | >100 |
| 5 | >200 | >200 | >200 | >200 | — | >200 | >200 |

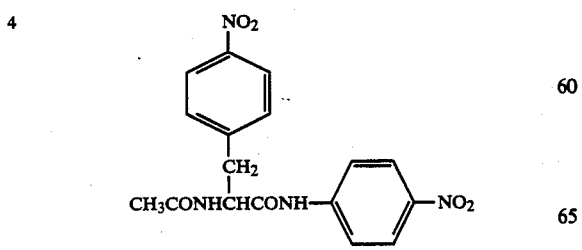

4

We claim:

1. A phenylalanine derivative having the formula (I):

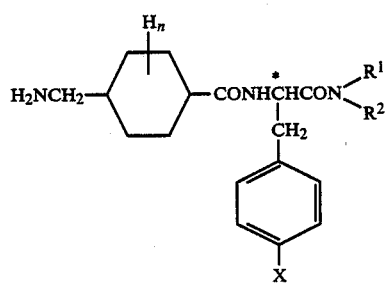

where $R^1$ and $R^2$ are, independently, hydrogen provided that both $R^1$ and $R^2$ are not hydrogen at the same time;

$C_1$–$C_8$ alkyl which may be substituted with hydroxy, hydroxycarbonyl, $C_1$–$C_4$ alkoxycarbonyl, $C_1$–$C_4$ alkylmercapto, $C_1$–$C_4$ alkoxy, carbamoyl, sulfamoyl, pyridyl, or phenyl which may further be substituted with nitro, $C_1$–$C_4$ alkoxy, or halogen;

$C_6$–$C_8$ cycloalkyl which may be substituted with hydroxy, $C_1$–$C_4$ alkoxy, hydroxylcarbonyl, $C_1$–$C_4$ alkoxycarbonyl, or $C_1$–$C_4$ alkyl;

phenyl which may be substituted with halogen, nitro, trifluoromethyl, $C_1$–$C_4$ alkoxy, $C_1$–$C_4$ alkylmercapto, $C_1$–$C_4$ alkylcarbonyl, phenylcarbonyl, hydroxycarbonyl, $C_1$–$C_4$ alkoxycarbonyl, carbamoyl, sulfamoyl, amidino, pyridylcarbonyl, or $C_1$–$C_6$ alkyl which may further be substituted with $C_1$–$C_4$ alkylcarbonyl, hydroxycarbonyl, or $C_1$–$C_4$ alkoxycarbonyl;

pyridyl which may be substituted with halogen or $C_1$–$C_4$ alkoxy;

pyrimidyl;

N-benzylazacyclohexyl; and $R^1$ and $R^2$ may form with the nitrogen atom attached thereto a ring structure selected from the group consisting of morpholino; thiomorpholino; piperazino which may be substituted with phenylcarbonyl, benzyl, or $C_1$–$C_4$ alkyl;

pyrrolidyl which may be substituted with hydroxycarbonyl or $C_1$–$C_4$ alkoxycarbonyl; and piperidino substituted with $C_1$–$C_4$ alkyl, phenyl $C_1$–$C_4$ alkyl, phenylcarbonyl, or $C_1$–$C_4$ alkoxycarbonyl;

X is hydrogen; nitro; amino; or —OZ wherein Z is hydrogen; $C_1$–$C_4$ alkyl; $C_2$–$C_4$ alkenyl; benzyl which may be substituted with halogen, $C_1$–$C_4$ alkyl, nitro, trifluoromethyl, hydroxycarbonyl, $C_1$–$C_4$ alkoxycarbonyl, or cyano; phenylcarbonylmethyl; pyridylmethyl; phenyl which may be substituted with nitro or halogen; pyridyl or pyrimidyl which may be substituted with nitro; phenylsulfonyl which may be substituted with $C_1$–$C_4$ alkyl; or benzyloxycarbonyl which may be substituted with halogen;

n is 4 to 10; and the mark * indicates that the configuration of the carbon may be either one of D-configuration, L-configuration and DL-configuration or a pharmaceutically acceptable salt thereof.

2. A phenylalanine derivative as claimed in claim 1, wherein the pharmaceutically acceptable salt is at least one salt selected from the group consisting of hydrochloride, hydrobromide, hydroiodide, sulfate, nitrate, phosphate, oxalate, succinate, glycolate, malate, citrate, lactate, benzene sulfonate, toluene sulfonate, and methane sulfonate.

3. A proteinase inhibitor composition comprising, as an essential component, a therapeutically effective amount of the phenylalanine derivative of claim 1 or a pharmaceutically acceptable salt thereof and a pharmaceutically acceptable carrier or diluent.

4. A proteinase inhibitor composition as claimed in claim 3, wherein the pharmaceutically acceptable salt is at least one salt selected from the group consisting of hydrochloride, hydrobromide, hydroiodide, sulfate, nitrate, phosphate, oxalate, succinate, glycolate, malate, citrate, lactate, benzene sulfonate, toluene sulfonate, and methane sulfonate.

* * * * *